(12) United States Patent
Egawa et al.

(10) Patent No.: US 11,739,129 B2
(45) Date of Patent: Aug. 29, 2023

(54) AP4 AND METHODS OF PROMOTING T CELL ACTIVATION

(71) Applicant: Washington University, St. Louis, MO (US)

(72) Inventors: Takeshi Egawa, St. Louis, MO (US); Chun Chou, St. Louis, MO (US)

(73) Assignee: Washington University, St. Louis, MO (US)

( * ) Notice: Subject to any disclaimer, the term of this patent is extended or adjusted under 35 U.S.C. 154(b) by 472 days.

(21) Appl. No.: 16/343,951

(22) PCT Filed: Oct. 20, 2017

(86) PCT No.: PCT/US2017/057689
§ 371 (c)(1),
(2) Date: Apr. 22, 2019

(87) PCT Pub. No.: WO2018/075941
PCT Pub. Date: Apr. 26, 2018

(65) Prior Publication Data
US 2019/0338003 A1 Nov. 7, 2019

Related U.S. Application Data

(60) Provisional application No. 62/411,297, filed on Oct. 21, 2016.

(51) Int. Cl.
| | |
|---|---|
| *A61K 35/00* | (2006.01) |
| *C07K 14/47* | (2006.01) |
| *A61K 35/17* | (2015.01) |
| *C12N 5/0783* | (2010.01) |
| *A61K 38/00* | (2006.01) |

(52) U.S. Cl.
CPC .......... *C07K 14/4702* (2013.01); *A61K 35/17* (2013.01); *C12N 5/0636* (2013.01); *A61K 38/00* (2013.01)

(58) Field of Classification Search
None
See application file for complete search history.

(56) References Cited

U.S. PATENT DOCUMENTS

2017/0267742 A1* 9/2017 Jensen .................. A61P 1/04

FOREIGN PATENT DOCUMENTS

| WO | 2015157399 A1 | 10/2015 |
| WO | 2018075941 A1 | 4/2018 |

OTHER PUBLICATIONS

Kim, J., "F-box proteins, cell cycle and cancer," Author Thesis, 2014, pp. 1-112, ISBN: 978-94-6203-741-0.*

D'Annibale et al., Proteasome-dependent Degradation of Transcription Factor Activating Enhancer-binding Protein 4 (TFAP4) Controls Mitotic Division The Journal of Biological Chemistry vol. 289, No. 11, pp. 7730-7737, Mar. 14, 2014.*
Venter et al., (2004; PN U.S. Pat. No. 6,812,339-B1.; See Score search results for SEQ ID No. 2, Result No. 1.*
Altschul, S. et al., "Basic Local Alignment Search Tool," J. Mol. Biol., 1990, pp. 403-410, vol. 215.
Altschul, S. et al., "Gapped BLAST and PSI-BLAST: a new generation of protein database search programs," Nucleic Acids Res., 1997, pp. 3389-3402, vol. 25, No. 17, Oxford University Press.
Barber, D. et al., "Restoring function in exhausted CD8 T cells during chronic viral infection," Nature, Feb. 9, 2006, pp. 682-687, vol. 439, with Online Methods.
Barna, M. et al., "Suppression of Myc oncogenic activity by ribosomal protein haploinsufficiency," Nature, Dec. 2008, pp. 971-975, vol. 456, with Methods.
Blattman, J. et al., "Therapeutic use of IL-2 to enhance antiviral T-cell responses in vivo," Nat. Med., May 2003, pp. 540-547, vol. 9, No. 5.
Boyman, O. et al., "The role of interleukin-2 during homeostasis and activation of the immune system," Nat. Rev. Immunol., Mar. 2012, pp. 180-190, vol. 12, Macmillan Publishers Limited.
Broxmeyer, H. et al., "High-efficiency recovery of functional hematopoietic progenitor and stem cells from human cord blood cryopreserved for 15 years," PNAS, Jan. 23, 2003, pp. 645-650, vol. 100, No. 2.
Brundler, M-A. et al., "Immunity to viruses in B cell-deficient mice: influence of antibodies on virus persistence and on T cell memory," Eur. J. Immunol., Sep. 1996, pp. 2257-2262, vol. 26, No. 9.
Cepko, C. et al., "Overview of the Retrovirus Transduction System," Current Protocols Mol. Biol., Oct. 1996, pp. 9.9.1-9.9.16, vol. 36, No. 1.
Chou, C. et al., "c-Myc-induced transcription factor AP4 is required for host protection mediated by CD8+ T cells," Nat. Immunol., Sep. 2014, pp. 884-893, vol. 15, No. 9.
Chou, C. et al., "Regulation of cytotoxic T cell and germinal center B cell responses by the c-MYC-AP4 transcription factor cascade," J. Immunol., May 1, 2016, vol. 196, No. 1 Supplement, 129.10, Abstract.
Chou, C. et al., "The Transcription Factor AP4 Mediates Resolution of Chronic Viral Infection through Amplification of Germinal Center B Cell Responses," Immunity, Sep. 20, 2016, pp. 570-582, vol. 45.
Crawford, A. et al., "Molecular and Transcriptional Basis of CD4(+) T Cell Dysfunction during Chronic Infection," Immunity, Feb. 20, 2014, pp. 289-302, vol. 40, Elsevier Inc.
Cui, W. et al., "Generation of effector CD8+ T cells and their conversion to memory T cells," Immunol. Rev., Jul. 2010, pp. 151-166, vol. 236, No. 1.
D'Annibale, S. et al., "Proteasome-dependent Degradation of Transcription Factor Activating Enhancer-binding Protein 4 (TFAP4) Controls Mitotic Division," J. Biol. Chem., Mar. 14, 2014, pp. 7730-7737, vol. 289, No. 11.
D'Souza, W. et al., "IL-2 Is Not Required for the Initiation of CD8 T Cell Cycling but Sustains Expansion," J. Immunol., 2003, pp. 5727-5735, vol. 171.

(Continued)

*Primary Examiner* — Maria G Leavitt
(74) *Attorney, Agent, or Firm* — Polsinelli PC

(57) ABSTRACT

The present disclosure provides a mutated form of AP4 that is more resistant to degradation relative to wild-type AP4. The disclosure also provides T cells expressing the mutated form of AP4 and methods of using the T cells in adoptive cellular immunotherapy.

13 Claims, 71 Drawing Sheets

Specification includes a Sequence Listing.

(56) References Cited

OTHER PUBLICATIONS

Egawa, T. et al., "Transcription factor AP4 modulates reversible and epigenetic silencing of the Cd4 gene," PNAS, Sep. 6, 2011, pp. 14873-14878, vol. 108, No. 36.

Frye, M. et al., "The RNA Methyltransferase Misu (NSun2) Mediates Myc-Induced Proliferation and Is Upregulated in Tumors," Current Biol., May 23, 2006, pp. 971-981, vol. 16.

Gautier, T. et al., "Nucleolar KKE/D Repeat Proteins Nop56p and Nop58p Interact with Nop1p and Are Required for Ribosome Biogenesis," Mol. Cell Biol., Dec. 1997, pp. 7088-7098, vol. 17, No. 12.

Grajales-Reyes, G. et al., "Batf3 maintains autoactivation of Irf8 for commitment of a CD8alpha(+) conventional DC clonogenic progenitor," Nat. Immunol., Jul. 2015, pp. 708-717, vol. 16, No. 7, with Online Methods.

Harker, J. et al., "Late Interleukin-6 Escalates T Follicular Helper Cell Responses and Controls a Chronic Viral Infection," Sci., Nov. 11, 2011, pp. 825-829, vol. 334, No. 6057.

Hayano, T. et al., "Proteomic Analysis of Human Nop56p-associated Pre-ribosomal Ribonucleoprotein Complexes," J. Biol. Chem., Sep. 5, 2003, pp. 34309-34319, vol. 278, No. 36.

Henson, D. et al., "A Silencer-Proximal Intronic Region Is Required for Sustained CD4 Expression in Postselection Thymocytes," J. Immunol., 2014, pp. 4620-4627, vol. 192.

Hirsch, C. et al., "Turnover of Liver Ribosomes in Fed and in Fasted Rats," J. Biol. Chem., Dec. 25, 1966, pp. 5936-5940, vol. 241, No. 24.

Hoffman, B. et al., "Apoptotic signaling by c-MYC," Oncogene, 2008, pp. 6462-6472, vol. 27.

Hu, Y. et al., "Transcription factor AP-4 contains multiple dimerization domains that regulate dimer specificity," Genes Dev., 1990, pp. 1741-1752, vol. 4.

Huang, C. et al., "Dynamic regulation of c-Myc proto-oncogene expression during lymphocyte development revealed by a GFP-c-Myc knock-in mouse," Eur. J. Immunol., 2008, pp. 342-349, vol. 38.

International Search Report and Written Opinion dated Mar. 19, 2018 from related Patent Application No. PCT/US2017/057689; 11 pgs.

Johnson, L. et al., "A Chronic Need for IL-21," Sci., Jun. 19, 2009, pp. 1525-1526, vol. 324, No. 5934.

Joshi, N. et al., "Inflammation Directs Memory Precursor and Short-Lived Effector CD8(+) T Cell Fates via the Graded Expression of T-bet Transcription Factor," Immunity, Aug. 2007, pp. 281-295, vol. 27.

Kaech, S. et al., "Heterogeneity and Cell-Fate Decisions in Effector and Memory CD8+ T Cell Differentiation during Viral Infection," Immunity, Sep. 2007, pp. 393-405, vol. 27.

Kaech, S. et al., "Transcriptional control of effector and memory CD8+ T cell differentiation," NIH Public Access Author Manuscript, Aug. 19, 2014, pp. 1-33, Published in final edited form as: Nat. Rev. Immunol., Nov. 2012, pp. 749-761, vol. 12, No. 11.

Kahan, S. et al., "T cell exhaustion during persistent viral infections," Virology, 2015, pp. 180-193, vol. 479-480.

Kalia, V. et al., "Prolonged Interleukin-2Ralpha Expression on Virus-Specific CD8+ T Cells Favors Terminal-Effector Differentiation in Vivo," Immunity, Jan. 29, 2010, pp. 91-103, vol. 32.

Karlin, S. et al., "Applications and statistics for multiple high-scoring segments in molecular sequences," PNAS, Jun. 1993, pp. 5873-5877, vol. 90.

Kim, B. et al., "Restriction of Nonpermissive RUNX3 Protein Expression in T Lymphocytes by the Kozak Sequence," J. Immunol., Jul. 2015, pp. 1517-1523, vol. 195.

Loven, J. et al., "Revisiting Global Gene Expression Analysis," Cell, Oct. 26, 2012, pp. 476-482, vol. 151.

Luscher, B. et al., "c-myc and c-myb Protein Degradation: Effect of Metabolic Inhibitors and Heat Shock," Mol. Cell. Biol., Jun. 1988, pp. 2504-2512, vol. 8, No. 6.

Maekawa, Y. et al., "Notch2 integrates signaling by the transcription factors RBP-J and CREB1 to promote T cell cytotoxicity," Nat. Immunol., Oct. 2008, pp. 1140-1147, vol. 9, No. 10.

Matsushita, H. et al., "Cancer exome analysis reveals a T-cell-dependent mechanism of cancer immunoediting," Nature, Feb. 16, 2012, pp. 400-404, vol. 482.

Mermod, N. et al., "Enhancer binding factors AP-4 and AP-1 act in concert to activate SV40 late transcription in vitro," Nature, Apr. 7, 1988, pp. 557-561, vol. 332.

Miller, B., "The Biological Half-Lives of Ribosomal and Transfer RNA in the Mouse Uterus," J. Endocr., 1973, pp. 81-85, vol. 59, No. 1.

NCBI Reference Sequence NM_003223.2, "*Homo sapiens* transcription factor AP-4 (TFAP4), mRNA," Jun. 11, 2019; 5 pgs.

NCBI Reference Sequence NP_001094685.1, "transcription factor AP-4 [Bos Taurus]," May 14, 2018; 2 pgs.

NCBI Reference Sequence NP_001101737.1, "transcription factor AP-4 [Rattus norvegicus]," May 28, 2018; 3 pgs.

NCBI Reference Sequence NP_001123841.1, "transcription factor AP-4 [Xenopus tropicalis]," Oct. 29, 2016; 2 pgs.

NCBI Reference Sequence NP_003214.1, "transcription factor AP-4 [*Homo sapiens*]," Jun. 11, 2019; 4 pgs.

NCBI Reference Sequence NP_112459.1, "transcription factor AP-4 [Mus musculus]," Jan. 27, 2019; 3 pgs.

NCBI Reference Sequence XP_006942452.1, "transcription factor AP-4 isoform X3 [Felis catus]," Dec. 12, 2017; 2 pgs.

NCBI Reference Sequence XP_547149.2, "transcription factor AP-4 isoform X1 [Canis lupus familiaris]," Sep. 5, 2017; pgs. 2.

Odorizzi, P. et al., "Inhibitory Receptors on Lymphocytes: Insights from Infections," J. Immunol., 2012, pp. 2957-2965, vol. 188.

Odorizzi, P. et al., "Genetic absence of PD-1 promotes accumulation of terminally differentiated exhausted CD8+ T cells," J. Exp. Med., 2015, pp. 1-13, vol. 212.

Pipkin, M. et al., "Interleukin-2 and Inflammation Induce Distinct Transcriptional Programs that Promote the Differentiation of Effector Cytolytic T Cells," Immunity, Jan. 29, 2010, pp. 79-90, vol. 32.

Qian, X. et al., "Cell Transfer Therapy for Cancer: Past, Present, and Future," J. Immunol. Res., 2014, pp. 1-9, vol. 2014, Article 525913.

Rosenberg, S., "IL-2: The First Effective Immunotherapy for Human Cancer," J. Immunol., 2014, pp. 5451-5458, vol. 192.

Ruggero, D., "The Role of Myc-Induced Protein Synthesis in Cancer," Cancer Res., Dec. 1, 2009, pp. 8839-8843, vol. 69, No. 23.

Sander, S. et al., "Synergy between PI3K Signaling and MYC in Burkitt Lymphomagenesis," Cancer Cell, Aug. 14, 2012, pp. 167-179, vol. 22.

Sarkar, S. et al., "Functional and genomic profiling of effector CD8 T cell subsets with distinct memory fates," J. Exp. Med., 2008, pp. 1-16, vol. 205.

Satpathy, A. et al., "Runx1 and Cbfbeta regulate the development of Flt3+ dendritic cell progenitors and restrict myeloproliferative disorder," Blood, May 8, 2014, pp. 2968-2977, vol. 123, No. 19.

Scheinkonig, C. et al., "Adoption of long-term cultures to evaluate the cryoprotective potential of trehalose for freezing hematopoietic stem cells," Bone Marrow Transplant., 2004, pp. 531-536, vol. 34.

Schraml, B. et al., "The AP-1 transcription factor Batf controls T(H)17 differentiation," HHS Public Access Author Manuscript, Jan. 16, 2010, pp. 1-13, Published in final edited form as: Nature, Jul. 16, 2009, p. 405-409, vol. 460, No. 7253.

Shedlock, D. et al., "Requirement for CD4 T cell help in generating functional CD8 T cell memory," Sci., Apr. 11, 2003, pp. 337-339, vol. 300, No. 5617.

Shrestha, B. et al., "Role of CD8+ T Cells in Control of West Nile Virus Infection," J. Virol., Aug. 2004, pp. 8312-8321, vol. 78, No. 15.

Sim, G. et al., "The IL-2 cytokine family in cancer immunotherapy," Cytokine Growth Factor Rev., Aug. 2014, pp. 377-390, vol. 25, No. 4.

Sinclair, L. et al., "Antigen receptor control of amino acid transport coordinates the metabolic re-programming that is essential for T cell differentiation," Europe PMC Funders Group Author Manuscript, Nov. 1, 2013, pp. 1-24, Published in final edited form as: Nat. Immunol., May 2013, pp. 500-508, vol. 14, No. 5.

Suthar, M. et al., "West Nile virus infection and immunity," Nat. Rev. Microbiol., Feb. 2013, pp. 115-128, vol. 11.

UniProtKB Accession No. Q01664, "TFAP4_Human Transcription Factor AP-4," Oct. 1, 1993, 11 pgs.

(56) References Cited

OTHER PUBLICATIONS

Virgin, H. et al., "Redefining Chronic Viral Infection," Cell, Jul. 10, 2009, pp. 30-50, vol. 138.

Wang, R. et al., "The Transcription Factor Myc Controls Metabolic Reprogramming upon T Lymphocyte Activation," Immunity, Dec. 23, 2011, pp. 871-882, vol. 35.

West, E. et al., "PD-L1 blockade synergizes with IL-2 therapy in reinvigorating exhausted T cells," J. Clin. Invest., Jun. 2013, pp. 2604-2615, vol. 123, No. 6.

Wherry, E. et al., "Viral Persistence Alters CD8 T-Cell Immunodominance and Tissue Distribution and Results in Distinct Stages of Functional Impairment," J. Virol., Apr. 2003, pp. 4911-4927, vol. 77, No. 8.

Wherry, E. et al., "Molecular Signature of CD8+ T Cell Exhaustion during Chronic Viral Infection," Immunity, Oct. 2007, pp. 670-684, vol. 27.

Williams, M. et al., "Interleukin-2 signals during priming are required for secondary expansion of CD8+ memory T cells," NIH Public Access Author Manuscript, Nov. 11, 2009, pp. 1-12, Published in final edited form as: Nature, Jun. 15, 2006, pp. 890-893, vol. 441, No. 7095.

Youngblood, B. et al., "Acquired Transcriptional Programming in Functional and Exhausted Virus-specific CD8 T Cells," NIH Public Access Author Manuscript, Jan. 1, 2012, pp. 1-12, Published in final edited form as: Curr. Opin. HIV Aids, Jan. 2012, pp. 50-57, vol. 7, No. 1.

Zehn, D. et al., "Complete but curtailed T-cell response to very low-affinity antigen," HHS Public Access Author Manuscript, Sep. 12, 2009, pp. 1-11, Published in final edited form as: Nature, Mar. 12, 2009, pp. 211-214, vol. 458, No. 7235.

\* cited by examiner

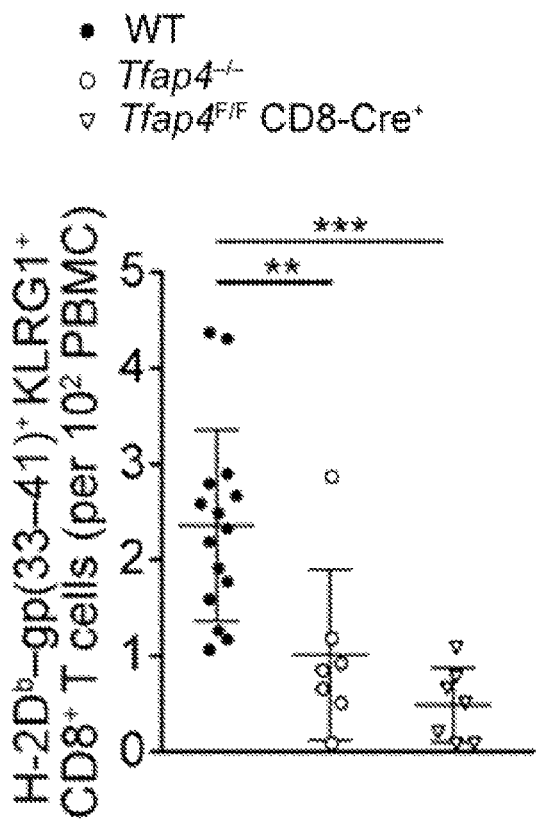 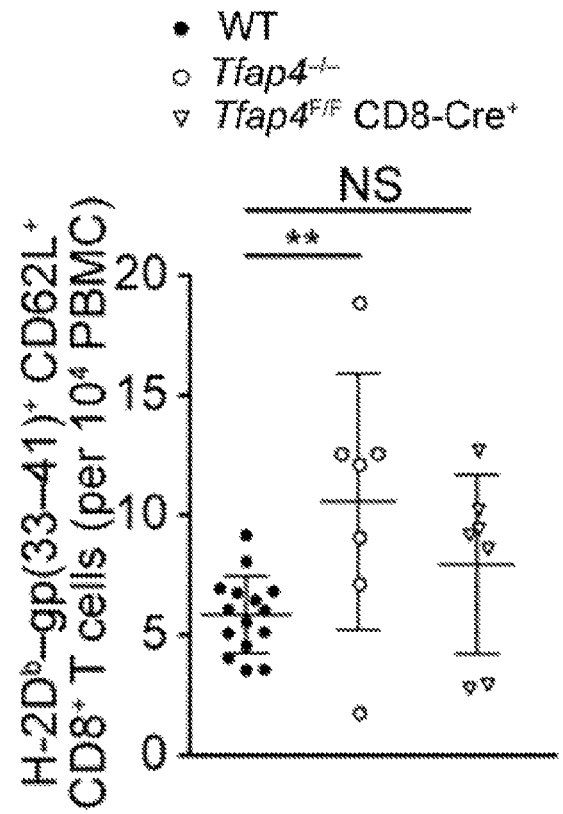
FIG. 4H     FIG. 4I

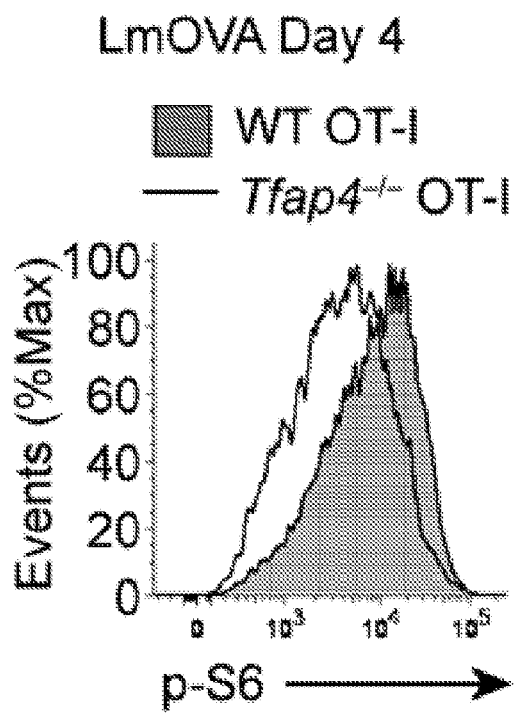
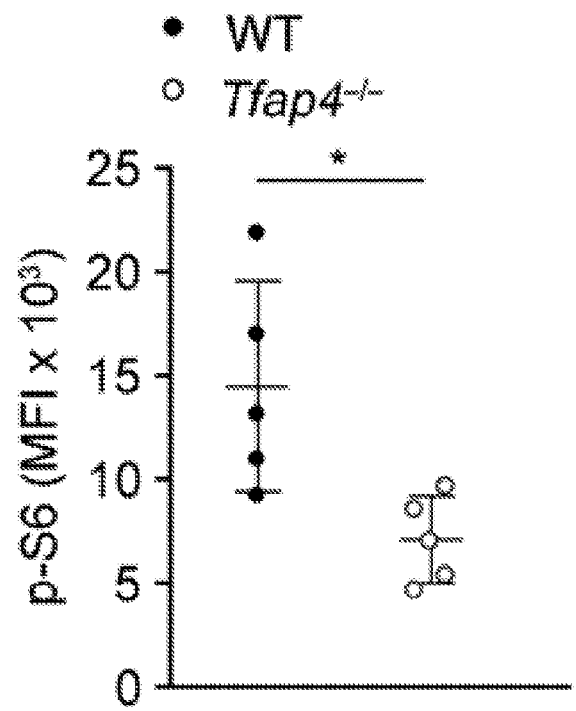
FIG. 6G  FIG. 6H
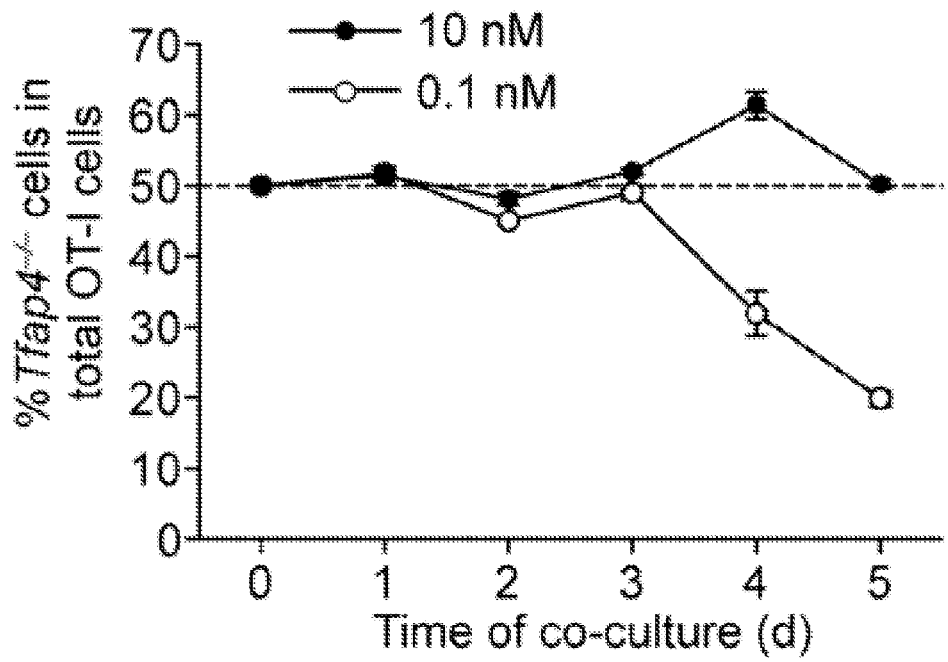
FIG. 6I

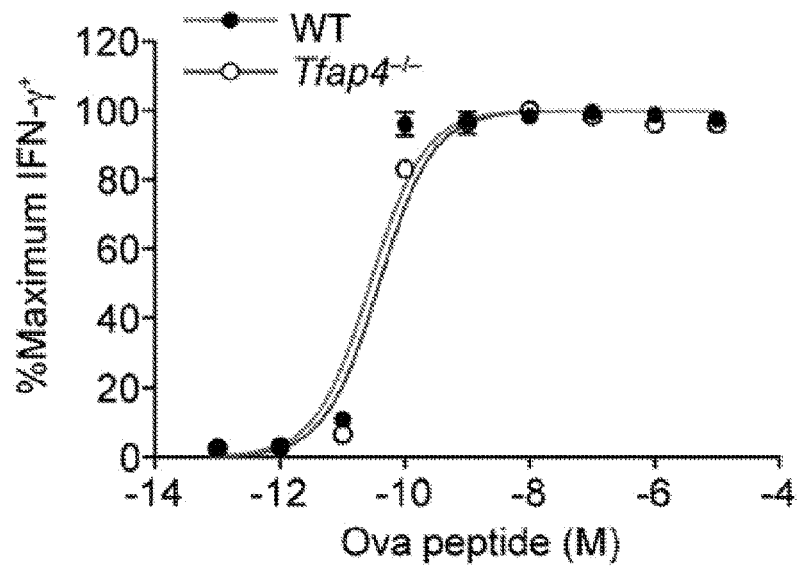
FIG. 6L
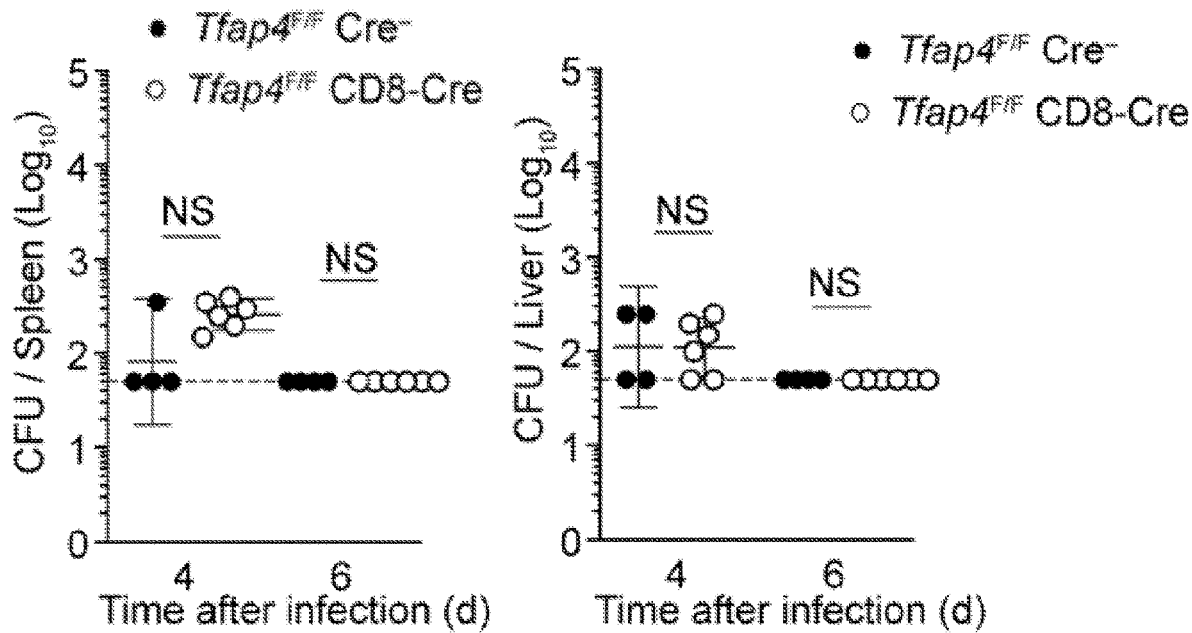
FIG. 6M  FIG. 6N

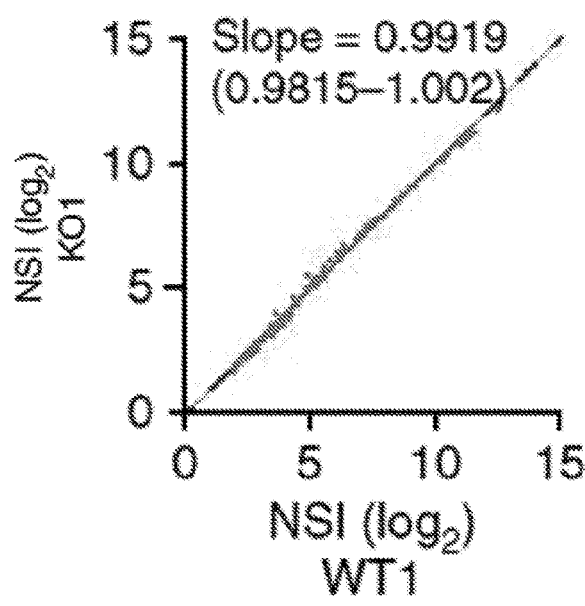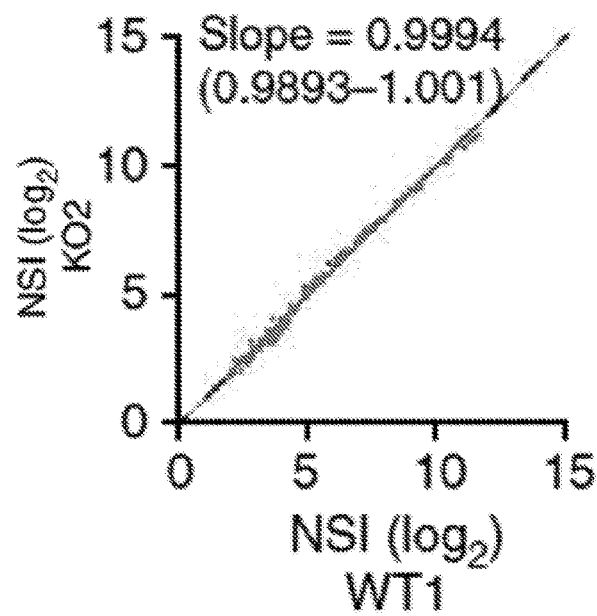
FIG. 11E  FIG. 11F

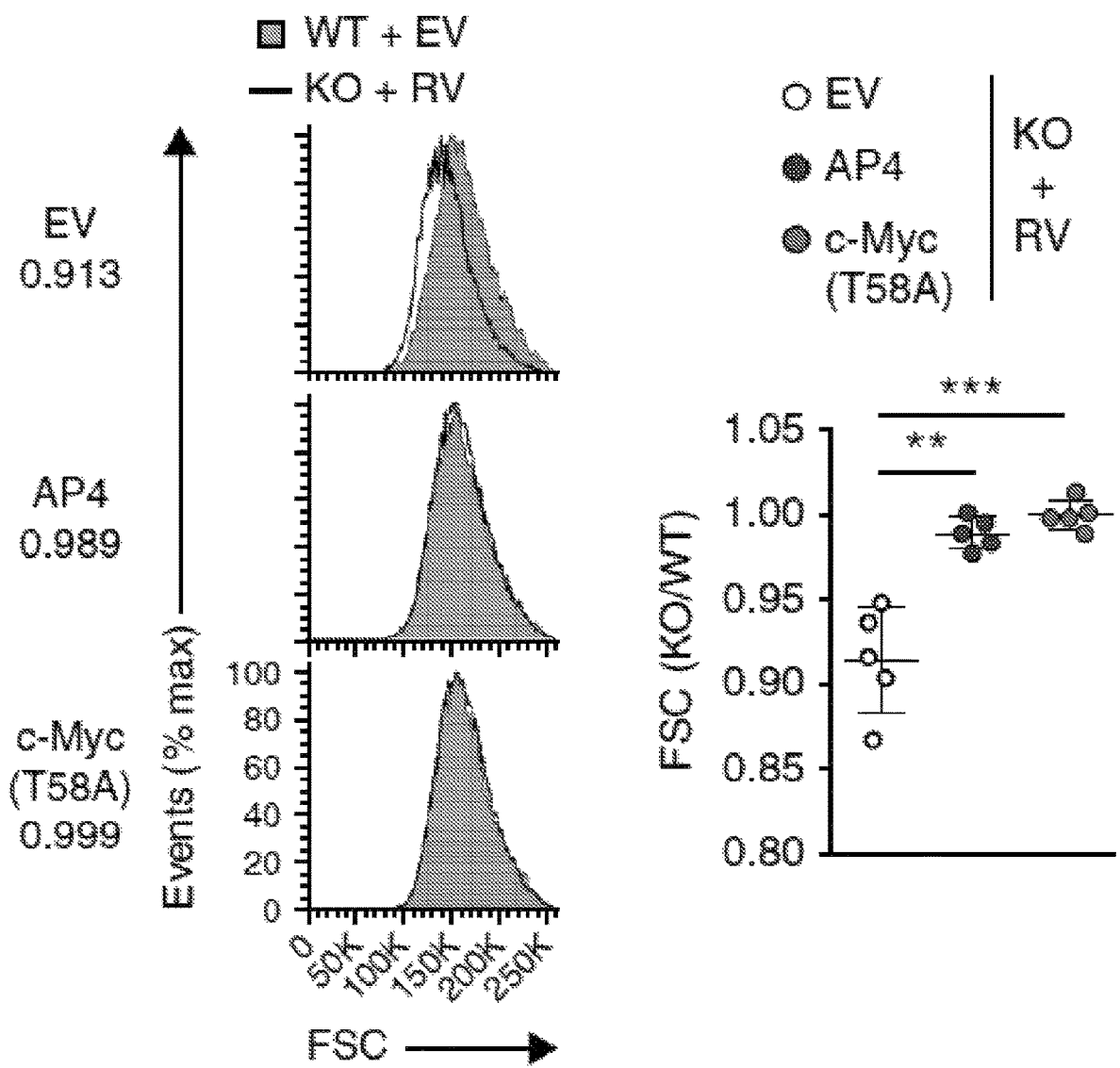
FIG. 12A      FIG. 12B

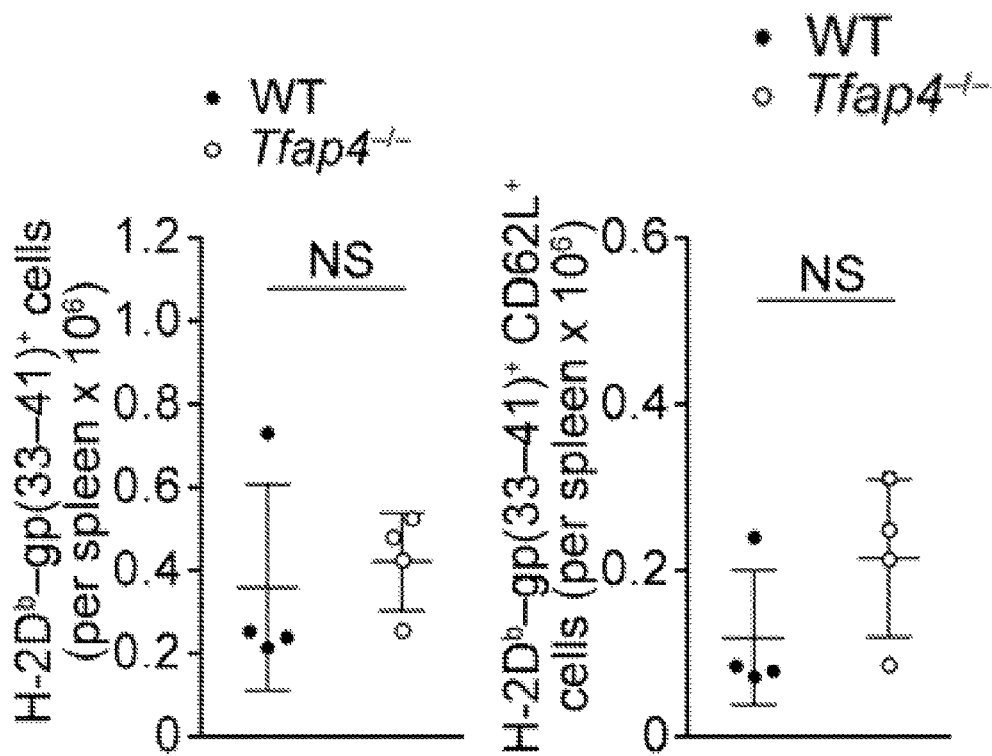
FIG. 17B   FIG. 17C

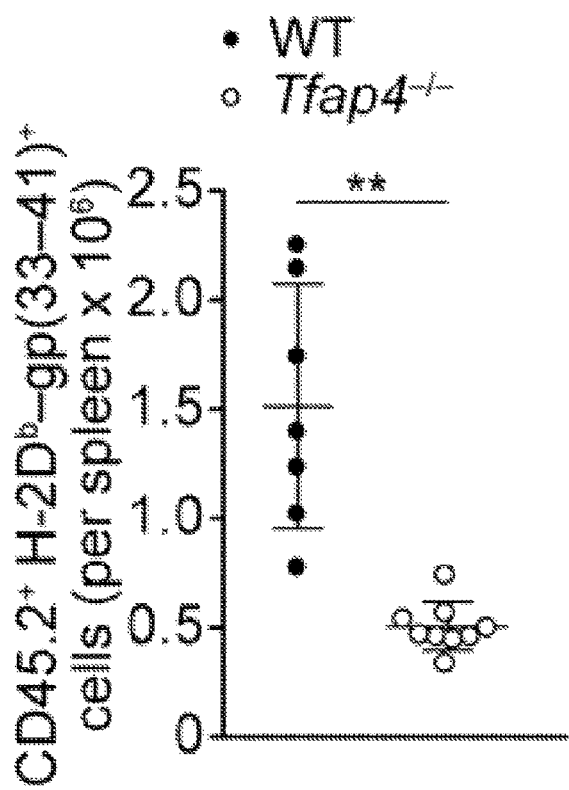
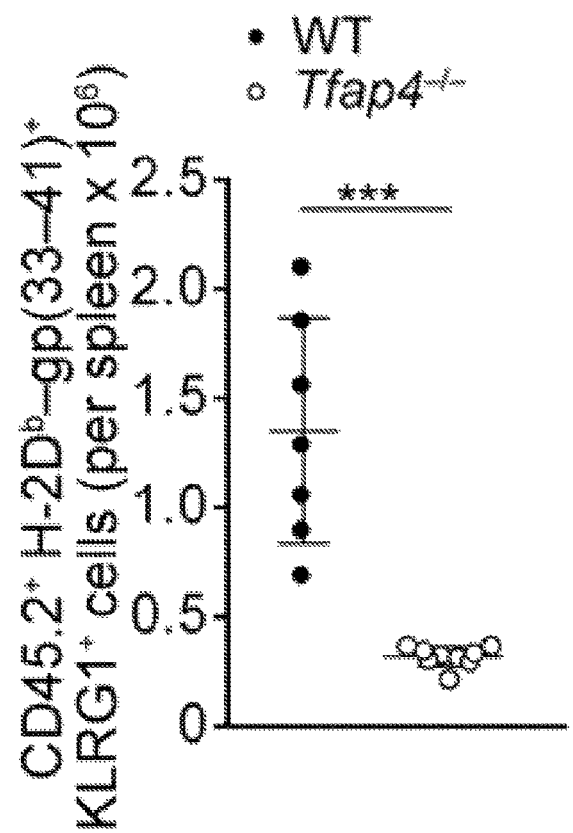
FIG. 17H  FIG. 17I

| OT-I Rosa26^CreERT2 | Tamoxifen | | Clonal expansion | |
|---|---|---|---|---|
| | Primary | Secondary | Primary | Secondary |
| Tfap4+/+ | AP4(+) | AP4(+) | normal | normal |
| Tfap4F/F | AP4(+) | AP4(-) | normal | ? |
| Tfap4-/- | AP4(-) | AP4(-) | defective | defective |
| Rosa26^LSL-sAP4 Tfap4-/- | AP4(-) | AP4(+) | defective | ? |

FIG. 18

SEQUENCE LISTING

```
<160> NUMBER OF SEQ ID NOS: 2

<210> SEQ ID NO 1
<211> LENGTH: 338
<212> TYPE: PRT
<213> ORGANISM: Artificial Sequence
<220> FEATURE:
<223> OTHER INFORMATION: SYNTHESIZED

<400> SEQUENCE: 1

Met Glu Tyr Phe Met Val Pro Thr Gln Lys Val Pro Ser Leu Gln His
1               5                   10                  15

Phe Arg Lys Thr Glu Lys Glu Val Ile Gly Gly Leu Cys Ser Leu Ala
            20                  25                  30

Asn Ile Pro Leu Thr Pro Glu Thr Gln Arg Asp Gln Glu Arg Arg Ile
        35                  40                  45

Arg Arg Glu Ile Ala Asn Ser Asn Glu Arg Arg Met Gln Ser Ile
    50                  55                  60

Asn Ala Gly Phe Gln Ser Leu Lys Thr Leu Ile Pro His Thr Asp Gly
65                  70                  75                  80
```

```
Glu Lys Leu Ser Lys Ala Ala Ile Leu Gln Gln Thr Ala Glu Tyr Ile
            85                  90                  95

Phe Ser Leu Glu Gln Glu Lys Thr Arg Leu Leu Gln Gln Asn Thr Gln
        100                 105                 110

Leu Lys Arg Phe Ile Gln Glu Leu Ser Gly Ser Pro Lys Arg Arg
        115                 120                 125

Arg Ala Glu Asp Lys Asp Gly Ile Gly Ser Pro Asp Ile Trp Glu
130                 135                 140

Asp Glu Lys Ala Glu Asp Leu Arg Arg Glu Met Ile Glu Leu Arg Gln
145                 150                 155                 160

Gln Leu Asp Lys Glu Arg Ser Val Arg Met Met Leu Glu Glu Gln Val
                165                 170                 175

Arg Ser Leu Glu Ala His Met Tyr Pro Glu Lys Leu Lys Val Ile Ala
            180                 185                 190

Gln Gln Val Gln Leu Gln Gln Gln Glu Gln Val Arg Leu Leu His
        195                 200                 205

Gln Glu Lys Leu Glu Arg Glu Gln Gln Leu Arg Thr Gln Leu Leu
        210                 215                 220

Pro Pro Pro Ala Pro Thr His His Pro Thr Val Ile Val Pro Ala Pro
225                 230                 235                 240

Pro Pro Pro Pro Ser His His Ile Asn Val Val Thr Met Gly Pro Ser
                245                 250                 255

Ser Val Ile Asn Ser Val Ser Thr Ser Arg Gln Asn Leu Asp Thr Ile
            260                 265                 270

Val Gln Ala Ile Gln His Ile Glu Gly Thr Gln Glu Lys Gln Glu Leu
        275                 280                 285

Glu Glu Glu Gln Arg Arg Ala Val Ile Val Lys Pro Val Arg Ser Cys
290                 295                 300

Pro Glu Ala Pro Thr Ser Asp Thr Ala Ser Asp Ser Glu Ala Ser Asp
305                 310                 315                 320

Ser Asp Ala Met Asp Gln Ser Arg Glu Glu Pro Ser Gly Asp Gly Glu
                325                 330                 335

Leu Pro

<210> SEQ ID NO 2
<211> LENGTH: 338
<212> TYPE: PRT
<213> ORGANISM: Artificial Sequence
<220> FEATURE:
<223> OTHER INFORMATION: SYNTHESIZED

<400> SEQUENCE: 2

Met Glu Tyr Phe Met Val Pro Thr Gln Lys Val Pro Ser Leu Gln His
1               5                   10                  15

Phe Arg Lys Thr Glu Lys Glu Val Ile Gly Gly Leu Cys Ser Leu Ala
            20                  25                  30

Asn Ile Pro Leu Thr Pro Glu Thr Gln Arg Asp Gln Glu Arg Arg Ile
        35                  40                  45

Arg Arg Glu Ile Ala Asn Ser Asn Glu Arg Arg Met Gln Ser Ile
    50                  55                  60

Asn Ala Gly Phe Gln Ser Leu Lys Thr Leu Ile Pro His Thr Asp Gly
65                  70                  75                  80

Glu Lys Leu Ser Lys Ala Ala Ile Leu Gln Gln Thr Ala Glu Tyr Ile
            85                  90                  95

Phe Ser Leu Glu Gln Glu Lys Thr Arg Leu Leu Gln Gln Asn Thr Gln
```

-continued

```
                100                 105                 110
Leu Lys Arg Phe Ile Gln Glu Leu Ser Gly Ser Ser Pro Lys Arg Arg
            115                 120                 125

Arg Ala Glu Asp Lys Asp Glu Ile Gly Ala Pro Asp Ile Trp Glu
    130                 135                 140

Asp Glu Lys Ala Glu Asp Leu Arg Arg Glu Met Ile Glu Leu Arg Gln
145                 150                 155                 160

Gln Leu Asp Lys Glu Arg Ser Val Arg Met Met Leu Glu Glu Gln Val
            165                 170                 175

Arg Ser Leu Glu Ala His Met Tyr Pro Glu Lys Leu Lys Val Ile Ala
            180                 185                 190

Gln Gln Val Gln Leu Gln Gln Gln Glu Gln Val Arg Leu Leu His
            195                 200                 205

Gln Glu Lys Leu Glu Arg Glu Gln Gln Gln Leu Arg Thr Gln Leu Leu
            210                 215                 220

Pro Pro Pro Ala Pro Thr His His Pro Thr Val Ile Val Pro Ala Pro
225                 230                 235                 240

Pro Pro Pro Ser His His Ile Asn Val Val Thr Met Gly Pro Ser
            245                 250                 255

Ser Val Ile Asn Ser Val Ser Thr Ser Arg Gln Asn Leu Asp Thr Ile
            260                 265                 270

Val Gln Ala Ile Gln His Ile Glu Gly Thr Gln Glu Lys Gln Glu Leu
            275                 280                 285

Glu Glu Glu Gln Arg Arg Ala Val Ile Val Lys Pro Val Arg Ser Cys
            290                 295                 300

Pro Glu Ala Pro Thr Ser Asp Thr Ala Ser Asp Ser Glu Ala Ser Asp
305                 310                 315                 320

Ser Asp Ala Met Asp Gln Ser Arg Glu Glu Pro Ser Gly Asp Gly Glu
            325                 330                 335

Leu Pro
```

AP4 AND METHODS OF PROMOTING T CELL ACTIVATION

CROSS REFERENCE TO RELATED APPLICATIONS

This application claims the benefit of International Patent Application number PCT/US2017/057689, filed Oct. 20, 2017, which claims the benefit of U.S. Provisional Application No. 62/411,297, filed Oct. 21, 2016, the disclosures of which are hereby incorporated by reference in their entirety.

GOVERNMENTAL RIGHTS

This invention was made with government support under AI097244 and AI114593 awarded by the National Institutes of Health. The government has certain rights in the invention.

REFERENCE TO SEQUENCE LISTING

This application contains a Sequence Listing that has been submitted in ASCII format via EFS-Web and is hereby incorporated by reference in its entirety. The ASCII copy, created on Apr. 22, 2019, is named Untitled_ST25.txt, and is 6,276 bytes in size.

FIELD OF THE INVENTION

The present disclosure provides a mutated form of AP4 that is more resistant to degradation relative to wild-type AP4. The disclosure also provides T cells expressing the mutated form of AP4 and methods of using the T cells in adoptive cellular immunotherapy.

BACKGROUND OF THE INVENTION

T cell immune responses are critical for host protection against infections and cancers. Upon activation, $CD8^+$ cytotoxic T cells rapidly proliferate to increase their frequencies (clonal expansion), and elevate their expression of cytokines and cytolytic molecules (effector differentiation). These cellular programs must be maintained until cancer cells or intracellular pathogens, such as viruses, are completely eliminated from the host. Thus, there is a need in the art to enhance T cell expansion and effector differentiation to improve upon current adoptive cellular immunotherapy.

SUMMARY OF THE INVENTION

One aspect of the present disclosure is directed to a composition comprising T cells. The T cells express AP4 and the AP4 comprises a S139 mutation relative to SEQ ID NO: 1 and exhibit increased stability relative to wild-type AP4 and induces T cell proliferation.

Another aspect of the present disclosure is directed to a method to increase and prolong the expression of AP4 in CD8+ T cells. The method comprises transfecting CD8+ T cells with a vector comprising a polynucleotide sequence encoding a polypeptide comprising AP4. The AP4 comprises a S139A mutation relative to SEQ ID NO: 1 and exhibits increased stability relative to wild-type AP4 and induces T cell proliferation.

An additional aspect of the present disclosure is directed to a method to increase CD8+ T cell clonal expansion and effector differentiation. The method comprises transfecting CD8+ T cells with a vector comprising a polynucleotide sequence encoding a polypeptide comprising AP4. The AP4 comprises a S139A mutation relative to SEQ ID NO: 1 and exhibits increased stability relative to wild-type AP4 and induces T cell proliferation.

Another aspect of the present disclosure is directed to a method to enhance anti-tumor CD8+ T cell function. The method comprises transfecting CD8+ T cells with a vector comprising a polynucleotide sequence encoding a polypeptide comprising AP4. The AP4 comprises a S139A mutation relative to SEQ ID NO: 1 and exhibits increased stability relative to wild-type AP4 and induces T cell proliferation.

Another aspect of the present disclosure is directed to a method to improve adoptive cellular immunotherapy in a subject. The method comprises administering to the subject a therapeutic composition comprising T cells. The T cells express AP4 and the AP4 comprises a S139 mutation relative to SEQ ID NO: 1 and exhibit increased stability relative to wild-type AP4 and induces T cell proliferation.

A further aspect of the present disclosure is directed to a method to reduce tumor growth in a subject. The method comprises administering to the subject a therapeutic composition comprising T cells. The T cells express AP4 and the AP4 comprises a S139 mutation relative to SEQ ID NO: 1 and exhibit increased stability relative to wild-type AP4 and induces T cell proliferation.

Other aspects and iterations of the disclosure are described in more detail below.

BRIEF DESCRIPTION OF THE FIGURES

The application file contains at least one drawing executed in color. Copies of this patent application publication with color drawing(s) will be provided by the Office upon request and payment of the necessary fee.

(FIG. 2A) Immunoblot showing AP4 expression in IL-2-treated or IL-2-deprived Tfap4$^{-/-}$ $CD8^+$ T cells transduced with an empty (EV) or AP4-expressing RV. (n=2). (FIG. 2B) Immunoblot analysis of AP4 in IL-2-treated or IL-2-deprived $CD8^+$ T cells in the presence of cycloheximide (CHX, 10 µM) for indicated time. (n=2). (FIG. 2C) Immunoblot analysis of AP4 in IL-2-deprived $CD8^+$ T cells in the presence of MG-132 (10 µM) for indicated time. (n=2). (FIG. 2D) Immunoblot analysis of AP4 in $CD8^+$ T cells stimulated with different concentrations of anti-CD3 antibody for 12 hours (left, n=2) or with indicated cytokines for 12 hours after 2 day stimulation with anti-CD3 antibody (right, n=2). (FIG. 2E) Immunoblot analysis of AP4 in $CD8^+$ T cells stimulated with anti-CD3 and anti-CD28 antibodies for 48 hours followed by treatments with indicated chemicals for 6 h (left, n=2) and in those treated with chemicals after IL-2 stimulation for 24 h following anti-CD3 and anti-CD28 antibody stimulation (right, n=2). Wort: Wortmannin. (FIG. 2F) Immunoblot analysis of AP4, Blimp-1 and T-bet in adoptively transferred P14 T cells at indicated time points after LCMV-Arm infection. (FIG. 2G, FIG. 2H, and FIG. 2I) Histogram showing CD25 expression in CD8+ CD44+ CD62L− T cells in B6 mice on day 4.5 after LCMV-Arm infection (FIG. 2G), immunoblots showing AP4, Blimp-1 and T-bet expression (FIG. 2H), and qRT-PCR analysis showing Tfap4 expression (FIG. 2I) in CD25$^{Lo}$ and CD25$^{Hi}$ cells. (n=2). Error bars, s.d. (FIG. 2J) Immunoblots showing AP4 expression in Il2ra$^{-/-}$ P14 T cells on day 4 post LCMV-Arm infection. (n=2). *P<0.05 by unpaired t-test.

(FIG. 3A and FIG. 3B) Flow cytometry of splenocytes from Tfap4$^{-/-}$ and WT mice 8 days after LCMV infection showing CD4, CD8, KLRG1 and CD62L expression and binding of an H-2D$^b$-gp(33-41) tetramer. Percentages of CD8+ T cells, CD8+ KLRG1+ effector cells, and gp(33-41)-specific CD8+ T cells of the total splenocytes (FIG. 3C and FIG. 3D) and percentages of CD62L+ and KLRG1+ cells in gp(33-41)-specific CD8+ T cells (FIG. 3E, FIG. 3F, and FIG. 3G) are shown with gates indicated as rectangles. Statistical analysis of data from ten WT and eight Tfap4$^{-/-}$ mice. (FIG. 3H, FIG. 3I, and FIG. 3J) qRT-PCR analysis of the LCMV GP transcript in spleen (FIG. 3H), kidney (FIG. 3I), and liver (FIG. 3J) of Tfap4$^{F/F}$ CD8-Cre+ and control Tfap4$^{F/F}$ Cre− mice 6 days after LCMV-Arm infection. Transcript levels were normalized against Hprt1 levels. Data from five mice in two experiments were combined. Dotted lines indicate the limit of detection. Error bars, s.d. *P<0.0001 by unpaired t-test. NS: not significant.

FIG. 4A, FIG. 4B, FIG. 4C, FIG. 4D, FIG. 4E, FIG. 4F, FIG. 4G, FIG. 4H, and FIG. 4I depict a schematic, graphs and flow cytometry plots showing that AP4 is cell-autonomously required for CD8+ T cell expansion. (FIG. 4A) A gene-targeting strategy shown with representative restriction enzyme sites used for screening by Southern blot with a 5' external probe (gray square). LoxP sites were inserted to flank exons 2 to 4 of Tfap4 in ES cells. The loxP-neo cassette was deleted in vitro by transient Cre transfection in ES cells prior to blastocyst injection. (FIG. 4B) qRT-PCR analysis of RNA of CD4+ and CD8+ T cells purified from Tfap4$^{F/F}$ Cre− or Tfap4$^{F/F}$ CD8-Cre+ mice showing Tfap4 expression in CD8+ T cells by the CD8-Cre deleter line. (n=3). (FIG. 4C, FIG. 4D, FIG. 4E, FIG. 4F, FIG. 4G, FIG. 4H, and FIG. 4I) Flow cytometry analysis showing expression of CD4, CD8α, KLRG1, CD62L and H-2D$^b$-gp(33-41)-specific TCR in peripheral blood mononuclear cells (PBMC) from Tfap4$^{-/-}$ (n=7), Tfap4$^{F/F}$ CD8-Cre+ (n=7) and control C57BL/6 mice (n=15) on day 8 after LCMV-Arm infection. Statistical analysis is shown in (FIG. 4E, FIG. 4F, FIG. 4G, FIG. 4H, and FIG. 4I). Error bars, s.d. *P<0.05, P<0.01, *P<0.001, NS: not significant by unpaired t-test (FIG. 4B) or one-way ANOVA (FIG. 4E, FIG. 4F, FIG. 4G, FIG. 4H, and FIG. 4I).

(FIG. 5A) Flow cytometry of Tfap4$^{-/-}$ (Thy-1.1− CD45.2) and control WT (Thy-1.1+ CD45.2) P14 T cells 16 hours after co-transfer at a 1:1 ratio into congenic host mice showing expression of Thy-1.1, CD45.2, CD62L and CD44. (n=3). (FIG. 5B) Frequencies of CD8+ T cells in the spleen, mesenteric lymph nodes (MLN), lung, liver, and kidney of Tfap4$^{-/-}$ and control B6 mice under steady-state conditions. (n=5). (FIG. 5C) Flow cytometry of CFSE-labeled Tfap4$^{-/-}$ and WT P14 T cells in host mice three days after LCMV-Arm infection. (n=2). (FIG. 5D) Flow cytometry showing the frequencies of Tfap4$^{-/-}$ and WT P14 donor cells at different time points after LCMV-Arm infection in host mice with a starting ratio of 1:1. (FIG. 5E, FIG. 5F, FIG. 5G) Statistical analysis of numbers of Tfap4$^{-/-}$ and WT P14 cells in the spleen normalized to 10,000 transferred cells (FIG. 5E), ratios between Tfap4$^{-/-}$ and WT P14 T cells (FIG. 5F), and percentages of BrdU+ cells following two hour pulse labeling (FIG. 5G). (n=9-13 for day 3, 8-18 for day 4, 8-13 for day 5, 9-19 for day 6, 4-8 for day 7, 4-9 day 8, 3 for day 10, 5 for day 12). (FIG. 5H, FIG. 5I) Flow cytometry of transferred Tfap4$^{-/-}$ and WT P14 cells and host CD8+CD44+ cells in the spleen six days after LCMV-Arm infection showing AnnexinV (AnnV) binding. Representative plots (FIG. 5H) and statistical analysis from five mice (FIG. 5I) are shown. (FIG. 5J) Relative frequencies of Tfap4$^{-/-}$ and WT P14 donor cells in different organs and blood in host mice seven days after LCMV-Arm infection with a starting ratio of 6:1. (n=8). Error bars, s.d. *P<0.05, P<0.01, *P<0.001 by unpaired t-test. NS: not significant by unpaired t-test (FIG. 5B, FIG. 5E, FIG. 5G) and by one-way ANOVA (FIG. 5J).

FIG. 6A, FIG. 6B, FIG. 6C, FIG. 6D, FIG. 6E, FIG. 6F, FIG. 6G, FIG. 6H, FIG. 6I, FIG. 6J, FIG. 6K, FIG. 6L, FIG. 6M, and FIG. 6N depict flow cytometry plots and graphs showing that AP4 is required for expansion of Ag-specific CD8+ T cells in response to Lm-Ova infection. (FIG. 6A) Flow cytometry analysis showing expression of CD8α, KLRG1, CD62L and H2-K$^b$-Ova-specific TCR in splenocytes of Tfap4$^{-/-}$ and control B6 mice on day 7 after Lm-Ova infection. Ova-specific CD8+ T cells, and KLRG1+ CD62L− effectors and KLRG1− CD62L+ memory precursors are shown with rectangular gates with percentages. (FIG. 6B, FIG. 6C, and FIG. 6D) Statistical analysis of total (FIG. 6B), KLRG1+ (FIG. 6C), and CD62L+ (FIG. 6D) H2-K$^b$-Ova-specific CD8+ T cells. (n=6 for WT, 8 for Tfap4$^{-/-}$ mice in two independent experiments). (FIG. 6E) Statistical analysis of ratios between Tfap4$^{-/-}$ and WT OT-I T cells. (n=15 for day 3, 18 for day 4, 6 for day 5, 8 for day 6, 8 for day 7). (FIG. 6F) Statistical analysis of percentages of BrdU+ OT-I T cells following two hour pulse labeling. (n=9 for day 3, 5 for day 4, 7 for day 5, 6 for day 6, 8 for day 7). (FIG. 6G and FIG. 6H) Flow cytometry analysis of OT-I T cells showing levels of phosphorylated serine 235/236 of S6 ribosomal protein (p-S6) on day 4 after Lm-Ova infection shown as histogram overlays. (n=5). (FIG. 6I) Statistical analysis of ratios of Tfap4$^{-/-}$ and WT OT-I T cells co-cultured with Ova(257-264) peptide-pulsed irradiated splenocytes. Percentages of Tfap4$^{-/-}$ OT-I cells in total OT-I T cells are shown. (FIG. 6J and FIG. 6K) Flow cytometry analysis of Tfap4$^{-/-}$ and WT OT-I T cells showing FSC after co-culture in the presence of irradiated splenocytes pulsed with 0.1 nM of Ova(257-264) peptide. (n=3). (FIG. 6L) Statistical analysis of percentages of IFN-γ-producing Tfap4$^{-/-}$ and WT OT-I cells that had been initially activated by anti-CD3 and anti-CD28 antibodies and re-stimulated with Ova(257-264)-peptide pulsed irradiated splenocytes. Values were normalized to the maximum percentage of cells producing IFN-γ. (n=2). (FIG. 6M and FIG. 6N) Statistical analysis of Lm-Ova bacterial titers in spleens (FIG. 6M) and livers (FIG. 6N) of Tfap4$^{F/F}$ CD8-Cre+ and Tfap4$^{F/F}$ Cre− mice on days 4 and 6 after infection. (n=4 for Tfap4$^{F/F}$ Cre−, 6 for Tfap4$^{F/F}$ CD8-Cre$^+$ in two experiments). Error bars, s.d. *P<0.05,  P<0.01, *P<0.001, NS: not significant by unpaired t-test.

(FIG. 7A) Survival of Tfap4$^{F/F}$ CD8-Cre$^+$ and control Tfap4$^{F/F}$ Cre$^-$ mice following WNV infection. Data from three independent experiments were pooled (n=22 for CD8-Cre$^+$, n=16 for Cre$^-$). *P<0.001 by the log-rank test. (FIG. 7B, FIG. 7C) Viral titers in the brain (FIG. 7B) and spleen (FIG. 7C) from Tfap4$^{F/F}$ CD8-Cre$^+$ and control Tfap4$^{F/F}$ Cre$^-$ mice on day 9 post-WNV infection. Data were pooled from four (FIG. 7B, n=18) or two (FIG. 7C, n=7) independent experiments. Red bars in (FIG. 7B) indicate median values of PFU/gram tissue. **P<0.05, NS: not significant by Mann Whitney U-test.

(FIG. 9A, FIG. 9B, and FIG. 9C) Immunoblot and qRT-PCR analysis showing AP4 and c-Myc expression in CD8$^+$ T cells following a 4OHT treatment and stimulation for 10 or 24 h in vitro. Myc$^{+/+}$: Myc$^{F/+}$ Cre$^-$, Myc$^{+/-}$: Myc$^{F/+}$ CreER$^{T2}$(+), Myc$^{-/-}$:Myc$^{F/F}$ CreER$^{T2}$(+), N: 4OHT-treated WT naive CD8$^+$ T cells. (n=3). (FIG. 9D and FIG. 9E) Flow cytometry of OT-I T cells showing FSC after Lm-Ova infection (b) with statistical analysis (c). (n=8 for day 4, 4 for day 6). (FIG. 9F, FIG. 9G, FIG. 9H, FIG. 9I, FIG. 9J, and FIG. 9K) Flow cytometry analysis of c-Myc-GFP and AP4 expression in OT-I T cells following Lm-Ova infection. c-Myc-GFP levels were determined by subtracting the autofluorescence from the GFP fluorescence ofMyc$^{c\text{-}Myc\text{-}GFP/+}$ OT-I T cells. FSC of WT OT-I T cells is shown as a reference. (n=1 for day 0, 3 for days 1 to 3, 2 for days 4 and 5). (FIG. 9L) Immunoblot showing c-Myc and AP4 expression in OT-I T cells after Lm-Ova infection. Lysates from Tfap4$^{-/-}$ CD8$^+$ T cells were used to show antibody specificity. (n=3). (FIG. 9M) Total RNA content in OT-I T cells four days after Lm-Ova infection. (n=5 for WT, 4 for Tfap4$^{-/-}$). (FIG. 9N) ECAR measurement of CD8$^+$ T cells without stimulation (naive), after 24 h stimulation in vitro, or on days 4 and 6 after Lm-Ova infection. Baseline values (UT) and changes following treatment with oligomycin are shown. (n=6 for naive, 10 for 24 h, 3 for days 4 and 6). (FIG. 9O, FIG. 9P, FIG. 9Q, FIG. 9R, FIG. 9S, and FIG. 9T) qRT-PCR analysis of expression of glycolytic genes in OT-I T cells. Expression levels were normalized against the ERCC-00108 spiked-in control RNA and shown as relative values to WT OT-I T cells (n=2 for day 4 WT and day 6 Tfap4$^{-/-}$, 3 for day 4 Tfap4$^{-/-}$ and day 6 WT). Error bars, s.d. *P<0.05, P<0.01, *P<0.001, NS: not significant by one-way ANOVA (a), paired (c) or unpaired t-test (FIG. 9M, FIG. 9N, FIG. 9O, FIG. 9P, FIG. 9Q, FIG. 9R, FIG. 9S, and FIG. 9T).

(FIG. 10A) Overlaps of direct binding targets of AP4 and cMyc and genes downregulated in Tfap4$^{-/-}$ OT-I T cells. (FIG. 10B) Experimental scheme for rescue of Tfap4$^{-/-}$ OT-I T cells by retroviral (RV) expression of AP4 or Myc. Tfap4$^{-/-}$ OT-I T cells were retrovirally infected with empty, AP4- or cMyc-expressing retrovirus and co-cultured with empty-virus infected WT OT-I cells, followed by culture under threshold conditions for 24 hours. The cell size defects (FIG. 10C) and gene expression related to metabolic activity (FIG. 10D) were similarly restored by expression of AP4 or cMyc.

FIG. 11A, FIG. 11B, FIG. 11C, FIG. 11D, FIG. 11E, FIG. 11F, FIG. 11G, FIG. 11H, FIG. 11I, FIG. 11J, FIG. 11K, FIG. 11L, FIG. 11M, FIG. 11N, and FIG. 11O depict graphs, flow cytometry plots and heat maps showing that AP4 is essential for sustained expression of c-Myc target genes. (FIG. 11A, FIG. 11B, FIG. 11C, FIG. 11D, FIG. 11E, and FIG. 11F) Scatter plots showing normalized signal intensity (NSI) of endogenous transcripts in Tfap4$^{-/-}$ (KO) and WT OT-I T cells on day 4 after Lm-Ova infection (FIG. 11A, FIG. 11B, and FIG. 11C) and ERCC control RNA (FIG. 11D, FIG. 11E, and FIG. 11F). Values of slopes obtained by linear regression (95% CI in parentheses) are shown. The slope of the blue dotted line in each plot is 1. Error bars, 95% CI in (FIG. 11G). (FIG. 11H, FIG. 11I, FIG. 11J, FIG. 11K, and FIG. 11L) Heat maps showing expression of genes in over-represented pathways identified by NIH DAVID ver. 6.7 (n=2). Genes shown in red are bound by both c-Myc and AP4. (FIG. 11M) Expression kinetics of the 479 genes defined in (FIG. 10A) in WT OT-I T cells after Lm-Ova infection. Expression levels were normalized to values in naive CD8$^+$ T cells. (n=2 for naive, days 4 and 6, 3 for day 2). (FIG. 11N) Flow cytometry of Myc$^{c\text{-}mYc\text{-}GFP}$ P14 T cells showing c-Myc-GFP expression after LCMV-Arm infection. (n=4). (FIG. 11O) ChIP-qPCR analysis of AP4 binding to AP4-c-Myc co-targeted genes in P14 T cells on day 5 after LCMV-Arm infection. Data normalized to signals from Tfap4$^{-/-}$ cells. Error bars, s.d. *P<0.05, P<0.01, *P<0.001, NS: not significant by unpaired t-test.

FIG. 12A, FIG. 12B, FIG. 12C, FIG. 12D, FIG. 12E, FIG. 12F, FIG. 12G, FIG. 12H, and FIG. 12I depict graphs and flow cytometry plots showing that sustained c-Myc expression rescues defects of Tfap4$^{-/-}$ CD8 T cells. (FIG. 12A) Flow cytometry of Tfap4$^{-/-}$ OT-I T cells transduced with empty (EV), AP4- or c-Myc(T58A)-expressing RV showing FSC. Co-cultured EV-transduced WT OT-I T cells were used as control. Statistical analysis of FSC ratios between RV-transduced Tfap4$^{-/-}$ and EV-transduced WT OT-I T cells are shown in (FIG. 12B). (n=5). (FIG. 12C, FIG. 12D) ECAR (FIG. 12C) and BrdU incorporation rates (FIG. 12D) of RV-transduced Tfap4$^{-/-}$ and EV-transduced control WT OT-I T cells. (n=3). (FIG. 12E) Flow cytometry showing frequencies of and expression of Thy-1.1, CD44, KLRG1 and CD62L in adoptively co-transferred RV-transduced Tfap4$^{-/-}$ (Thy1.1$^-$) and EV-transduced WT (Thy-1.1$^+$) OT-I T cells on day 6 after Lm-Ova infection. (n=8). (FIG. 12F-FIG. 12I) Statistical analyses of relative frequencies of RV-transduced Tfap4$^{-/-}$ to EV-transduced WT OT-I T cells (KO/WT, FIG. 12F) and percentages of KLRG1$^+$ cells (FIG. 12G), BrdU incorporation rates (FIG. 12H), and FSC ratios between RV-transduced Tfap4$^{-/-}$ and co-transferred EV-transduced WT OT-I T cells (FIG. 12I). (n=8 for FIG. 12F, FIG. 12G, FIG. 12I, 4 for FIG. 12H). Error bars, s.d. *P<0.05, *P<0.01, ***P<0.001 by one-way ANOVA.

(FIG. 13A) ChIP sequencing data showing AP4, but cMyc binding to the Il2ra locus. (FIG. 13B) Microarray data showing reduced Il24a mRNA expression in Tfap4$^{-/-}$ OT-I cells compared to WT OT-I cells on days 4 and 6 after Lm-Ova infection. (FIG. 13C) Reduced CD25 expression in Tfap4$^{-/-}$ OT-I cells compared to WT OT-I cells after Lm-Ova infection. (FIG. 13D) CD25 and Granzyme B expression Tfap4$^{-/-}$ and WT OT-I cells 4 days after Lm-Ova infection.

(FIG. 16A) The Flag-tagged AP4$^{S139A}$ mutant persisted longer than non-mutated control. (FIG. 16B) Retrovirally (RV) expressed Flag-tagged AP4 (S139A) maintains blasting and CD25 expression in the presence of low IL-2. (FIG. 16C) Development and validation of a conditional activation allele expressing AP4 (S139A). Naïve CD8+ T cells from WT and Rosa26$^{LSL-sAP4}$ mice were retrovirally transduced with Cre (ires GFP) and cultures as in (FIG. 16B).

FIG. 17A, FIG. 17B, FIG. 17C, FIG. 17C, FIG. 17D, FIG. 17E, FIG. 17F, FIG. 17G, FIG. 17F, FIG. 17G, FIG. 17H, FIG. 17I, FIG. 17J, FIG. 17K, FIG. 17L, FIG. 17M, FIG. 17N, and FIG. 17O depict graphs and flow cytometry plots showing that AP4 is essential for secondary expansion of memory CD8$^+$ T cells. (FIG. 17A) Flow cytometry analysis of splenocytes showing expression of CD8a, CD127, CD62L and H-2D$^b$-gp(33-41)-specific TCR on day 60 after LCMV-Arm infection. (n=4). (FIG. 17B, FIG. 17C, and FIG. 17D) Statistical analysis of absolute numbers of H-2D$^b$-gp(33-41)-specific total memory CD8$^+$ T cells and CD62L$^+$ central memory CD8$^+$ T cells in the spleen on day 60 after LCMV-Arm infection (FIG. 17B and FIG. 17C) and frequencies of H-2D$^b$-gp(33-41)-specific memory CD8$^+$ T cells in peripheral blood mononuclear cells (PBMC) in Tfap4$^{-/-}$ (n=6), Tfap4$^{F/F}$ CD8-Cre$^+$ (n=7) or control WT mice (n=14) on day 60 after LCMV-Arm infection (FIG. 17D). (FIG. 17E) IFN-γ ELISPOT assay showing frequencies of H-2K$^b$-Ova(257-264)-specific memory CD8$^+$ T cells in splenocytes of Tfap4$^{-/-}$ (n=4) and control WT mice (n=4) on day 45 after Lm-Ova infection. All mice had less than 11 spots per million splenocytes when no antigen was included. (FIG. 17J and FIG. 17K) Flow cytometry analysis of PBMC of Tfap4$^{-/-}$ (n=15), Tfap4$^{F/F}$ CD8-Cre$^+$ (n=9), or control C57BL/6 mice (n=14) 5 days after secondary challenge with Lm-Ova. (FIG. 17L, FIG. 17M, FIG. 17N, and FIG. 17O) Statistical analysis of numbers of total CD8$^+$ T cell and H-2K$^b$-Ova-specific CD8$^+$ T cells numbers in blood and spleen 5 days after secondary challenge with Lm-Ova is shown. Error bars, s.d. *P<0.01, P<0.001, *P<0.0001, NS: not significant by unpaired t-test (FIG. 17B, FIG. 17C, FIG. 17E, FIG. 17H, and FIG. 17I) or one-way ANOVA (FIG. 17D, FIG. 17L, FIG. 17M, FIG. 17N, and FIG. 17O).

FIG. 18 depicts an experimental schematic.

(FIG. 19A) A knock-in strategy of mCherry into the C-terminus of AP4. We have confirmed that stability of AP4 is unaltered by mCherry fusion. We have obtained germline transmission of this allele generated in C57BL6N ES cells. (FIG. 19B) Activation of AP4-mCherry expression in activated CD8$^+$ T cells. (FIG. 19C) Validation of AP4 and AP4-mCherry protein expression in cells from Tfap4$^{mCherry/+}$ mice.

DETAILED DESCRIPTION OF THE INVENTION

Figure 1:
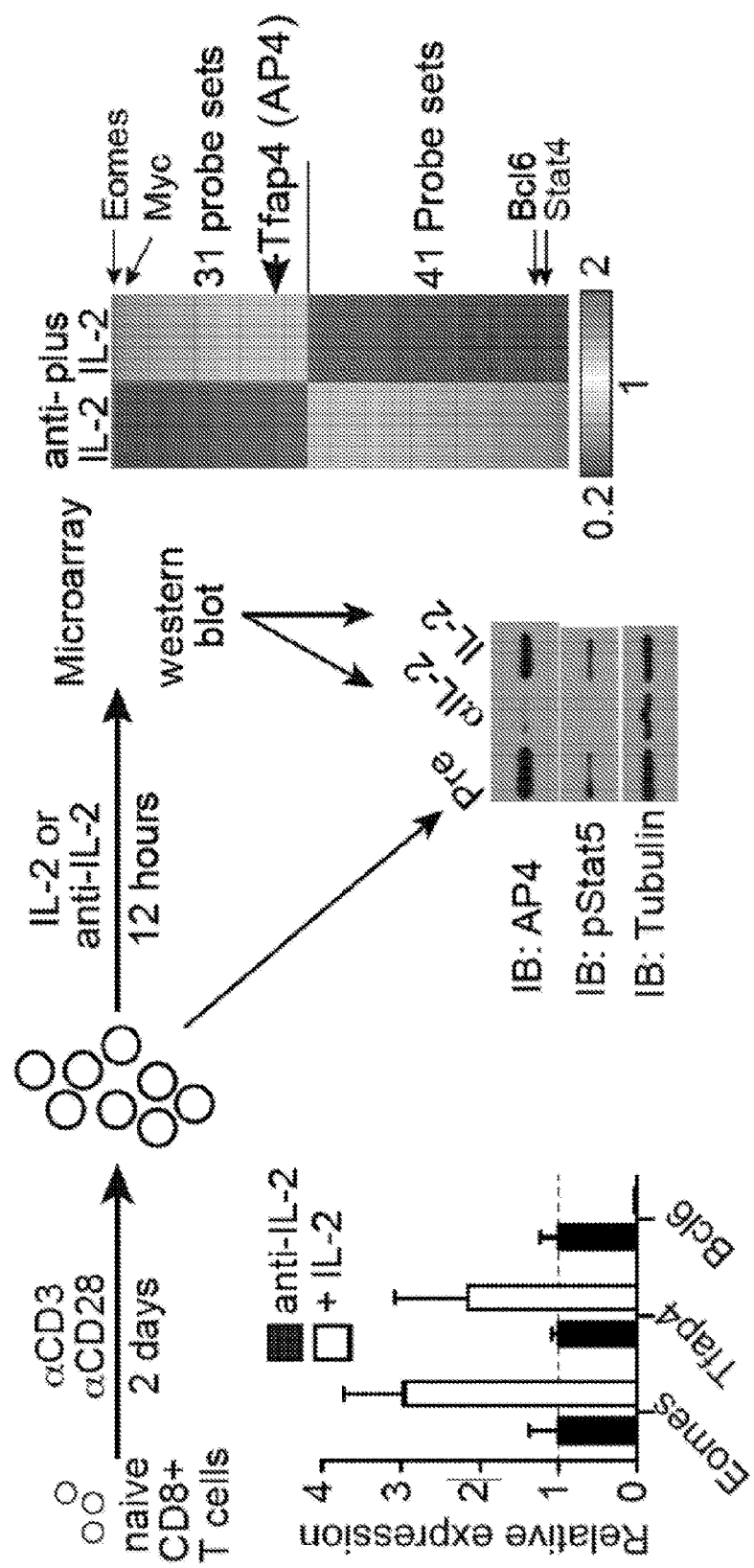
FIG. 1 depicts a schematic, graph, and immunoblot showing that AP4 is induced by IL-2R signals. The top portion depicts the experimental design for microarray analysis to identify IL-2-inducible genes (>2-fold change) in $CD8^+$ T cells and a heatmap showing expression of transcriptional regulators. The bottom graph depicts qRT-PCR validation of microarray analysis, showing rRNA-normalized expression of Eomes, Tfap4 (AP4) and Bcl6 with mean and SD. The immunoblot shows AP4 protein expression in $CD8^+$ T cells requires IL-2R signals in vitro.

Provided herein is data indicating that AP4 is essential for maximum clonal expansion of Ag-specific CD8+ T cells, their effector differentiation, and their protection of hosts from infections by virulent pathogens. However, AP4 is a short-lived protein that is constitutively degraded by the ubiquitin-proteasome pathway. According, the inventors have generated a functionally intact mutant form of AP4 that is resistant to proteasomal degradation. It is shown that expression of this mutant AP4 substantially enhances T cell activation, providing a new strategy for eliminating tumors or chronic viral infections. Further, expression of the mutant AP4 enables activation and differentiation of T cells in the absence of IL-2. Accordingly, provided herein are compositions and methods for enhancing T cell proliferation and function and the use of the modified T cells in adoptive cellular immunotherapy. Various aspects of the compositions and methods are provided in detail below.

I. Composition

In an aspect, the disclosure provides a composition, the composition comprising T cells, wherein the T cells express AP4. Specifically, the composition comprises T cells, wherein the T cells express AP4. The AP4 of the composition comprises a S139 mutation relative to SEQ ID NO: 1 and exhibits increased stability relative to wild-type AP4 and induces T cell proliferation.

(a) AP4

In an aspect, a T cell of the disclosure expresses AP4. As used herein, the term "AP4" includes wild-type AP4, mutant AP4, functional homologs of AP4 and fragments thereof. AP4 facilitates T cell proliferation and expansion and differentiation of CD8+ T cells. Accordingly, an AP4 of the disclosure, including a functional homolog or fragment, facilitates T cell proliferation and expansion and differentiation of CD8+ T cells. Further, AP4 sustains or prolongs CD8+ T cell activation. Accordingly, an AP4 of the disclosure, including a functional homolog or fragment, sustains or prolongs CD8+ T cell activation. Still further, AP4 promotes sustained CD25 expression. Accordingly, an AP4 of the disclosure, including a functional homolog or fragment, promotes sustained CD25 expression. The sequence information for the full length human AP4 amino acid sequence can be found using, for example, the GenBank accession number NP_003214.1, The sequence information for the full length human AP4 mRNA sequence can be found using, for example, the GenBank accession number NM_003223.2. In certain embodiments, an AP4 of the disclosure comprises the sequence set forth in SEQ ID NO:1. In other embodiments, an AP4 of the disclosure may have about 80% identity to SEQ ID NO: 1. For example, an AP4 of the disclosure may have about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identity to SEQ ID NO: 1.

It is appreciated that the present directed is directed to homologs of AP4 in other organisms and is not limited to the human AP4. Non-limiting examples include mouse (NP_112459.1), rat (NP_001101737.1), cattle (NP_001094685.1), frog (NP_001123841.1), dog (XP_547149.2), and cat (XP_006942452.1). Homologs can be found in other species by methods known in the art. In determining whether a protein has significant homology or shares a certain percentage of sequence identity with a sequence of the invention, sequence similarity may be determined by conventional algorithms, which typically allow introduction of a small number of gaps in order to achieve the best fit. In particular, "percent identity" of two polypeptides or two nucleic acid sequences is determined using the algorithm of Karlin and Altschul (*Proc. Natl. Acad. Sci. USA* 87:2264-2268, 1993). Such an algorithm is incorporated into the BLASTN and BLASTX programs of Altschul et al. (*J. Mol. Biol.* 215:403-410, 1990). BLAST nucleotide searches may be performed with the BLASTN program to obtain nucleotide sequences homologous to a nucleic acid molecule of the invention. Equally, BLAST protein searches may be performed with the BLASTX program to obtain amino acid sequences that are homologous to a polypeptide of the invention. To obtain gapped alignments for comparison purposes, Gapped BLAST is utilized as described in Altschul et al. (Nucleic Acids Res. 25:3389-3402, 1997). When utilizing BLAST and Gapped BLAST programs, the default parameters of the respective programs (e.g., BLASTX and BLASTN) are employed. See www.ncbi.nlm.nih.gov for more details.

An AP4 homolog may be at least 65%, 70%, 75%, 80%, 85%, 90%, or 95% homologous to human AP4 provided it has the same functional activity as AP4. In certain embodiments, an AP4 homolog may be at least 65%, 66%, 67%, 68%, 69%, or 70% homologous to human AP4 provided it has the same functional activity as AP4. In different embodiments, an AP4 homolog may be at least 71%, 72%, 73%, 74%, 75%, 76%, 77%, 78%, or 79% homologous to human AP4 provided it has the same functional activity as AP4. In one embodiment, an AP4 homolog may be at least 80%, 81%, 82%, 83%, 84%, 85%, 86%, 87%, 88%, or 89% homologous to human AP4. In another embodiment, an AP4 homolog may be at least 90%, 91%, 92%, 93%, 94%, 95%, 96%, 97%, 98%, 99%, or 100% homologous to AP4. In yet another embodiment, an AP4 homolog may be a truncation or variant that has the same functional activity as the full length AP4.

In an aspect, AP4 of the disclosure may be a fragment of AP4, provided it has the same functional activity as the full length AP4. By "fragment" is meant an amino acid sequence that includes 5 or more consecutive amino acid residues from AP4. "Fragment" refers to both short chains, commonly referred to as peptides, oligopeptides, or oligomers, and to longer chains, up to about 1000 residues in length. A fragment may comprise about 5 or more amino acids. For example, a fragment may comprise about 5 or more, about 10 or more, about 15 or more, about 20 or more, about 25 or more, about 30 or more, about 35 or more, about 40 or more, about 45 or more, about 50 or more, about 55 or more, about 60 or more, about 65 or more, about 70 or more, about 75 or more, about 80 or more, about 85 or more, about 90 or more, about 95 or more, or about 100 or more amino acids. In certain embodiments, a fragment may comprise about 100 or more, about 150 or more, about 200 or more, about 250 or more, or about 300 or more amino acids. In other embodiments, a fragment may comprise from about 100 to about 200 amino acids. In still other embodiments, a fragment may comprise from about 200 to about 300 amino acids. In yet other embodiments, a fragment may comprise from about 300 to about 400 amino acids.

In a specific embodiment, AP4, a homolog of AP4 or a fragment thereof is mutated to increase stability of the protein and promote T cell proliferation. Increased stability may be due to reduced degradation. For example, a mutation is a S139A mutation relative to SEQ ID NO: 1. In a specific embodiment, an AP4 of the disclosure comprises a S139A mutation relative to SEQ ID NO: 1, wherein the mutated AP4 has increased stability and promotes T cell proliferation. In another specific embodiment, an AP4 of the disclosure consists of a S139A mutation relative to SEQ ID NO: 1. In certain embodiments, an AP4 of the disclosure comprises the sequence set forth in SEQ ID NO: 2. In some embodiments, an AP4 of the disclosure consists of the sequence set forth in SEQ ID NO: 2. In other embodiments, an AP4 of the disclosure may have about 80% identity to SEQ ID NO: 2, wherein the AP4 has increased stability and promotes T cell proliferation. For example, an AP4 of the disclosure may have about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identity to SEQ ID NO: 2, wherein the AP4 has increased stability and promotes T cell proliferation. The AP4 may also be a fragment of SEQ ID NO: 2 provided the fragment has increased stability and promotes T cell proliferation.

i. AP4 Construct

In an aspect, the disclosure provides an AP4 construct. An AP4 construct of the disclosure is a polynucleotide sequence encoding a polypeptide comprising AP4. As used herein, the terms "polynucleotide sequence of the disclosure" and "AP4 construct" are interchangeable. The disclosure also provides isolated polypeptides encoded by AP4 constructs, vectors comprising AP4 constructs, and isolated cells comprising said vectors.

An AP4 construct of the disclosure is a polynucleotide sequence encoding a polypeptide comprising AP4. In certain embodiments, the AP4 construct is a polynucleotide sequence encoding at least two polypeptides comprising AP4. When more than one polypeptide is encoded by a polynucleotide of the disclosure, the polynucleotide may comprise more than one promoters operably linked to each polynucleotide encoding a polypeptide. By way of non-limiting example, a polynucleotide encoding a polypeptide comprising a first AP4 may be operably linked to a first promoter and a polynucleotide encoding a polypeptide comprising a second AP4 may be operably linked to a second promoter. The first and second promoter may be the same or different. Promoters are described in more detail below. Alternatively, when more than one polypeptide is encoded by a polynucleotide of the disclosure, the polynucleotide may be operably linked to a single promoter. In such an embodiment, several strategies common in the art may be used to generate more than one expression product. By way of non-limiting example, a splicing signal, internal ribosomal entry site (IRES) or proteolytic cleavage site may be inserted between the polynucleotides encoding the polypeptides. By way of non-limiting example, a polynucleotide encoding a polypeptide comprising a first AP4 and a second AP4 operably linked to a single promoter may further comprise a splicing signal, IRES or proteolytic cleavage site between the coding regions of the first and second AP4.

Polynucleotide sequences of the disclosure may be produced from nucleic acids molecules using molecular biological methods known to in the art. Any of the methods known to one skilled in the art for the amplification of polynucleotide fragments and insertion of polynucleotide fragments into a vector may be used to construct the polynucleotide sequences of the disclosure. These methods may include in vitro recombinant DNA and synthetic techniques and in vivo recombinations (See Sambrook et al. Molecular Cloning, A Laboratory Manual, Cold Spring Harbor Laboratory; Current Protocols in Molecular Biology, Eds. Ausubel, et al., Greene Publ. Assoc., Wiley-Interscience, NY).

In certain aspects, the expression of a polynucleotide sequence of the disclosure may be regulated. Such regulation may allow control over when and where an AP4 construct functions. Expression vectors typically contain one or more of the following elements: promoters, terminators, ribosomal binding sites, and IRES. Such elements may be used to control the expression of an AP4 construct of the disclosure. Expression of the nucleic acid molecules of the invention may be regulated by a second nucleic acid sequence so that the molecule is expressed in a host transformed with the recombinant DNA molecule. For example, expression of the nucleic acid molecules of the disclosure may be controlled by any promoter/enhancer element known in the art. The term "promoter," as used herein, may mean a synthetic or naturally-derived molecule that is capable of conferring, activating or enhancing expression of a nucleic acid. A promoter may be constitutive, inducible/repressible or cell type specific. In certain embodiments, the promoter may be constitutive. Non-limiting examples of constitutive promoters include CMV, UBC, EF1α, SV40, PGK, CAG, CBA/CAGGS/ACTB, CBh, MeCP2, U6, and H1. In other embodiments, the promoter may be an inducible promoter. The inducible promoter may be selected from the group consisting of: tetracycline, heat shock, steroid hormone, heavy metal, phorbol ester, adenovirus E1A element, interferon, and serum inducible promoters. In different embodiments, the promoter may be cell type specific. For example, cell type specific promoters for neurons (e.g., syapsin), astrocytes (e.g., GFAP), oligodendrocytes (e.g., myelin basic protein), microglia (e.g., CX3CR1), neuroendocrine cells (e.g. chromogranin A), muscle cells (e.g., desmin, Mb), cardiomyocytes (e.g., alpha myosin heavy-chain promoter), photoreceptor cells (e.g., Nrl), or haemoglobin beta (HBB) could be used. A promoter may further comprise one or more specific transcriptional regulatory sequences to further enhance expression and/or to alter the spatial expression and/or temporal expression of a nucleic acid. Non-limiting examples of enhancer include the CMV enhancer and the SP1 enhancer.

In an embodiment where more than one polypeptide is encoded by a polynucleotide of the disclosure and the polynucleotide comprises more than one promoters operably linked to each polynucleotide encoding a polypeptide, the promoters may be the same or different. The term "operably linked," as used herein, means that expression of a nucleic acid sequence is under the control of a promoter with which it is spatially connected. A promoter may be positioned 5' (upstream) of the nucleic acid sequence under its control. The distance between the promoter and a nucleic acid sequence to be expressed may be approximately the same as the distance between that promoter and the native nucleic acid sequence it controls. As is known in the art, variation in this distance may be accommodated without loss of promoter function.

(b) T Cells

In an aspect, a T cell of the disclosure expresses AP4. As used herein, a "T cell," which may be used interchangeably with "T lymphocyte," is a type of lymphocyte that plays a central role in cell-mediated immunity. T cells can be distinguished from other lymphocytes, such as B cells and natural killer (NK) cells, by the presence of a T-cell receptor (TCR) on the cell surface. In general, T cells mature in the thymus. There are several types of T cells including: T helper cells ($T_H$ cells), cytotoxic or effector T cells ($T_C$ cells, $T_E$ cells, CTLs, CD8+ T cell), memory T cells ($T_M$ cells), suppressor T cells ($T_{reg}$ cells), natural killer T cells (NKT cells), mucosal associated invariant T cells, and gamma delta T cells (γδ T cells). CD8+ T cells may be identified by $CD62L^+CD44^-CD8^+CD4^-$. In a specific embodiment, the T cells are CD8+ T cells.

T cells for use in a composition of the disclosure may be derived from a publically available cell line. For example, T cells may be obtained from STEMCELL T cell lines such as #70024 or T cells may be derived from the ATCC cell lines PCS-800-011 or PCS-800-013, which are primary mononuclear cell lines. Methods standard in the art may be used to isolate/enrich T cells from a cell line. For example, flow cytometry using cell surface markers may be used to isolate/enrich T cells. Optionally, prior to isolation, T cell growth and differentiation may be stimulated during cell culture with various factors. For example, IL2, IL15, IL7, anti-CD3, and/or anti-CD28 may be utilized to stimulate T cell growth. In a specific embodiment, T cell growth and differentiation may be stimulated during cell culture with anti-CD3 and anti-CD28. Alternatively, T cells for use in a composition of the disclosure may be isolated from a subject. The T cells may be obtained from a single subject, or a plurality of subjects. A plurality refers to at least two (e.g., more than one) subjects. When T cells obtained are from a plurality of subjects, their relationships may be autologous, syngeneic, allogeneic, or xenogeneic. In a specific embodiment, the relationship is allogeneic. In another specific embodiment, the relationship is autologous. Methods of collecting/isolating T cells from a subject are standard in the art. For example, several kits are commercially available to isolate T cells from whole blood or peripheral blood mononuclear cells (PBMCs). Additionally, flow cytometry using cell surface markers may be used to isolate/enrich T cells.

Isolation of T cells may result in a substantially pure population of T cells. The term "substantially pure," may be used herein to describe a purified population of T cells that is enriched for T cells, but wherein the population of T cells are not necessarily in a pure form. Accordingly, a "substantially pure T cell population" refers to a population of T cells that is at least about 50%, preferably at least about 75-80%, more preferably at least about 85-90%, and most preferably at least about 95% of the cells making up the total cell population. Thus, a "substantially pure T cell population" refers to a population of T cells that contain fewer than about 50%, preferably fewer than about 20-25%, more preferably fewer than about 10-15%, and most preferably fewer than about 5% of cells that are not T cells.

Following isolation of T cells, the T cells may be cultured in the presence of a basal medium. The basal medium may contain a mixture of additional factors such as cytokines and growth factors. The additional factors may promote T cell growth and differentiation. In one embodiment, the basal medium includes amino acids, carbon sources (e.g., pyruvate, glucose, etc.), vitamins, serum proteins (e.g., albumin), inorganic salts, divalent cations, antibiotics, buffers, and other preferably defined components that support growth of T cells. Suitable basal mediums include, without limitation, RPMI medium, Iscove's medium, minimum essential medium, Dulbecco's Modified Eagles Medium, and others known in the art. The basal medium may comprise fetal bovine serum. The formulations of these and other mediums will be apparent to the skilled artisan. In certain embodiment, the T cells may be cultured to promote T cell (TCR) stimulation. Methods of culturing T cells to promote T cell stimulation are standard in the art. For example, IL2, anti-CD3 and/or anti-CD28 may be utilized to promote TCR stimulation. As such, the T cells may be cultured in the presence of IL2+/−anti-CD3 and/or anti-CD28 to promote T cell (TCR) stimulation. Alternatively, the T cells may be cultured in a manner so as to not promote TCR stimulation. For example, the T cells may be cultured in the presence of IL7, IL15, and/or anti-IL2.

The T cells may be cultured in the presence of a basal medium with or without TCR stimulation for 12 or more hours. Accordingly, T cells may be cultured in the presence of a basal medium with or without TCR stimulation for about 12, about 14, about 16, about 18, about 20, about 22, or about 24 hours. Additionally, T cells may be cultured in the presence of a basal medium with or without TCR stimulation for about 1, about 2, about 3, about 4, about 5, about 6, about 7, about 8, about 9, about 10, about 11, about 12, about 13, or about 14 days. In certain embodiments, T cells may be cultured in the presence of a basal medium with or without TCR stimulation for about 1 to about 5 days. In another embodiment, T cells may be cultured in the presence of a basal medium with or without TCR stimulation for about 3 days.

Following culture, the T cells are transfected with a vector comprising an AP4 construct of the disclosure. An AP4 construct is as described in Section 1(a)i. As used herein, a vector is defined as a nucleic acid molecule used as a vehicle to transfer genetic material. Vectors include but are not limited to, plasmids, phasmids, cosmids, transposable elements, viruses (e.g., bacteriophage, animal viruses, and plant viruses), and artificial chromosomes (e.g., YACs), such as retroviral vectors (e.g., derived from Moloney murine leukemia virus vectors (e.g., MoMLV, MSCV, SFFV, MPSV, SNV, etc), lentiviral vectors (e.g., derived from HIV-1, HIV-2, SIV, BIV, FIV, etc.), adenoviral (Ad) vectors including replication competent, replication deficient and gutless forms thereof, adeno-associated viral (AAV) vectors, simian virus 40 (SV-40) vectors, bovine papilloma virus vectors, Epstein-Barr virus, herpes virus vectors, vaccinia virus vectors, Harvey murine sarcoma virus vectors, murine mammary tumor virus vectors, and Rous sarcoma virus vectors.

A vector encoding an AP4 construct may be delivered to the cell using a viral vector or via a non-viral method of transfer. Viral vectors suitable for introducing nucleic acids into cells include retroviruses, adenoviruses, adeno-associated viruses, rhabdoviruses, and herpes viruses. Non-viral methods of nucleic acid transfer include naked nucleic acid, liposomes, and protein/nucleic acid conjugates. A vector encoding an AP4 construct that is introduced to the cell may be linear or circular, may be single-stranded or double-stranded, and may be DNA, RNA, or any modification or combination thereof.

A vector encoding an AP4 construct may be introduced into the cell by transfection. Methods for transfecting nucleic acids are well known to persons skilled in the art. Transfection methods include, but are not limited to, viral transduction, cationic transfection, liposome transfection, dendrimer transfection, electroporation, heat shock, nucleofection transfection, magnetofection, nanoparticles, biolistic particle delivery (gene gun), and proprietary transfection reagents such as LIPOFECTAMINE, DOJINDO HILYMAX, FUGENE, JETPEI, EFFECTENE, or DREAMFECT.

Upon introduction into the cell, a vector encoding an AP4 construct may be integrated into a chromosome. In some embodiments, integration of the vector encoding an AP4 construct into a cellular chromosome may be achieved with a mobile element. The mobile element may be a transposon or a retroelement. A variety of transposons are suitable for use in the disclosure. Examples of DNA transposons that may be used include the Mu transposon, the P element transposons from *Drosophila*, and members of the Tc1/Mariner superfamily of transposons such as the sleeping beauty transposon from fish. A variety of retroelements are suitable for use in the disclosure and include LTR-containing retrotransposons and non-LTR retrotransposons. Non-limiting examples of retrotransposons include Copia and gypsy from *Drosophila melanogaster*, the Ty elements from *Saccharomyces cerevisiae*, the long interspersed elements (LINEs), and the short interspersed elements (SINEs) from eukaryotes. Suitable examples of LINEs include L1 from mammals and R2Bm from silkworm.

Integration of the exogenous nucleic acid into a cellular chromosome may also be mediated by a virus. Viruses that integrate nucleic acids into a chromosome include retroviruses. In a specific embodiment, the AP4 construct is introduced into the cell via retroviral transduction. The efficient and precise integration machinery of naturally occurring retroviruses is utilized to produce either a single copy or a few copies of the viral genome stably integrated into a host cell chromosome. Retroviral vectors are useful in achieving stable and efficient transduction of the AP4 construct into cells. Methods of retroviral transduction are known in the art. For example, see Cepko and Pear, *Current Protocols in Molecular Biology* (1996) 9.9.1-9.9.16, the disclosure of which is hereby incorporated by reference in its entirety. A variety of retroviruses are suitable for use in the disclosure. Retroviral vectors may either be replication-competent or replication-defective. The retroviral vector may be a murine stem cell virus, an alpharetrovirus, a betaretrovirus, a gammaretrovirus, a deltaretrovirus, an epsilonretrovirus, a lentivirus, or a spumaretrovirus. In an embodiment, the retroviral vector may be a lentiviral vector. The lentiviral vector may be derived from human, simian, feline, equine, bovine, or lentiviruses that infect other mammalian species. Non-limiting examples of suitable lentiviruses includes human immunodeficiency virus (HIV), simian immunodeficiency virus (SIV), feline immunodeficiency virus (FIV), bovine immunodeficiency virus (BIV), and equine infectious anemia virus (EIAV).

A selectable marker may be included on the AP4 construct to select for cells that stably express AP4. A selectable marker may be used to efficiently select and identify cells that have integrated the AP4 construct. Selectable markers give the cell receiving the AP4 construct a selection advantage, such as resistance towards a certain toxin or antibiotic. Suitable examples of antibiotic resistance markers include, but are not limited to, those coding for proteins that impart resistance to kanamycin, spectomycin, neomycin, gentamycin (G418), ampicillin, tetracycline, chloramphenicol, puromycin, hygromycin, zeocin, and blasticidin.

A vector may also comprise a transcription cassette for expressing reporter proteins. By way of example, reporter proteins may include a fluorescent protein, luciferase, alkaline phosphatase, beta-galactosidase, beta-lactamase, horseradish peroxidase, and variants thereof.

A vector may also comprise a suicide gene. A suitable suicide gene would facilitate the killing of transduced cells upon addition of an agent that activates the suicide gene. For example, a suicide gene may be a herpes simplex virus-derived thymidine kinase. Upon administration of Gancyclovir, the cells expressing the thymidine kinase are eliminated.

Following transfection with a vector comprising an AP4 construct of the disclosure, the T cells may be cultured in the presence of a basal medium. The basal medium may the same or different as that used to culture the T cells prior to transfection. The basal medium may contain a mixture of additional factors such as cytokines and growth factors. The additional factors may promote T cell growth and differentiation. In one embodiment, the basal medium includes amino acids, carbon sources (e.g., pyruvate, glucose, etc.), vitamins, serum proteins (e.g., albumin), inorganic salts, divalent cations, antibiotics, buffers, and other preferably defined components that support growth of T cells. Suitable basal mediums include, without limitation, RPMI medium, Iscove's medium, minimum essential medium, Dulbecco's Modified Eagles Medium, and others known in the art. The basal medium may comprise fetal bovine serum. The formulations of these and other mediums will be apparent to the skilled artisan. The T cells are cultured to promote T cell (TCR) stimulation. Methods of culturing T cells to promote T cell stimulation are standard in the art. For example, IL2, anti-CD3 and/or anti-CD28 may be utilized to promote TCR stimulation. As such, the T cells are cultured in the presence of IL2+/−anti-CD3 and/or anti-CD28 to promote T cell (TCR) stimulation.

The transfected T cells may be cultured in the presence of a basal medium for 12 or more hours. Accordingly, transfected T cells may be cultured in the presence of a basal medium for about 12, about 14, about 16, about 18, about 20, about 22, or about 24 hours. Additionally, transfected T cells may be cultured in the presence of a basal medium for about 1, about 2, about 3, about 4, about 5, about 6, about 7, about 8, about 9, about 10, about 11, about 12, about 13, or about 14 days. In certain embodiments, transfected T cells may be cultured in the presence of a basal medium for about 1 to about 5 days. In another embodiment, transfected T cells may be cultured in the presence of a basal medium for about 3 days.

Additionally, the basal medium may contain antigen. The antigen may be included to generate antigen-specific T cells. For example, a tumor-associated antigen or a viral antigen may be used to generate antigen-specific T cells. A skilled artisan would be able to select the antigen based on the desired disease or disorder to be treated. In certain embodiments, when antigen is present T cells should be co-cultured with autologous dendritic cells derived from bone marrow cells or blood-derived monocytes and irradiated tumor cells. If the basal medium contains tumor-associated antigens, the tumor-associated antigen may be added prior to transduction of the vector comprising an AP4 of the disclosure, after transduction of the vector comprising an AP4 of the disclosure, or both before and after transduction of the vector comprising an AP4 of the disclosure.

The T cells may be used directly or may be frozen for use at a later date. A variety of mediums and protocols for freezing cells are known in the art. Generally, the freezing medium comprises 5-10% dimethyl sulfoxide (DMSO), 10-50% serum, and 50-90% culture medium.

i. Therapeutic Composition

Following culture, the T cells may be combined with pharmaceutical carriers/excipients known in the art to enhance preservation and maintenance of the cells prior to administration. Accordingly, the T cells may be formulated into a therapeutic composition. As such, the invention encompasses a therapeutic composition comprising ex vivo T cells, wherein the T cells express AP4 of the disclosure.

In an aspect, a method of preparing a therapeutic composition for administration to a subject comprises transducing isolated T cells to express AP4 of the disclosure and resuspending the T cells in a pharmaceutically acceptable medium suitable for administration to a recipient subject.

Pharmaceutically acceptable mediums suitable for administration to a subject are known in the art. In some embodiments, cell compositions of the invention can be conveniently provided as sterile liquid preparations, e.g., isotonic aqueous solutions, suspensions, emulsions, dispersions, or viscous compositions, which may be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyol (e.g., glycerol, propylene, glycol, liquid polyethylene glycol, and the like) and suitable mixtures thereof.

Sterile injectable solutions can be prepared by incorporating the T cells of the present disclosure in the required amount of the appropriate solvent with various amounts of the other ingredients, as desired. Such compositions may be in admixture with a suitable carrier, diluent, or excipient such as sterile water, physiological saline, glucose, dextrose, or the like. The compositions can also be lyophilized. The compositions can contain auxiliary substances such as wetting, dispersing, or emulsifying agents (e.g., methylcellulose), pH buffering agents, gelling or viscosity enhancing additives, preservatives, flavoring agents, colors, and the like, depending upon the route of administration and the preparation desired. Standard texts, such as "Remington's Pharmaceutical Science," 17th edition, 1985, incorporated herein by reference, may be consulted to prepare suitable preparations, without undue experimentation.

Various additives which enhance the stability and sterility of the compositions, including antimicrobial preservatives, antioxidants, chelating agents, and buffers, may be added. Prevention of the action of microorganisms can be ensured by various antibacterial and antifungal agents, for example, parabens, chlorobutanol, phenol, sorbic acid, and the like. The compositions can be isotonic, i.e., they can have the same osmotic pressure as blood and lacrimal fluid. The desired isotonicity of the compositions of this invention may be accomplished using sodium chloride, or other pharmaceutically acceptable agents such as dextrose, boric acid, sodium tartrate, propylene glycol or other inorganic or organic solutes. Sodium chloride is preferred particularly for buffers containing sodium ions.

In another aspect, the T cells are cryopreserved in a cryopreservation medium. The T cells may be cryopreserved prior to resuspending in a pharmaceutically acceptable medium. Alternatively, the starting cell population of T cells may be cryopreserved prior to transducing with AP4 of the disclosure. A variety of mediums and protocols for freezing cells are known in the art. Generally, the freezing medium comprises 5-10% dimethyl sulfoxide (DMSO), 10-50% serum, and 50-90% culture medium. Preferably, the freezing medium comprises 5-10% DMSO, 10-20% serum, and 70-85% culture medium. Other additives useful for preserving cells include, by way of example and not limitation, disaccharides such as trehalose (Scheinkonig, C. et al., *Bone Marrow Transplant.* 34(6):531-6 (2004)), or a plasma volume expander, such as hetastarch (i.e., hydroxyethyl starch). In some embodiments, isotonic buffer solutions, such as phosphate-buffered saline, may be used. An exemplary cryopreservative composition has cell-culture medium with 4% HSA, 7.5% DMSO, and 2% hetastarch. Other compositions and methods for cryopreservation are well known and described in the art (see, e.g., Broxmeyer, H. E. et al., *Proc. Natl. Acad. Sci. USA* 100(2). 645-650 (2003)). Cells are preserved at a final temperature of less than about −135° C.

II. Methods

In an aspect, the disclosure provides a method to increase and prolong the expression of AP4 in CD8+ T cells, the method comprising transfecting CD8+ T cells with a vector comprising a polynucleotide sequence encoding a polypeptide comprising AP4, wherein the AP4 comprises a S139A mutation relative to SEQ ID NO: 1 and exhibits increased stability relative to wild-type AP4 and induced T cell proliferation.

In another aspect, the disclosure provides a method to increase CD8+ T cell clonal expansion and effector differentiation, the method comprising transfecting CD8+ T cells with a vector comprising a polynucleotide sequence encoding a polypeptide comprising AP4, wherein the AP4 comprises a S139A mutation relative to SEQ ID NO: 1 and exhibits increased stability relative to wild-type AP4 and induced T cell proliferation. Importantly, due to the presence of AP4, clonal expansion and effector differentiation occurs in the absence of IL-2.

In still another aspect, the disclosure provides a method to enhance anti-tumor CD8+ T cell function, the method comprising transfecting CD8+ T cells with a vector comprising a polynucleotide sequence encoding a polypeptide comprising AP4, wherein the AP4 comprises a S139A mutation relative to SEQ ID NO: 1 and exhibits increased stability relative to wild-type AP4 and induced T cell proliferation.

In still yet another aspect, the disclosure provides a method to improve adoptive cellular immunotherapy in a subject. The method comprises administering to a subject a therapeutic composition comprising isolated T cells expressing AP4 of the disclosure. As used herein, "adoptive cellular immunotherapy," also referred to as "ACI," is a T cell based immunotherapy whereby T cells are taken from a subject and stimulated and/or genetically manipulated. Following population expansion, the T cells are then transferred back into the subject. Accordingly, the methods of the disclosure may be used to treat a disease or disorder in which it is desirable to increase the number of T cells. For example, cancer and chronic viral infections. Regarding viral infections, ACI of virus-specific T cells of the disclosure may restore virus-specific immunity in a subject to prevent or treat viral diseases. Accordingly, virus-specific T cells of the disclosure may be used to reconstitute antiviral immunity after transplantation and/or to treat active viral infections. In a specific embodiment, a subject receiving T cells of the disclosure for treatment or prevention of a viral infection may be immunodeficient.

In a different aspect, the disclosure provides a method to reduce tumor growth in a subject. The method comprises administering to the subject a therapeutic composition comprising isolated T cells expressing AP4 of the disclosure. The inventors have shown that expressing AP4 in CD8+ T cells enhances clonal expansion and differentiation of CD8+ T cells and sustains proliferation. Accordingly, a composition comprising isolated T cells of the disclosure may be used in treating, stabilizing, or preventing cancer and associated diseases in a subject. By "treating, stabilizing, or preventing cancer" is meant causing a reduction in the size of a tumor or in the number of cancer cells, slowing or preventing an increase in the size of a tumor or cancer cell proliferation, increasing the disease-free survival time between the disappearance of a tumor or other cancer and its reappearance, preventing an initial or subsequent occurrence of a tumor or other cancer, or reducing an adverse symptom associated with a tumor or other cancer. In a desired embodiment, the percent of tumor or cancerous cells surviving the treatment is at least 20, 40, 60, 80, or 100% lower than the initial number of tumor or cancerous cells, as measured using any standard assay (e.g., caspase assays, TUNEL and DNA fragmentation assays, cell permeability assays, and Annexin V assays). Desirably, the decrease in the number of tumor or cancerous cells induced by administration of a T cell of the disclosure is at least 2, 5, 10, 20, or 50-fold greater than the decrease in the number of non-tumor or non-cancerous cells. Desirably, the methods of the present invention result in a decrease of 20, 30, 40, 50, 60, 70, 80, 90, or 100% in the size of a tumor or in the number of cancerous cells, as determined using standard methods. Desirably, at least 20, 40, 60, 80, 90, or 95% of the treated subjects have a complete remission in which all evidence of the tumor or cancer disappears. Desirably, the tumor or cancer does not reappear or reappears after at least 5, 10, 15, or 20 years.

In some aspects, the methods described hereinabove may comprises administering AP4 that comprises the sequence set forth in SEQ ID NO: 2. In some embodiments, the AP4 may consist of the sequence set forth in SEQ ID NO: 2. In other embodiments, the AP4 may have about 80% identity to SEQ ID NO: 2, wherein the AP4 has increased stability and promotes T cell proliferation. For example, an AP4 of the disclosure may have about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identity to SEQ ID NO: 2, wherein the AP4 has increased stability and promotes T cell proliferation. The AP4 may also be a fragment of SEQ ID NO: 2 provided the fragment has increased stability and promotes T cell proliferation.

As used herein, "subject" or "patient" is used interchangeably. Suitable subjects include, but are not limited to, a human, a livestock animal, a companion animal, a lab animal, and a zoological animal. In one embodiment, the subject may be a rodent, e.g. a mouse, a rat, a guinea pig, etc. In another embodiment, the subject may be a livestock animal. Non-limiting examples of suitable livestock animals may include pigs, cows, horses, goats, sheep, llamas and alpacas. In yet another embodiment, the subject may be a companion animal. Non-limiting examples of companion animals may include pets such as dogs, cats, rabbits, and birds. In yet another embodiment, the subject may be a zoological animal. As used herein, a "zoological animal" refers to an animal that may be found in a zoo. Such animals may include non-human primates, large cats, wolves, and bears. In specific embodiments, the animal is a laboratory animal. Non-limiting examples of a laboratory animal may include rodents, canines, felines, and non-human primates. In certain embodiments, the animal is a rodent. Non-limiting examples of rodents may include mice, rats, guinea pigs, etc. In a preferred embodiment, the subject is human.

(a) Tumor

T cells of the disclosure may be used to treat a tumor derived from a neoplasm or a cancer. "Neoplasm" is any tissue, or cell thereof, characterized by abnormal growth as a result of excessive cell division. The neoplasm may be malignant or benign, the cancer may be primary or metastatic; the neoplasm or cancer may be early stage or late stage. Non-limiting examples of neoplasms or cancers that may be treated or detected include acute lymphoblastic leukemia, acute myeloid leukemia, adrenocortical carcinoma, AIDS-related cancers, AIDS-related lymphoma, anal cancer, appendix cancer, astrocytomas (childhood cerebellar or cerebral), basal cell carcinoma, bile duct cancer, bladder cancer, bone cancer, brainstem glioma, brain tumors (cerebellar astrocytoma, cerebral astrocytoma/malignant glioma, ependymoma, medulloblastoma, supratentorial primitive neuroectodermal tumors, visual pathway and hypothalamic gliomas), breast cancer, bronchial adenomas/carcinoids, Burkitt lymphoma, carcinoid tumors (childhood, gastrointestinal), carcinoma of unknown primary, central nervous system lymphoma (primary), cerebellar astrocytoma, cerebral astrocytoma/malignant glioma, cervical cancer, childhood cancers, chronic lymphocytic leukemia, chronic myelogenous leukemia, chronic myeloproliferative disorders, colon cancer, cutaneous T-cell lymphoma, desmoplastic small round cell tumor, endometrial cancer, ependymoma, esophageal cancer, Ewing's sarcoma in the Ewing family of tumors, extracranial germ cell tumor (childhood), extragonadal germ cell tumor, extrahepatic bile duct cancer, eye cancers (intraocular melanoma, retinoblastoma), gallbladder cancer, gastric (stomach) cancer, gastrointestinal carcinoid tumor, gastrointestinal stromal tumor, germ cell tumors (childhood extracranial, extragonadal, ovarian), gestational trophoblastic tumor, gliomas (adult, childhood brain stem, childhood cerebral astrocytoma, childhood visual pathway and hypothalamic), gastric carcinoid, hairy cell leukemia, head and neck cancer, hepatocellular (liver) cancer, Hodgkin lymphoma, hypopharyngeal cancer, hypothalamic and visual pathway glioma (childhood), intraocular melanoma, islet cell carcinoma, Kaposi sarcoma, kidney cancer (renal cell cancer), laryngeal cancer, leukemias (acute lymphoblastic, acute myeloid, chronic lymphocytic, chronic myelogenous, hairy cell), lip and oral cavity cancer, liver cancer (primary), lung cancers (non-small cell, small cell), lymphomas (AIDS-related, Burkitt, cutaneous T-cell, Hodgkin, non-Hodgkin, primary central nervous system), macroglobulinemia (Waldenström), malignant fibrous histiocytoma of bone/osteosarcoma, medulloblastoma (childhood), melanoma, intraocular melanoma, Merkel cell carcinoma, mesotheliomas (adult malignant, childhood), metastatic squamous neck cancer with occult primary, mouth cancer, multiple endocrine neoplasia syndrome (childhood), multiple myeloma/plasma cell neoplasm, mycosis fungoides, myelodysplastic syndromes, myelodysplastic/myeloproliferative diseases, myelogenous leukemia (chronic), myeloid leukemias (adult acute, childhood acute), multiple myeloma, myeloproliferative disorders (chronic), nasal cavity and paranasal sinus cancer, nasopharyngeal carcinoma, neuroblastoma, non-Hodgkin lymphoma, non-small cell lung cancer, oral cancer, oropharyngeal cancer, osteosarcoma/malignant fibrous histiocytoma of bone, ovarian cancer, ovarian epithelial cancer (surface epithelial-stromal tumor), ovarian germ cell tumor, ovarian low malignant potential tumor, pancreatic cancer, pancreatic cancer (islet cell), paranasal sinus and nasal cavity cancer, parathyroid cancer, penile cancer, pharyngeal cancer, pheochromocytoma, pineal astrocytoma, pineal germinoma, pineoblastoma and supratentorial primitive neuroectodermal tumors (childhood), pituitary adenoma, plasma cell neoplasia, pleuropulmonary blastoma, primary central nervous system lymphoma, prostate cancer, rectal cancer, renal cell carcinoma (kidney cancer), renal pelvis and ureter transitional cell cancer, retinoblastoma, rhabdomyosarcoma (childhood), salivary gland cancer, sarcoma (Ewing family of tumors, Kaposi, soft tissue, uterine), Sezary syndrome, skin cancers (nonmelanoma, melanoma), skin carcinoma (Merkel cell), small cell lung cancer, small intestine cancer, soft tissue sarcoma, squamous cell carcinoma, squamous neck cancer with occult primary (metastatic), stomach cancer, supratentorial primitive neuroectodermal tumor (childhood), T-Cell lymphoma (cutaneous), testicular cancer, throat cancer, thymoma (childhood), thymoma and thymic carcinoma, thyroid cancer, thyroid cancer (childhood), transitional cell cancer of the renal pelvis and ureter, trophoblastic tumor (gestational), enknown primary site (adult, childhood), ureter and renal pelvis transitional cell cancer, urethral cancer, uterine cancer (endometrial), uterine sarcoma, vaginal cancer, visual pathway and hypothalamic glioma (childhood), vulvar cancer, WaldenstrOm macroglobulinemia, and Wilms tumor (childhood).

(b) Administration

T cells of the disclosure may be administered to a subject according to methods known in the art. Such compositions may be administered by any conventional route, including injection or by gradual infusion over time. Administration is performed using standard effective techniques, including peripherally (i.e., not by administration into the central nervous system) or locally to the central nervous system. Peripheral administration includes but is not limited to intravenous, intraperitoneal, subcutaneous, pulmonary, transdermal, intramuscular, intranasal, buccal, sublingual, or suppository administration. Local administration, including directly into the central nervous system (CNS), includes but is not limited to via a lumbar, intraventricular or intraparenchymal catheter or using a surgically implanted controlled release formulation.

The T cells are administered in "effective amounts," or the amounts that either alone or together with further doses produce the desired therapeutic response (e.g., an immunostimulatory, a cytotoxic response, tumor regression, infection reduction). Actual amount of T cells in a therapeutic composition of the disclosure can be varied so as to administer an amount of T cells that is effective to achieve the desired therapeutic response for a particular subject. The selected amount will depend upon a variety of factors including the activity of the therapeutic composition, formulation, the route of administration, combination with other drugs or treatments, tumor size and longevity, the viral infection, and the physical condition and prior medical history of the subject being treated. In some embodiments, a minimal dose is administered, and dose is escalated in the absence of dose-limiting toxicity. Determination and adjustment of a therapeutically effective dose, as well as evaluation of when and how to make such adjustments, are known to those of ordinary skill in the art of medicine. In an aspect, a typical dose contains from about $1\times10^2$ to about $1\times10^8$ T cells of the disclosure. In an embodiment, a typical dose contains from about $1\times10^2$ to about $1\times10^4$ T cells of the disclosure. In another embodiment, a typical dose contains from about $1\times10^3$ to about $1\times10^5$ T cells of the disclosure. In still another embodiment, a typical dose contains from about $1\times10^4$ to about $1\times10^6$ T cells of the disclosure. In still yet another embodiment, a typical dose contains from about $1\times10^5$ to about $1\times10^7$ T cells of the disclosure. In certain embodiments, a typical dose contains from about $1\times10^6$ to about $1\times10^8$ T cells of the disclosure. In a different embodiment a typical dose contains about $1\times10^5$, about $5\times10^5$, about $1\times10^6$, about $5\times10^6$, about $1\times10^7$, or about $5\times10^7$ T cells of the disclosure.

Administered cells of the disclosure may be autologous ("self") or heterologous/non-autologous ("non-self," e.g., allogeneic, syngeneic or xenogeneic). Generally, administration of the cells can occur within a short period of time following the culturing of the T cells (e.g., 1, 2, 5, 10, 24, 48 hours, 1 week, or 2 weeks after culturing) and according to the requirements of each desired treatment regimen.

Administered T cells of the disclosure may be present in the recipient subject at 1 day or more following administration. For example, T cells of the disclosure may be present at 1, 2, 3, 4, 5, 6, 7, 8, 9, 10, 11, or 12 days or more following administration. Additionally, T cells of the disclosure may be present at 1, 2, 3, 4, 5, 6, 7, 8, 9, 10, 11, or 12 weeks or more following administration. Further, T cells of the disclosure may be present at 1, 2, 3, 4, 5, 6, 7, 8, 9, 10, 11, or 12 months or more following administration. Administered T cells may be present as donor-derived T cells. Methods of detecting the presence of donor-derived T cells are known in the art and may include flow cytometry.

The frequency of dosing may be once, twice, three times or more daily or once, twice, three times or more per week or per month, as needed as to effectively treat the symptoms or disease. In certain embodiments, the frequency of dosing may be once, twice or three times daily. For example, a dose may be administered every 24 hours, every 12 hours, or every 8 hours. In other embodiments, the frequency of dosing may be once, twice, or three times weekly. For example, a dose may be administered every 2 days, every 3 days, or every 4 days. In a different embodiment, the frequency of dosing may be one, twice, three or four times monthly. For example, a dose may be administered every 1 week, every 2 weeks, every 3 weeks, or every 4 weeks.

Duration of treatment could range from a single dose administered on a one-time basis to a life-long course of therapeutic treatments. The duration of treatment can and will vary depending on the subject and the cancer or infection to be treated. For example, the duration of treatment may be for 1 day, 2 days, 3 days, 4 days, 5 days, 6 days, or 7 days. Or, the duration of treatment may be for 1 week, 2 weeks, 3 weeks, 4 weeks, 5 weeks, or 6 weeks. Alternatively, the duration of treatment may be for 1 month, 2 months, 3 months, 4 months, 5 months, 6 months, 7 months, 8 months, 9 months, 10 months, 11 months, or 12 months. In still another embodiment, the duration of treatment may be for 1 year, 2 years, 3 years, 4 years, 5 years, or greater than 5 years. It is also contemplated that administration may be frequent for a period of time and then administration may be spaced out for a period of time. For example, duration of treatment may be 5 days, then no treatment for 9 days, then treatment for 5 days.

The pharmaceutical composition of the present invention is administered in a manner compatible with the dosage formulation, and in a therapeutically effective amount, for example intravenously, intraperitoneally, intramuscularly, subcutaneously, and intradermally. It may also be administered by any of the other numerous techniques known to those of skill in the art, see for example the latest edition of Remington's Pharmaceutical Science, the entire teachings of which are incorporated herein by reference. For example, for injections, the pharmaceutical composition of the present invention may be formulated in adequate solutions including but not limited to physiologically compatible buffers such as Hank's solution, Ringer's solution, or a physiological saline buffer. The solutions may contain formulatory agents such as suspending, stabilizing, and/or dispersing agents. Alternatively, the pharmaceutical composition of the present invention may be in powder form for combination with a suitable vehicle, e.g., sterile pyrogen free water, before use. Further, the composition of the present invention may be administered per se or may be applied as an appropriate formulation together with pharmaceutically acceptable carriers, diluents, or excipients that are well known in the art. In addition, other pharmaceutical delivery systems such as liposomes and emulsions that are well known in the art, and a sustained-release system, such as semi-permeable matrices of solid polymers containing a therapeutic agent, may be employed. Various sustained-release materials have been established and are well-known to one skilled in the art. Further, the composition of the present disclosure can be administered alone or together with another therapy conventionally used for the treatment of a disease/condition in which it is desirable to increase the number of T cells.

The method may further comprise administration of agents standard in the art for treating cancer. Such agents may depend on the type and severity of the cancer, as well as the general condition of the patient. Agents for the treatment of cancer consist primarily of radiation, surgery, chemotherapy and/or targeted therapy. Standard treatment algorithms for each cancer may be found via the National Comprehensive Cancer Network (NCCN) guidelines (www.nccn.org/professionals/physician_gls/f_guidelines.asp). Additionally, the method may further comprise administration of agents standard in the art for treating viral infection.

EXAMPLES

The following examples are included to demonstrate various embodiments of the present disclosure. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1. AP4 is an IL-2-Inducible Transcription Factor

Figure 2A:
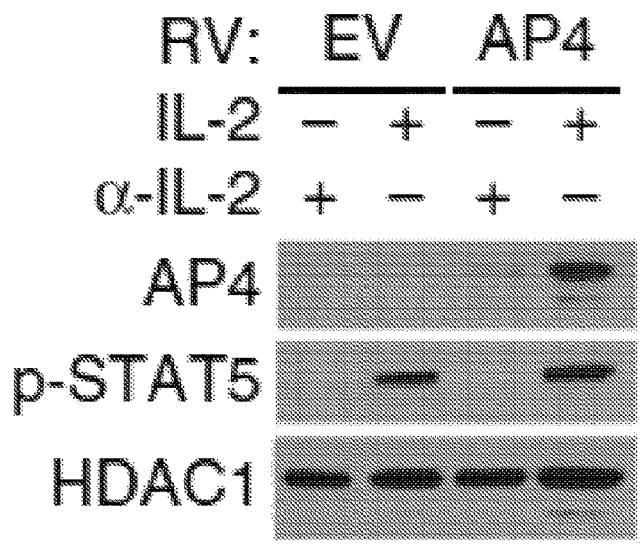
FIG. 2A, FIG. 2B, FIG. 2C, FIG. 2D, FIG. 2E, FIG. 2F, FIG. 2G, FIG. 2H, FIG. 2I, and FIG. 2J depict graphs and immunoblots showing AP4 is post-transcriptionally regulated in $CD8^+$ T cells. Phosphorylated STAT5 and β-tubulin serve as controls. (n=4).
Figure 2B:
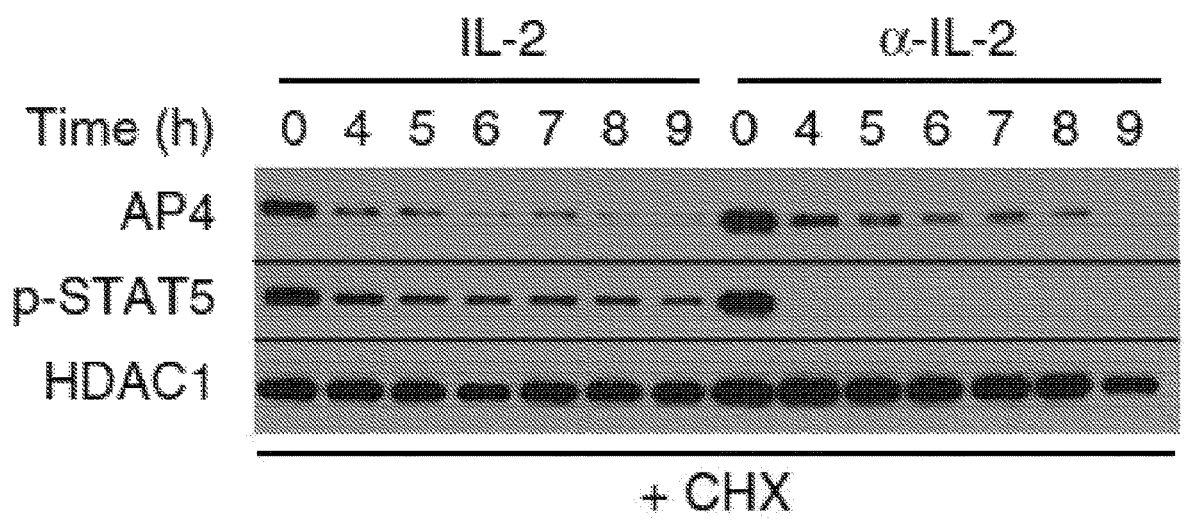
Figure 2C:
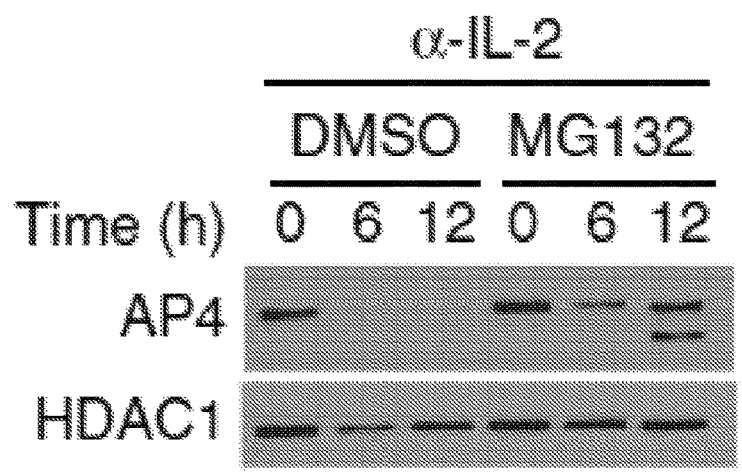
Figure 2D:
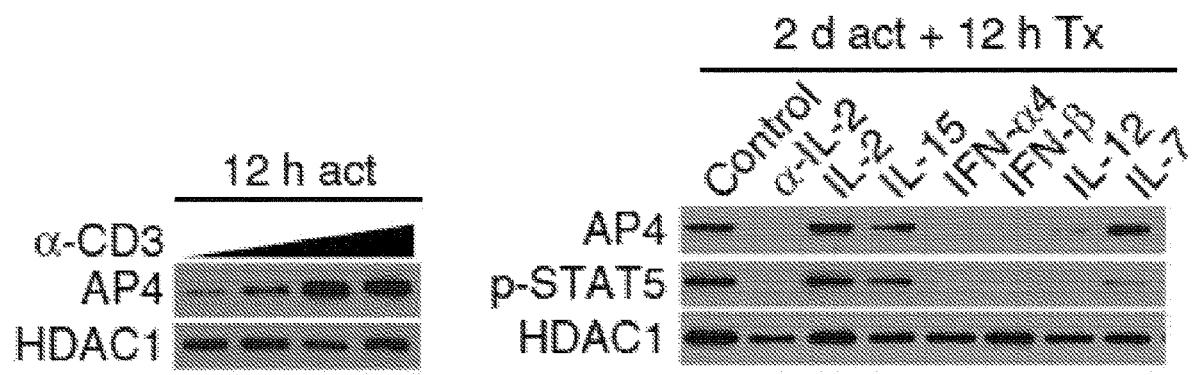
Figure 2E:
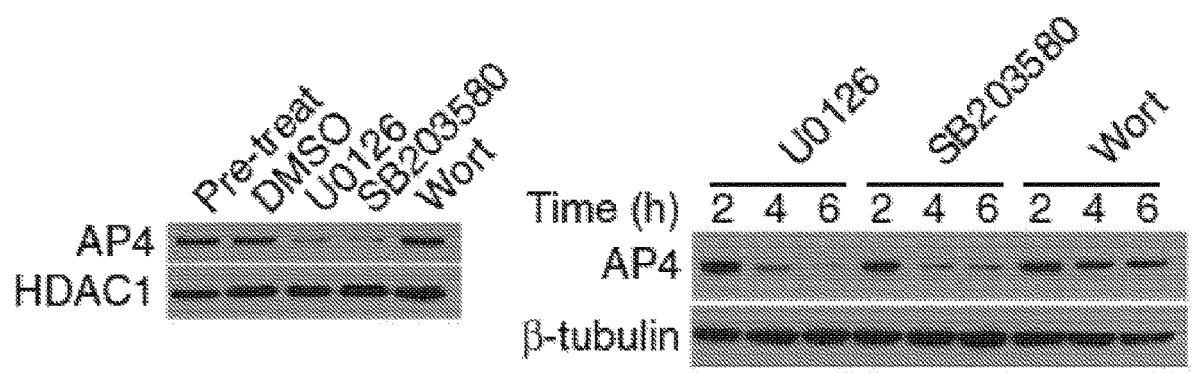

Previous studies suggested that IL-2 sustains clonal expansion of T cells in vitro and, possibly, in vivo.[14,15] IL-2 also promotes effector differentiation of $CD8^+$ T cells.[12,16] Therefore, it was hypothesized that factors important for clonal expansion, effector differentiation, or both could be regulated by IL-2R signals. Seventy-two transcription factors that were regulated by IL-2 in $CD8^+$ T cells were initially found[4] (FIG. 1A). Among these factors, AP4 was pursued because the data showed that its expression at the protein level was regulated dynamically by IL-2R signals,[4] despite only a moderate change in mRNA levels (FIG. 1B and FIG. 1C). AP4 is an evolutionarily conserved bHLH protein that was identified as a regulator for epigenetic gene silencing during thymocyte development.[8,17,18] In WT $CD8^+$ T cells deprived of IL-2R signals, AP4 transcript levels decreased by approximately 2-fold (FIG. 1B). In contrast, AP4 protein was almost completely abolished following overnight treatment with an anti-IL-2 neutralizing antibody, even in the presence of endogenous or overexpressed mRNA (FIG. 2c; FIG. 1 in Ref. [4]). These results suggested that AP4 expression is regulated transcriptionally, but even more markedly at the protein level, by IL-2R signals in CD8$^+$ T cells. In this regard, AP4 is a short-lived protein that is constitutively degraded by the ubiquitin-proteasome pathway (FIG. 2A, FIG. 2B, FIG. 2C, FIG. 2D, FIG. 2E, and FIG. 2F).

Figure 2F:
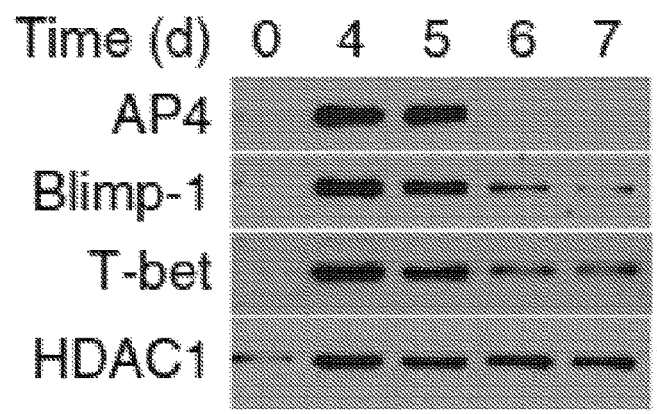
Figure 2G:
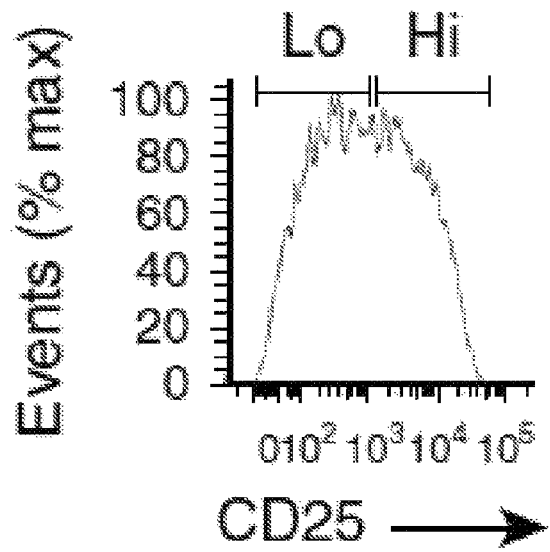
Figure 2H:
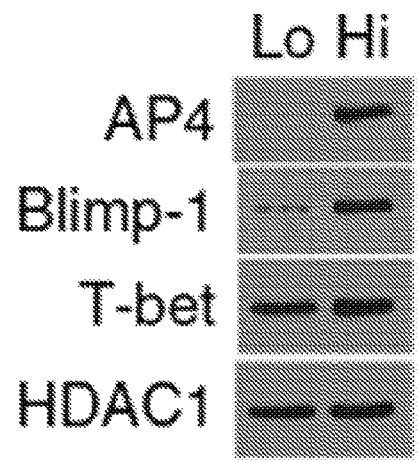
Figure 2I:
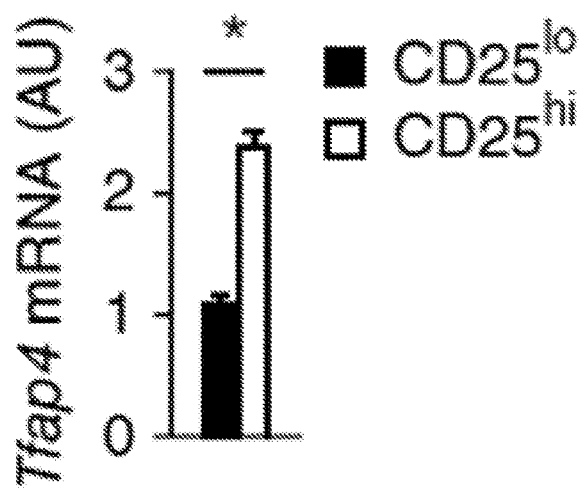
Figure 2J:
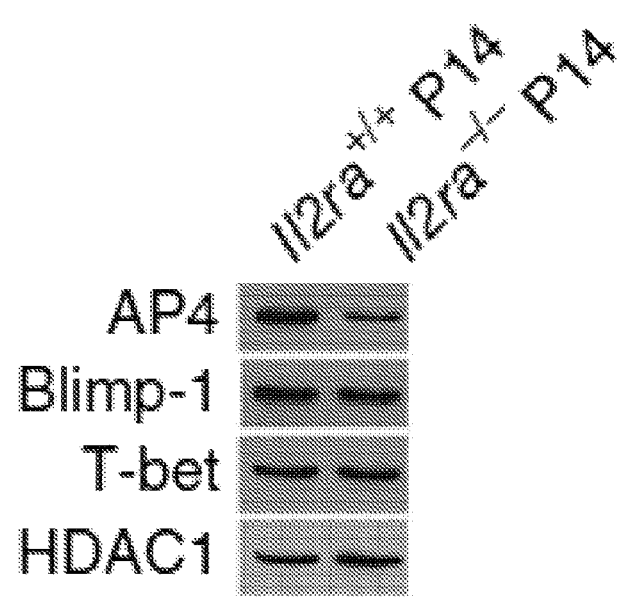
Figure 3A:
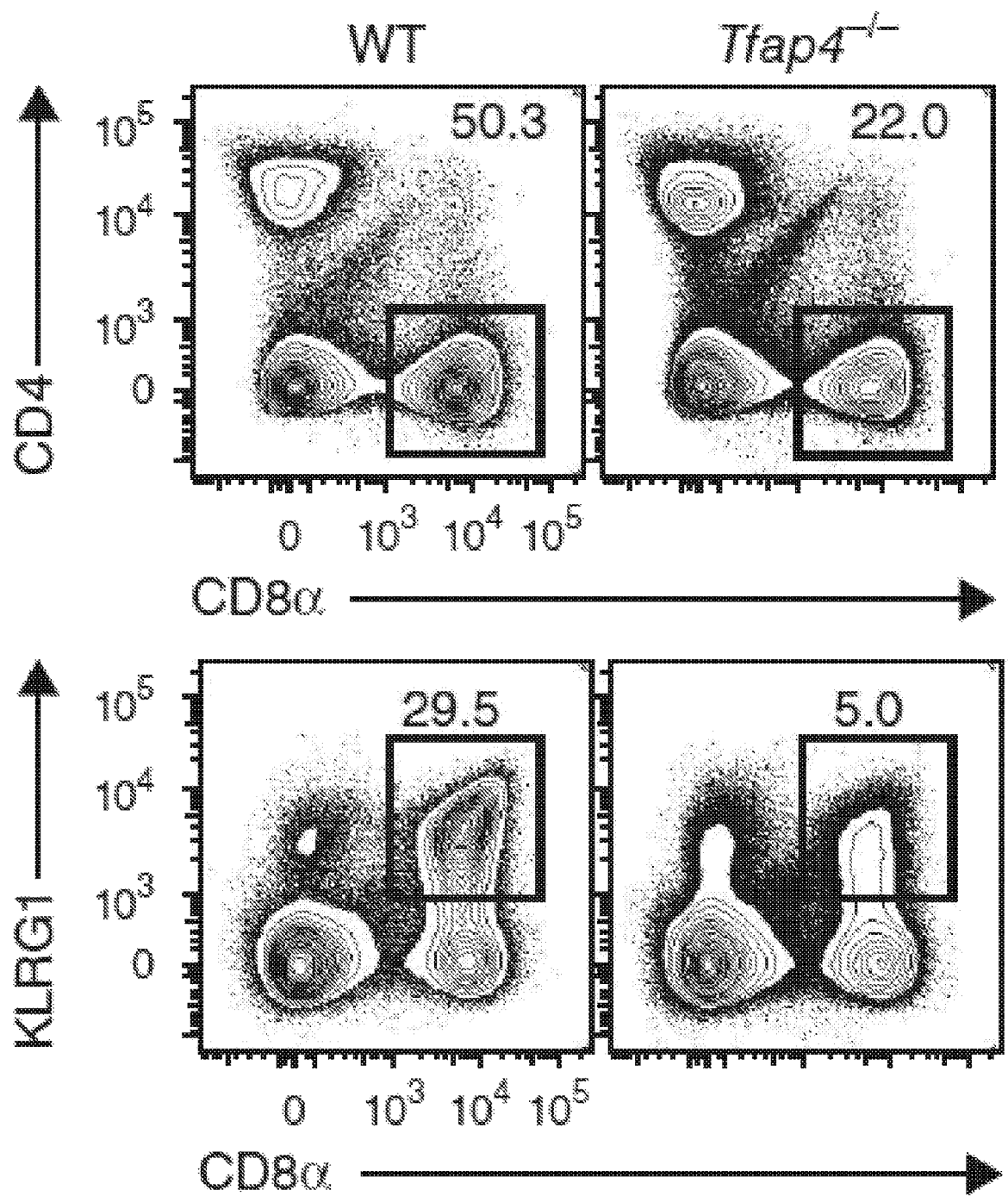
FIG. 3A, FIG. 3B, FIG. 3C, FIG. 3D, FIG. 3E, FIG. 3F, FIG. 3G, FIG. 3H, FIG. 3I, and FIG. 3J depict flow cytometry plots and graphs showing that AP4 is required for expansion of Ag-specific CD8+ T cells following LCMV-Arm infection.
Figure 3B:
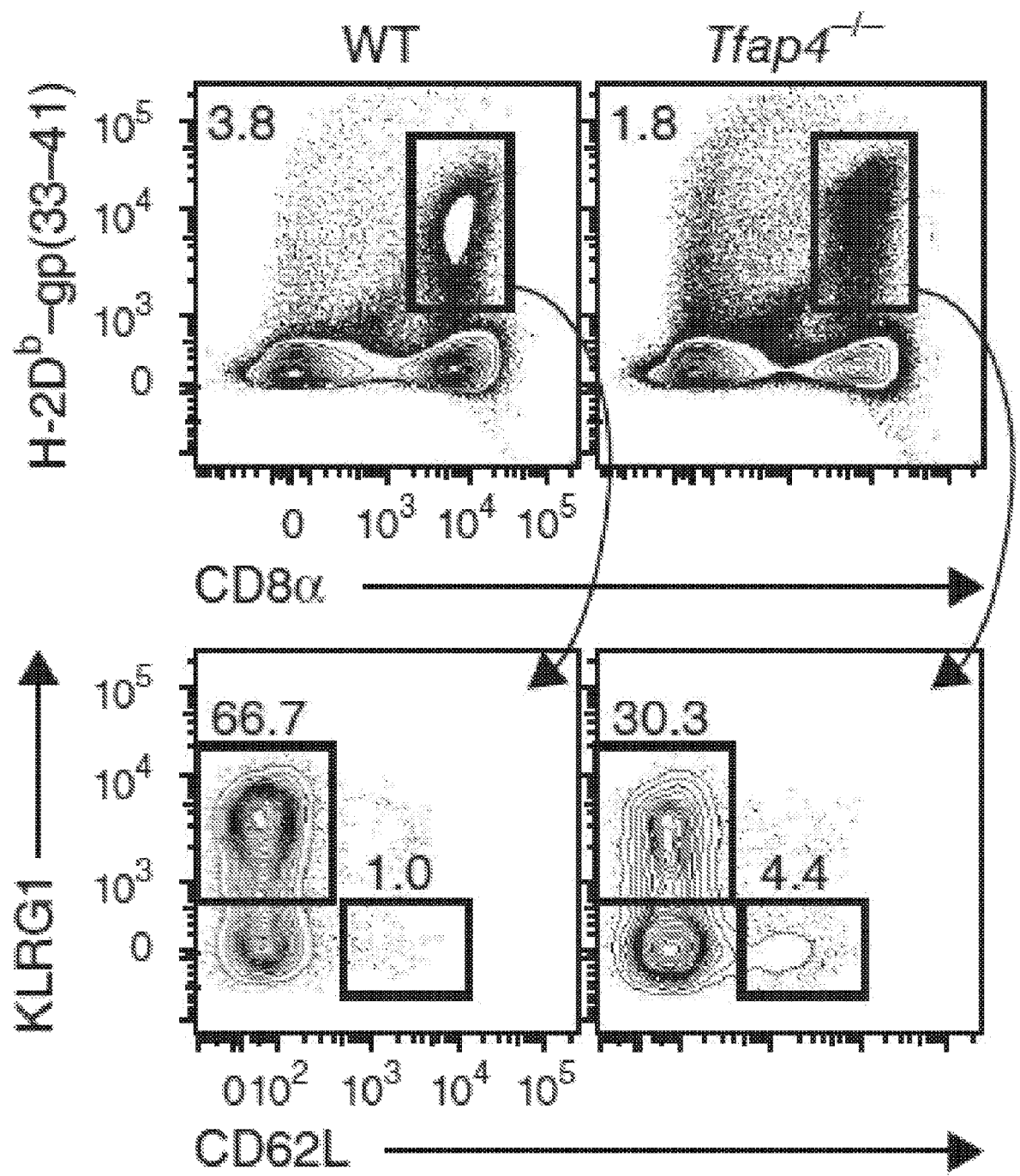
Figure 3C:
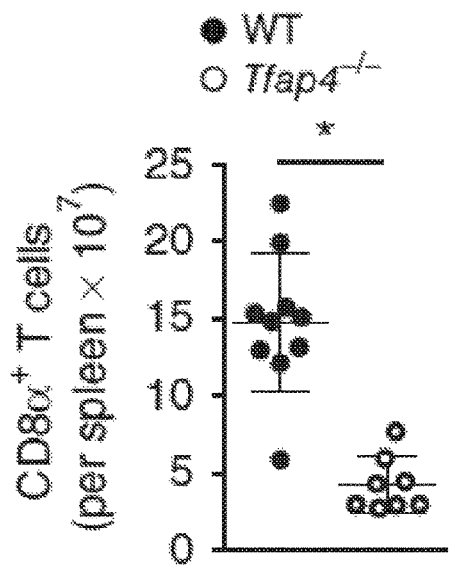
Figure 3D:
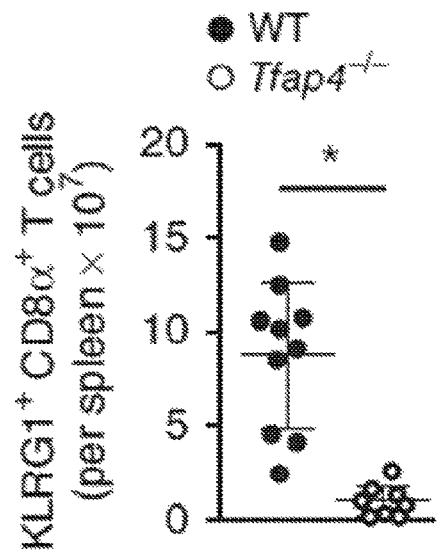
Figure 3E:
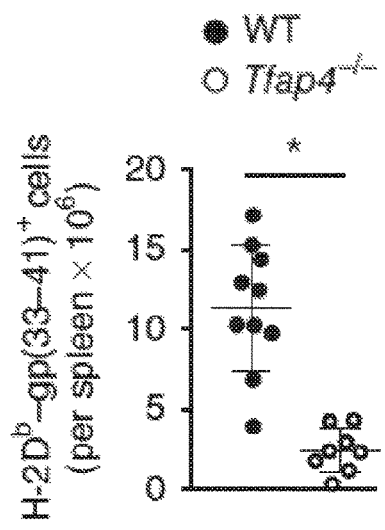
Figure 3F:
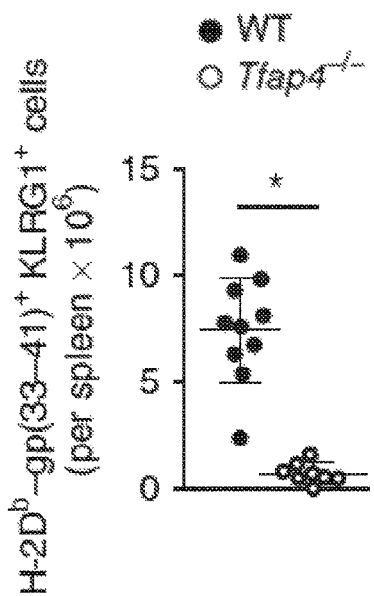
Figure 3G:
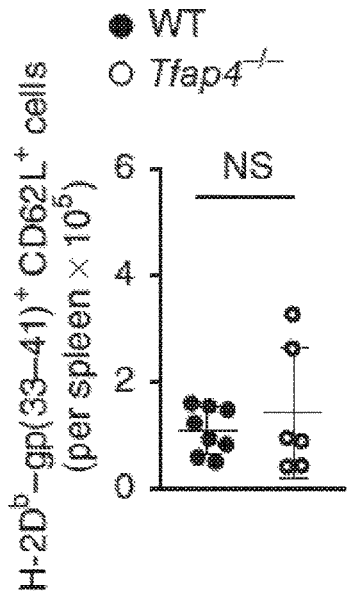
Figure 3H:
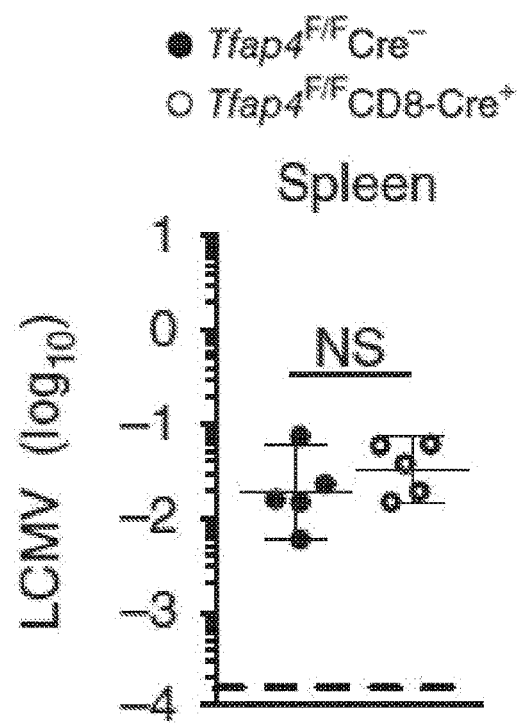
Figure 3I:
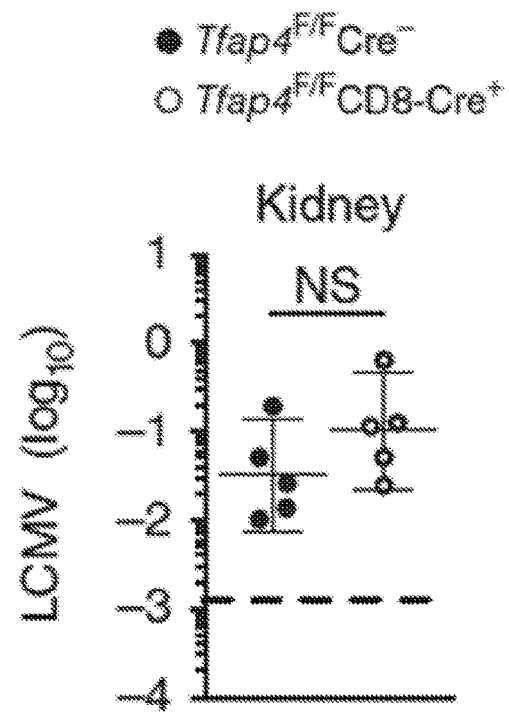
Figure 3J:
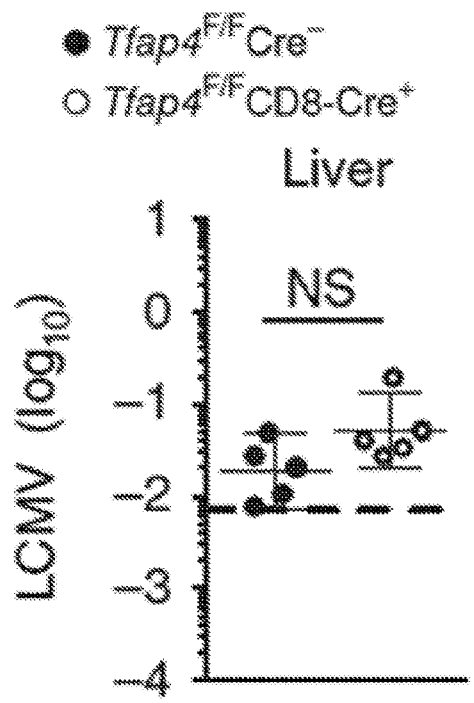
Figure 4A:
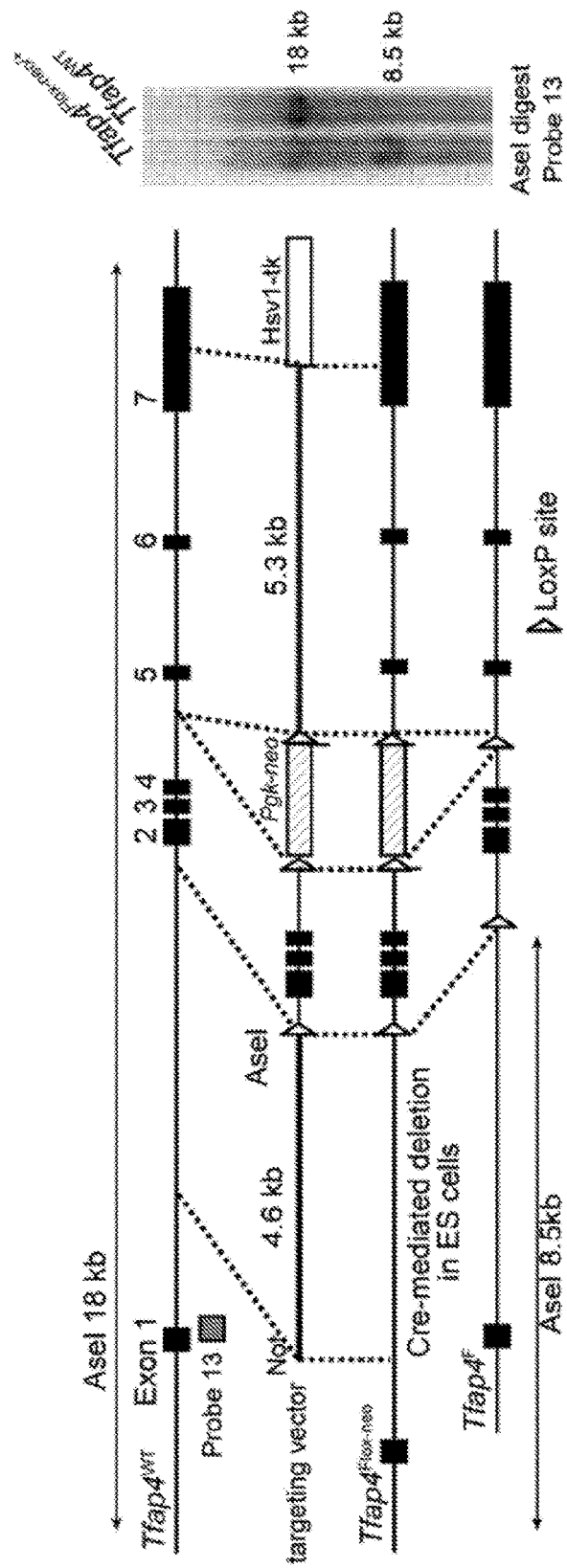
Figure 4B:
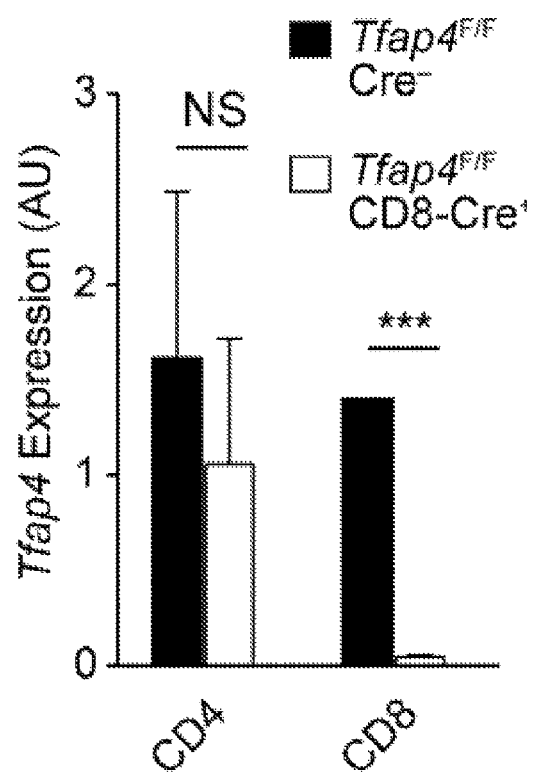
Figures 4C, 4D:
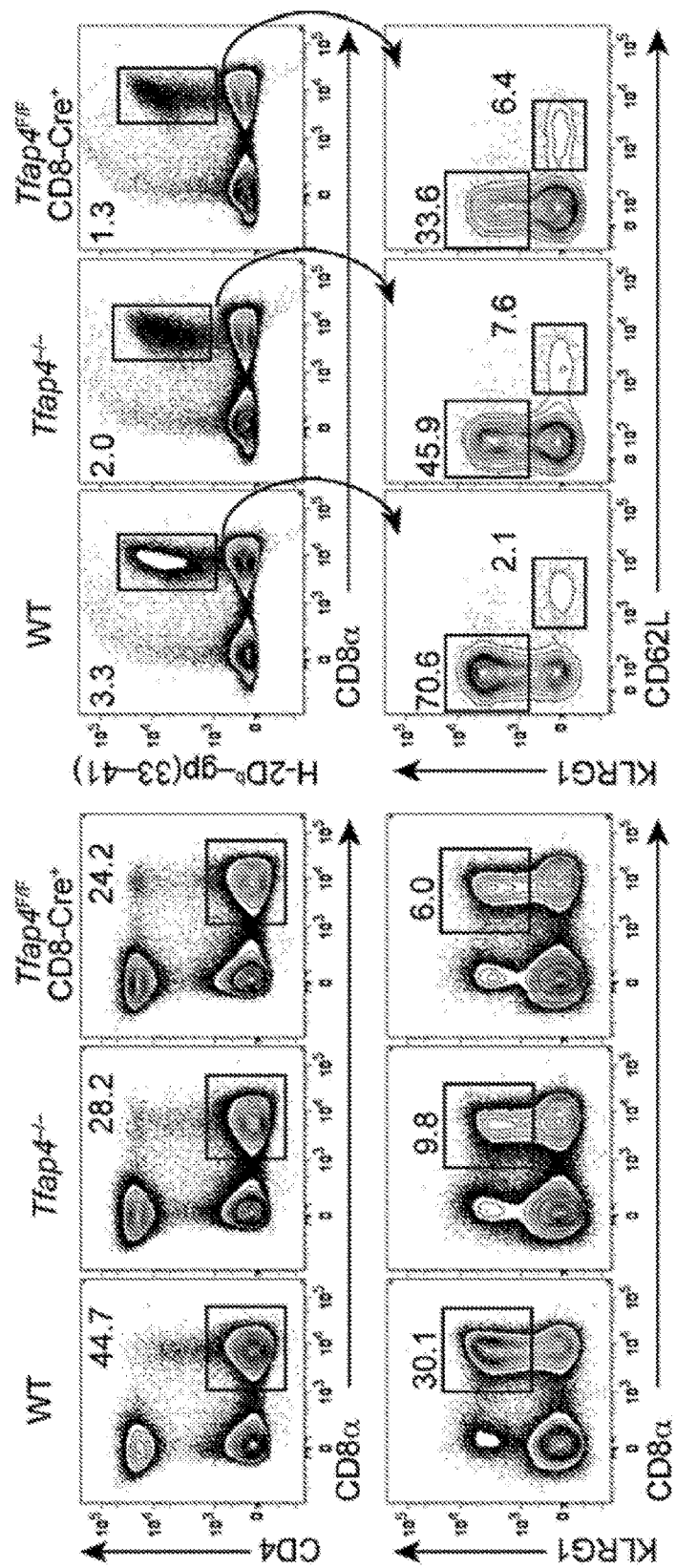
Figure 4E:
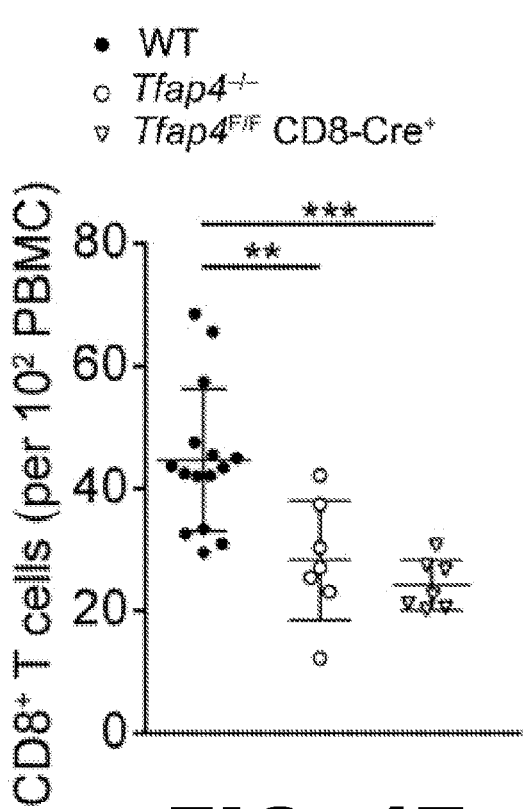
Figure 4F:
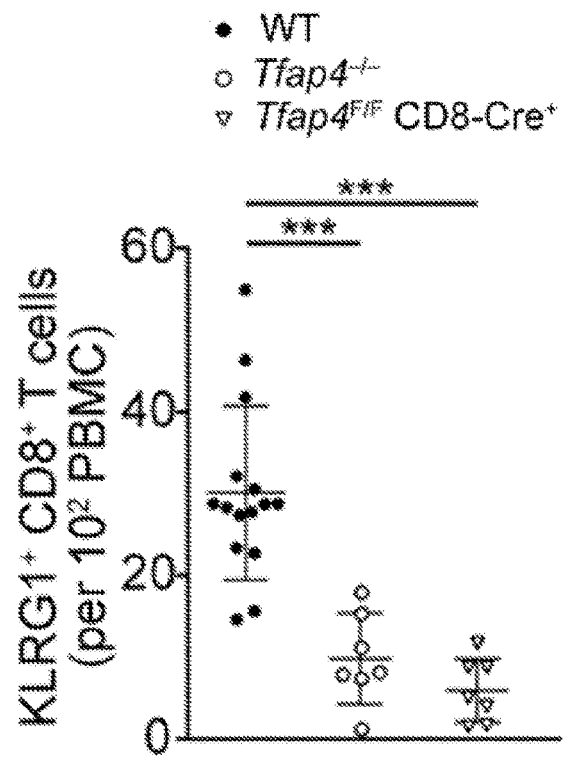
Figure 4G:
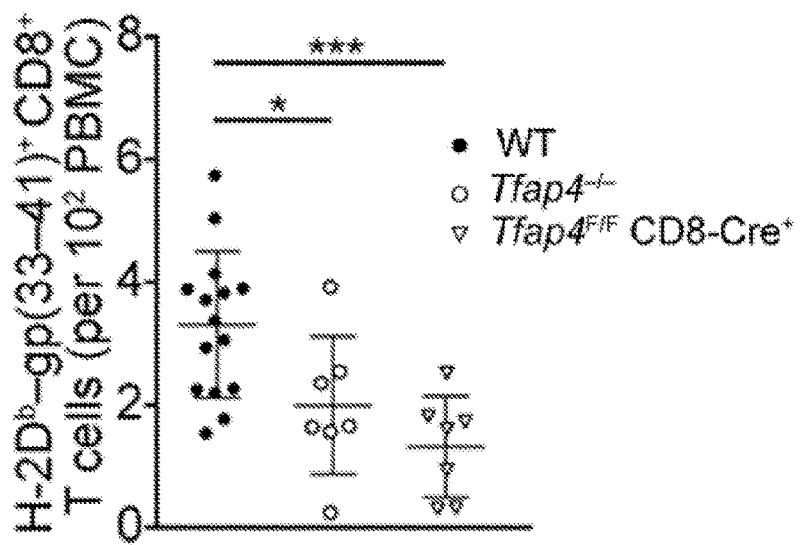

Example 2. Expression of AP4 Protein is IL-2R-Dependent in CD8$^+$ T Cells In Vivo The expression kinetics of AP4 in CD8$^+$ T cells in vivo were defined using adoptive transfer of P14 TCR-Tg CD8$^+$ T cells (CD90.1) into C57BL/6 (CD90.2) mice followed by infection with the Armstrong strain of Lymphocytic choriomeningitis virus (LCMV-Arm). AP4 protein was highly expressed in P14 cells on days 4 and 5 after infection, and its expression was diminished on day 6 (FIG. 2F). In activated CD8$^+$ T cells on day 5 after infection, expression of AP4 protein was detected specifically in those expressing CD25, the high-affinity IL-2R (FIG. 2G, FIG. 2H, and FIG. 2I), also confirming that expression of AP4 protein correlates with IL-2R signals. Il2ra$^{-/-}$ P14 T cells expressed ~4-fold lower level of AP4 protein compared to WT P14 cells, indicating that IL-2R signals are required for accumulation of AP4 protein in T cells[4] (FIG. 2J).

Figure 5A:
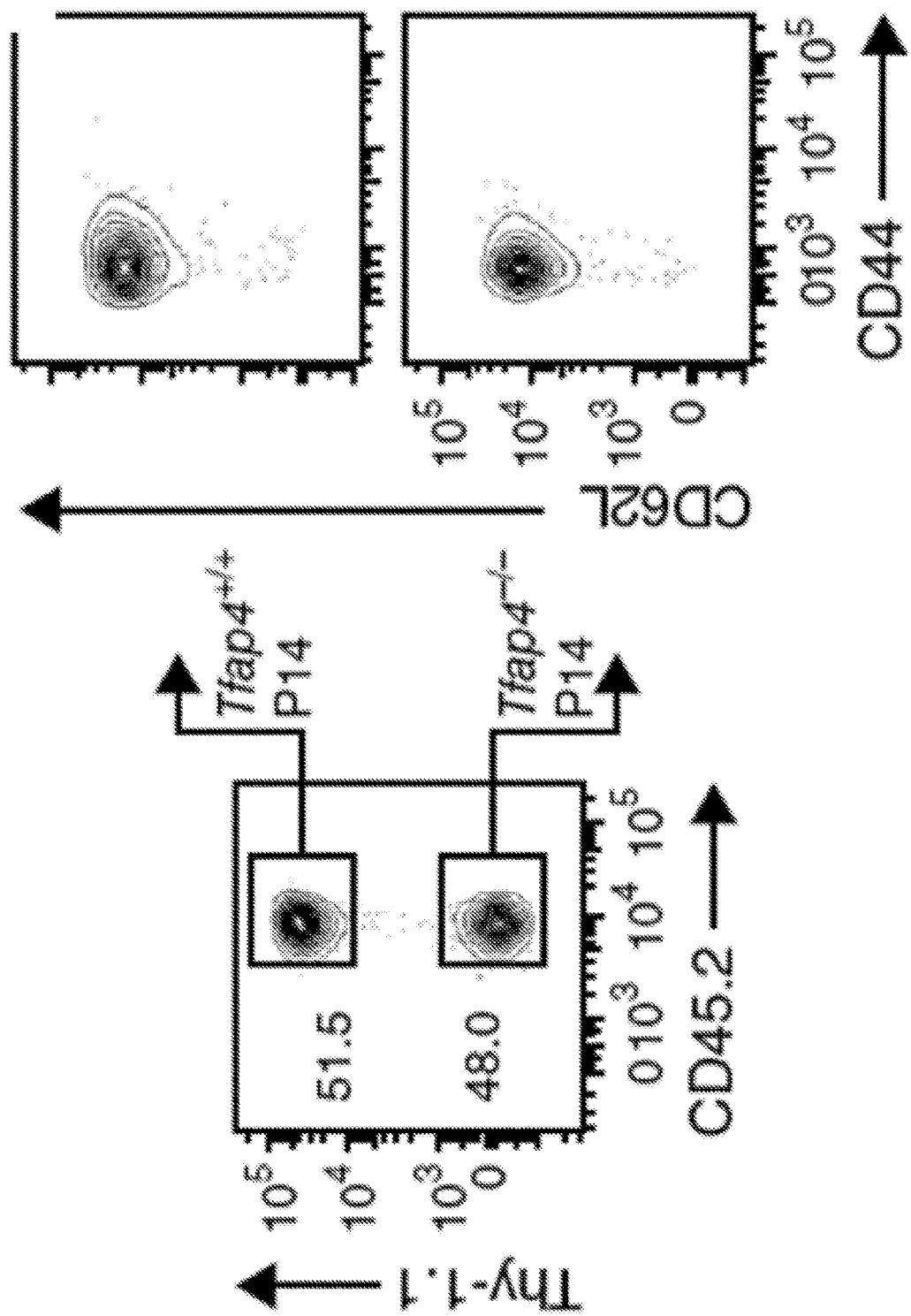
FIG. 5A, FIG. 5B, FIG. 5C, FIG. 5D, FIG. 5E, FIG. 5F, FIG. 5G, FIG. 5H, FIG. 5I, and FIG. 5J depict graphs and flow cytometry plots showing that AP4 is required for sustained CD8 clonal expansion but not for initial proliferation.
Figure 5B:
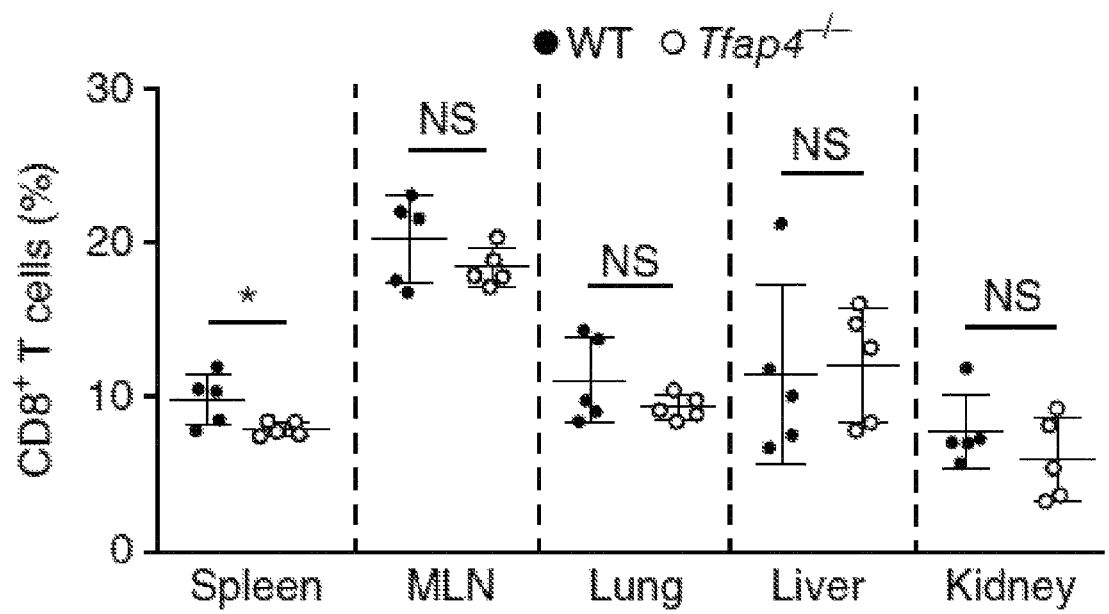
Figure 5C:
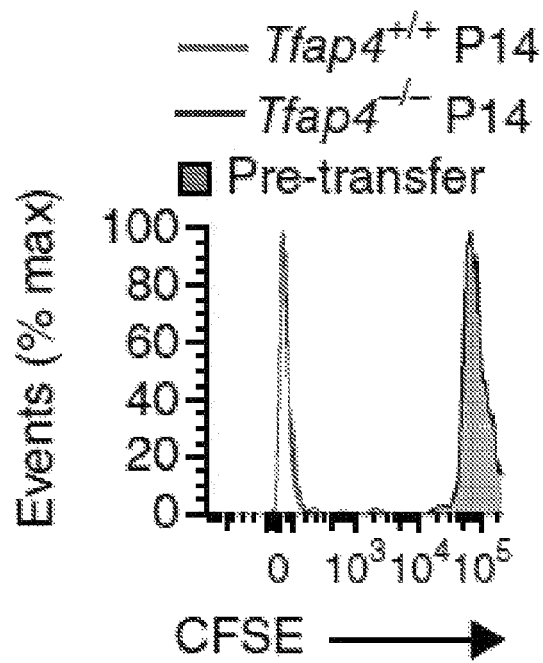
Figure 5D:
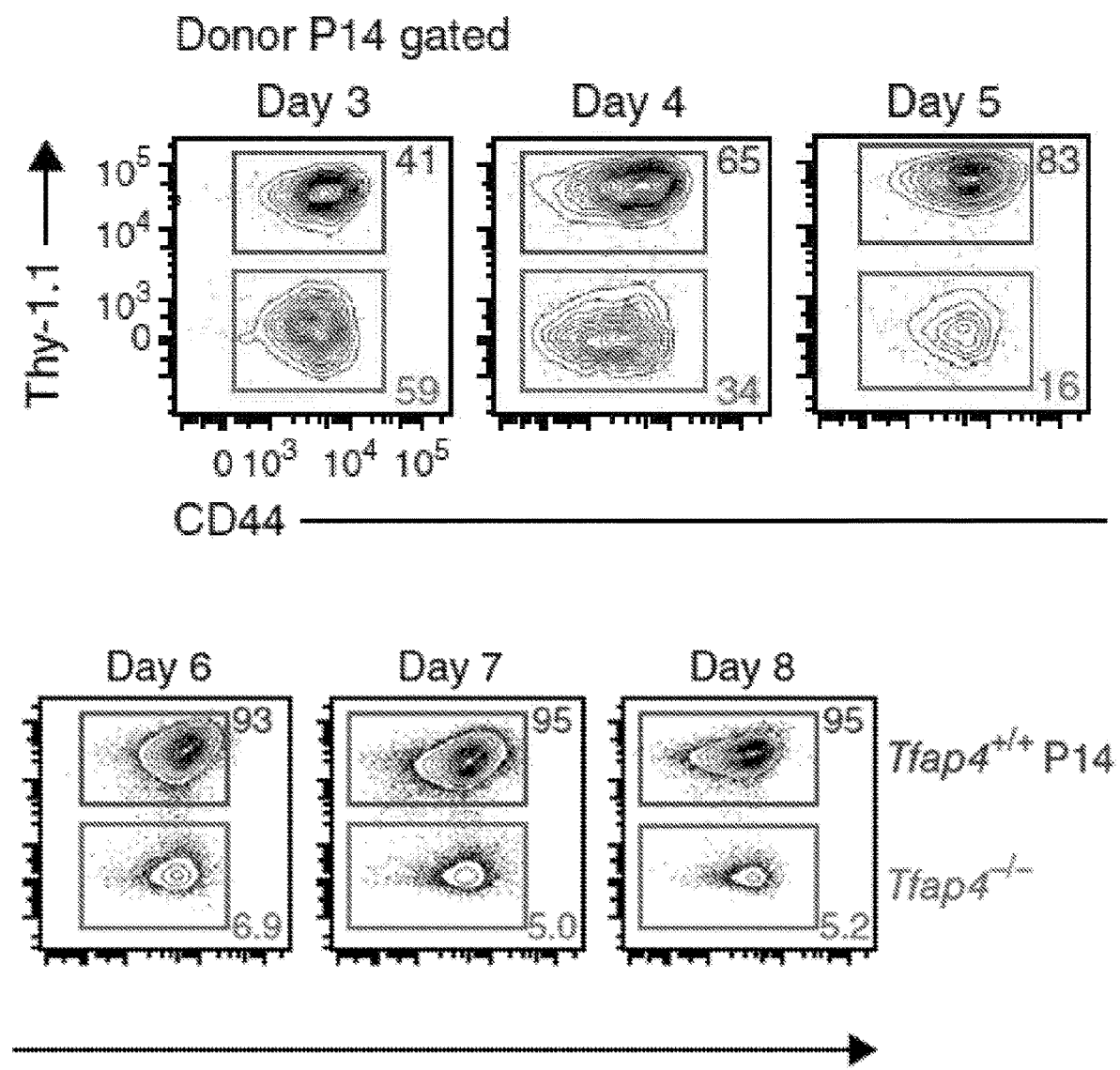
Figure 5E:
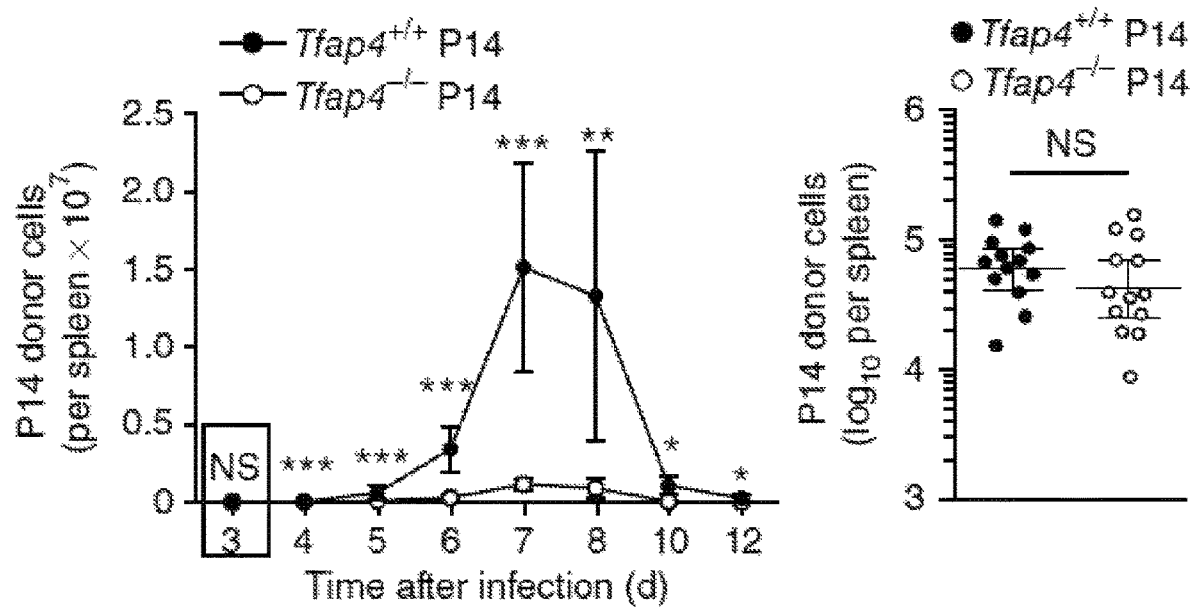
Figure 5F:
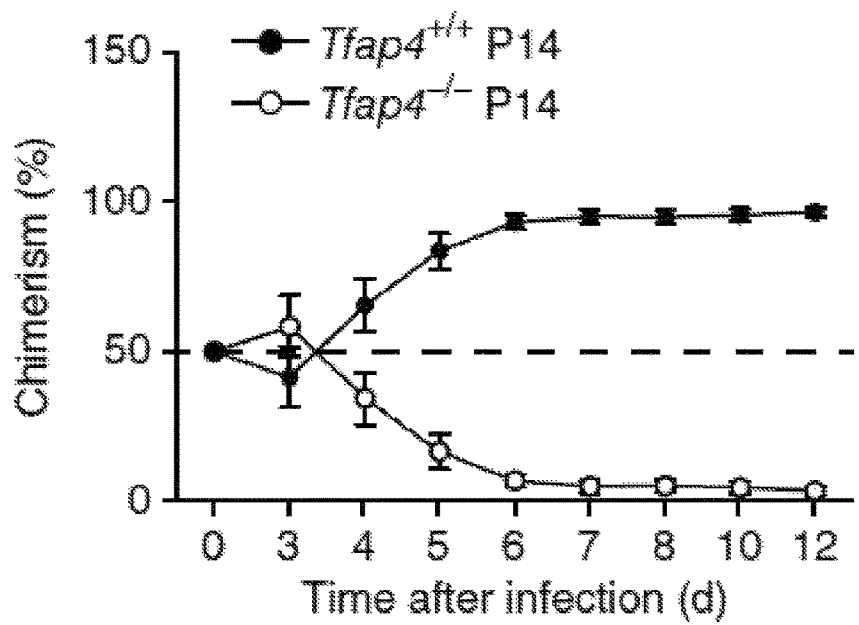
Figure 5G:
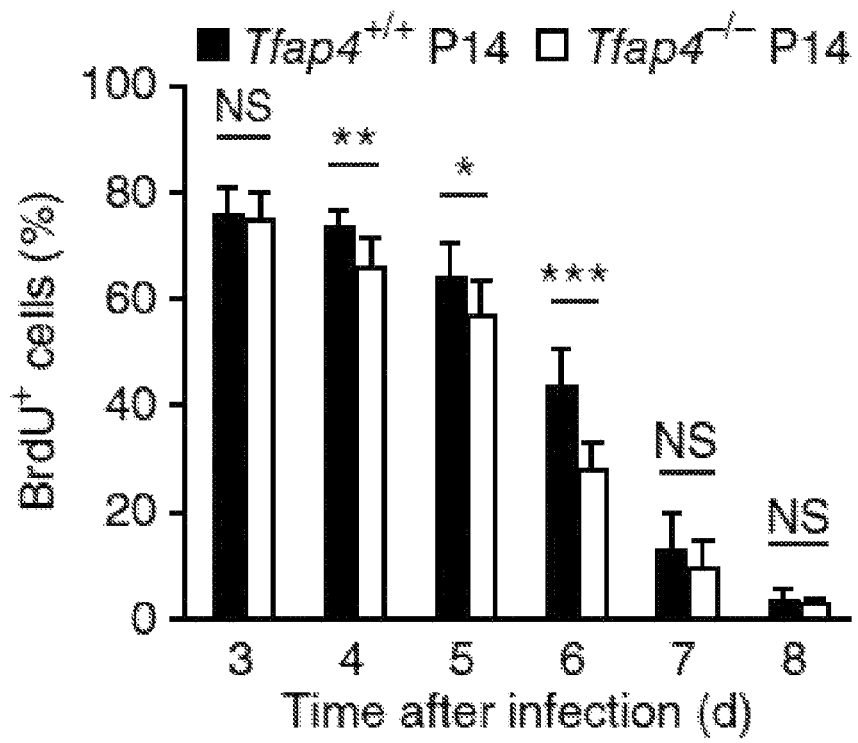
Figure 5H:
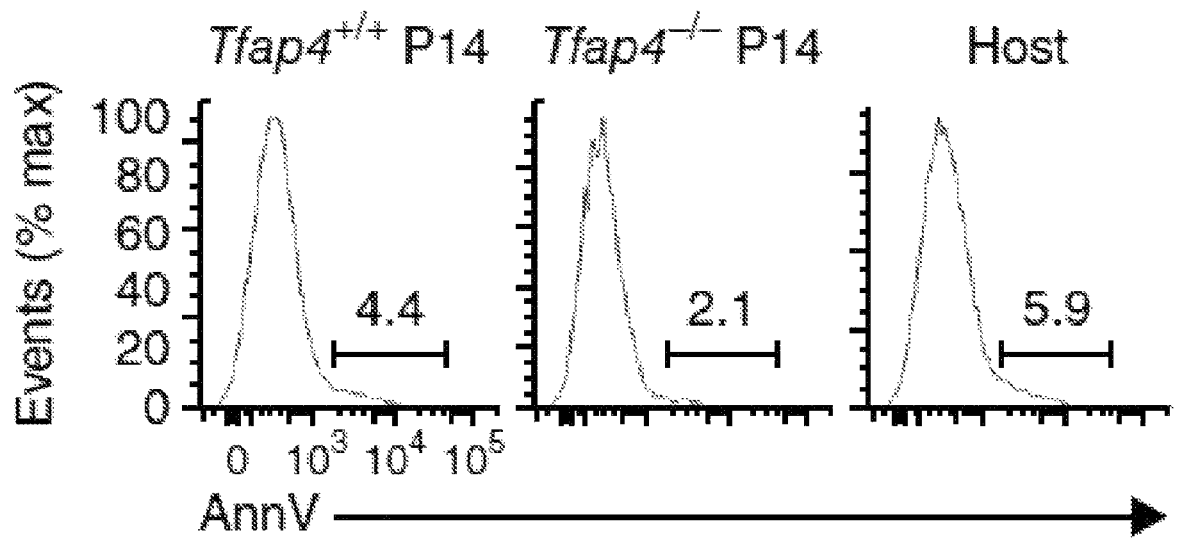
Figure 5I:
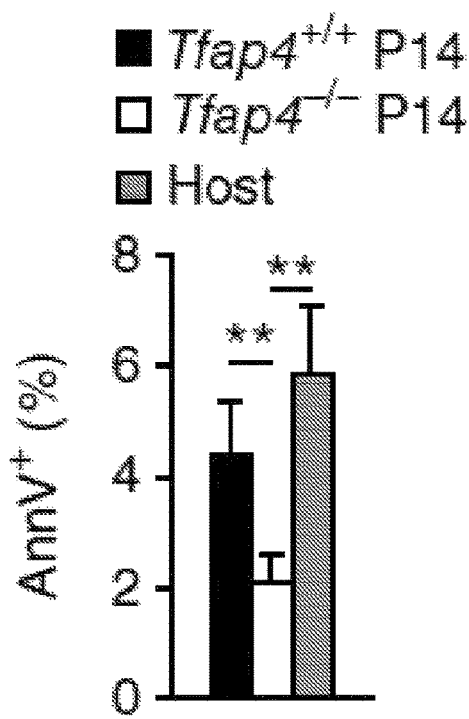
Figure 5J:
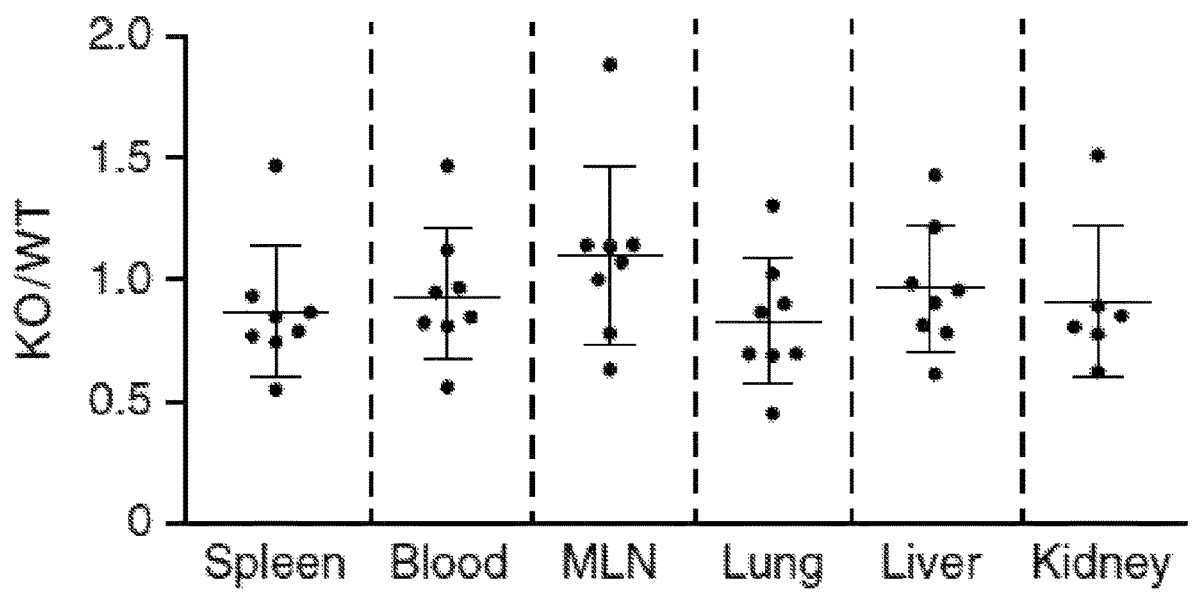
Figure 6A:
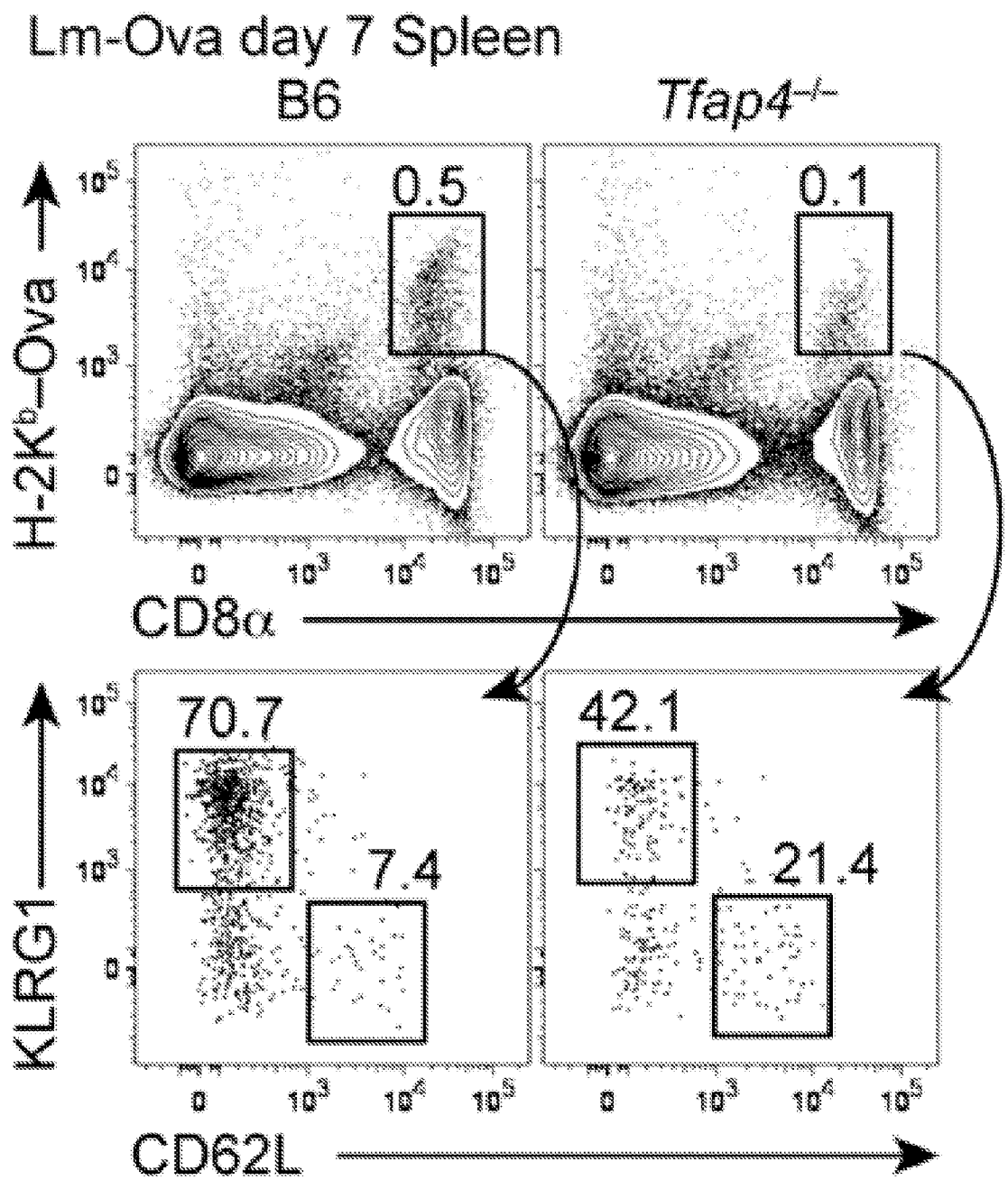
Figure 6B:
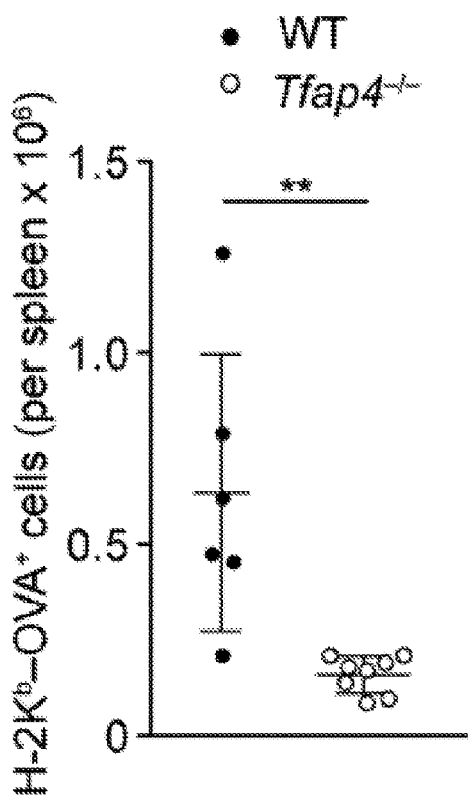
Figure 6C:
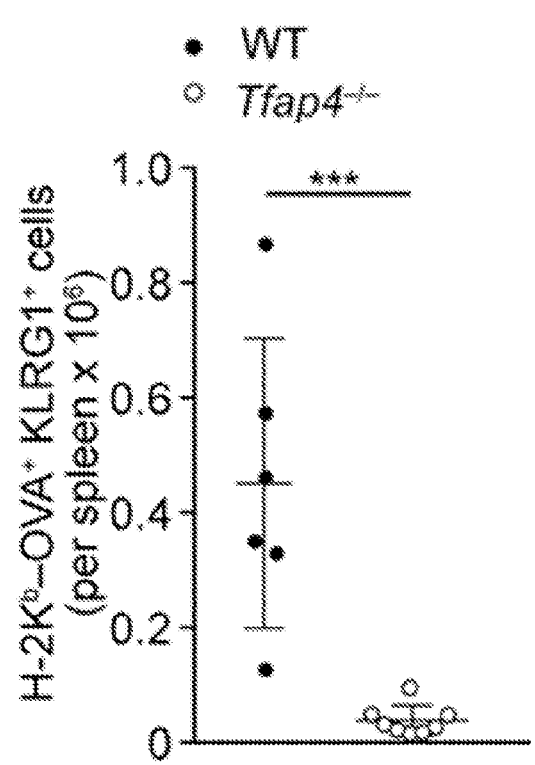
Figure 6D:
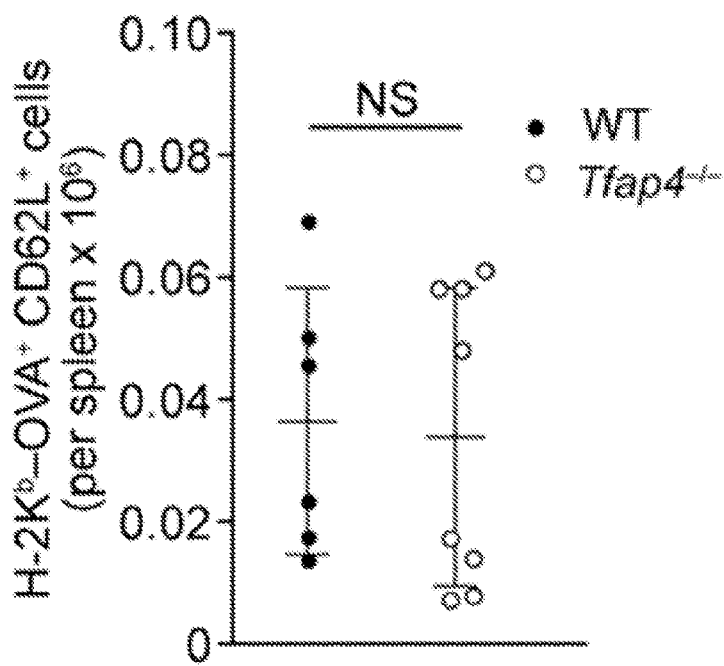
Figure 6E:
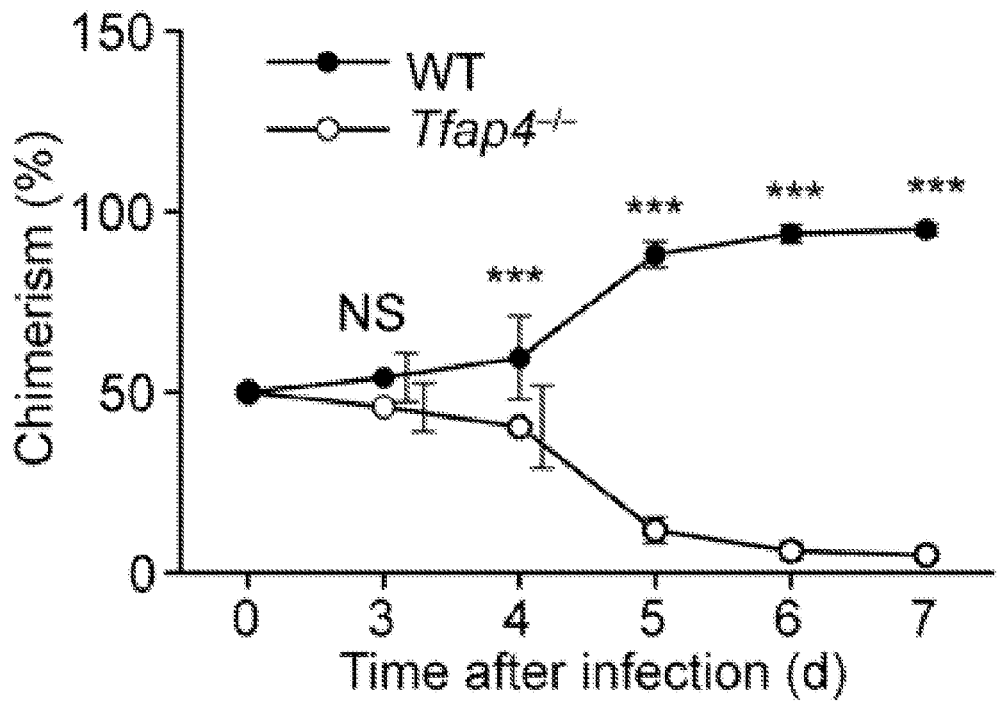
Figure 6F:
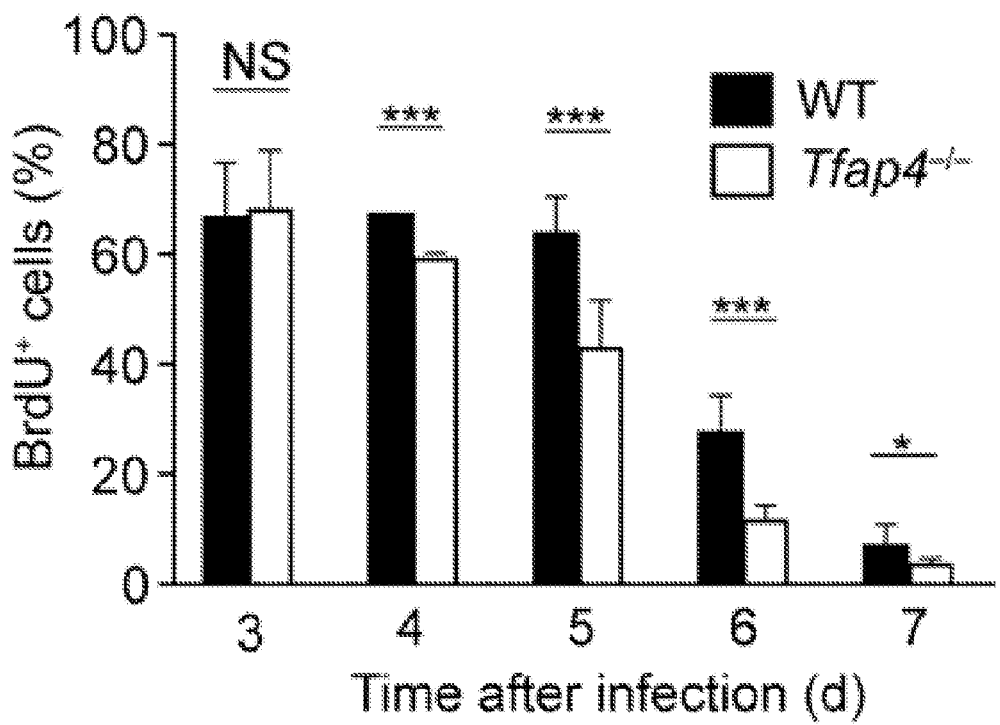
Figures 6J, 6K:
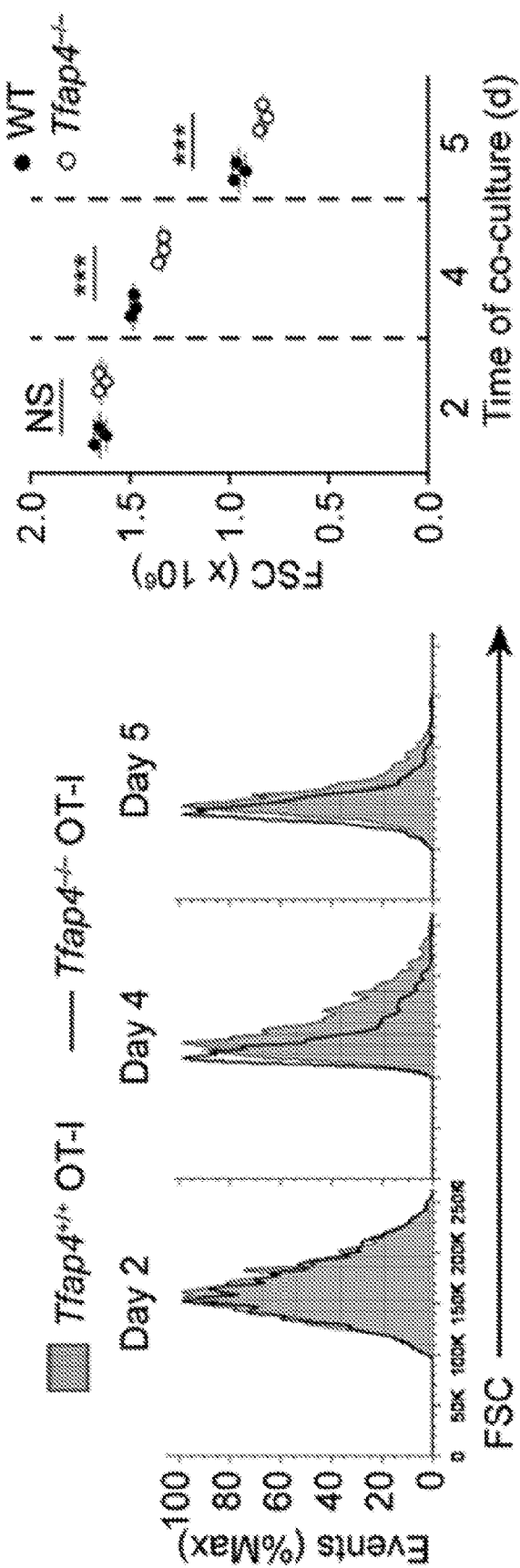

Example 3. AP4 is Required for Clonal Expansion and Effector Differentiation of CD8$^+$ T Cells To define the function of AP4 in CD8$^+$ T cell responses, AP4-KO (Tfap4$^{-/-}$) mice were infected with LCMV-Arm. At the peak of response, numbers of total CD8$^+$ T cells and LCMV-GP33-specific CD8$^+$ T cells, particularly those expressing the terminally differentiated effector marker KLRG1 (Ref. [19,20]), were substantially reduced (FIG. 3C, FIG. 3D, FIG. 3E, FIG. 3F, and FIG. 3G). These results indicate that AP4 is essential for maximal clonal expansion and effector differentiation of CD8$^+$ T cells. Two complementary experiments were performed to show that the AP4 requirement is CD8$^+$ T cell-intrinsic. First, AP4 was deleted specifically in CD8$^+$ T cells using a Tfap4$^{Flox}$ allele[4] and the CD8-Cre Tg mice, in which Cre is expressed in CD8$^+$ T cells after positive selection.[21] In the LCMV-Arm infection model, identical results between Tfap4$^{-/-}$ and CD8-Cre$^+$ Tfap4$^{F/F}$ mice were observed[4] (FIG. 4). As a complementary approach, adoptive transfer of P14 T cells was used. A 1:1 mixture of Tfap4$^{-/-}$ (CD45.2; CD90.2) and control WT (CD45.2; CD90.1) P14 cells was co-transferred into CD45.1 WT host mice, followed by LCMV-Arm infection. Before infection, similar numbers of Tfap4$^{-/-}$ and WT P14 cells were recovered (FIG. 5), indicating that AP4 is not required for homing or survival of transferred cells in the host. At the peak of response, the number of splenic Tfap4$^{-/-}$ P14 AP4 cells was 15-20 fold lower than that of WT P14 in the same host mice[4] (FIG. 5E), confirming a cell-intrinsic requirement for AP4 in expansion of Ag-specific CD8$^+$ T cells. By contrast, absolute numbers and BrdU incorporation rates were comparable between Tfap4$^{-/-}$ and control WT P14 cells on day 3 after infection[4] (FIG. 5E, FIG. 5F). These data collectively indicate that Tfap4$^{-/-}$ CD8$^+$ T cells are primed and proliferate comparably to WT cells while cMyc is expressed. Therefore, the reduced numbers of Tfap4$^{-/-}$ CD8$^+$ T cells result from their slower proliferation after the cMyc decay (post-Myc phase). Similar phenotypes were observed using OT-I cells and Lm-Ova infection (FIG. 6A, FIG. 6B, FIG. 6C, FIG. 6D, FIG. 6E, FIG. 6F, FIG. 6G, FIG. 6H, FIG. 6I, FIG. 6J, FIG. 6K, FIG. 6L, FIG. 6M, and FIG. 6N).

Figure 7A:
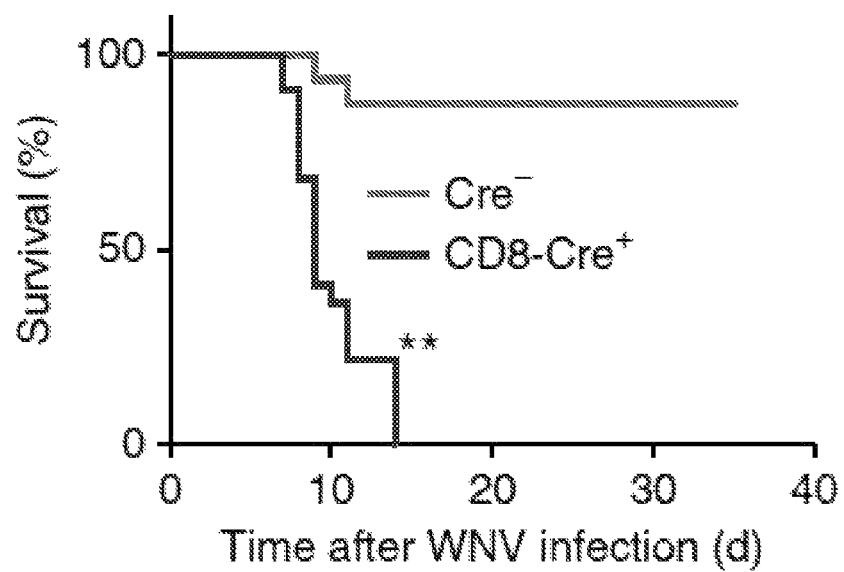
FIG. 7A, FIG. 7B, and FIG. 7C depict graphs showing that AP4 is essential for host protection against WNV infection in a CD8$^+$ T cell-intrinsic manner.
Figure 7B:
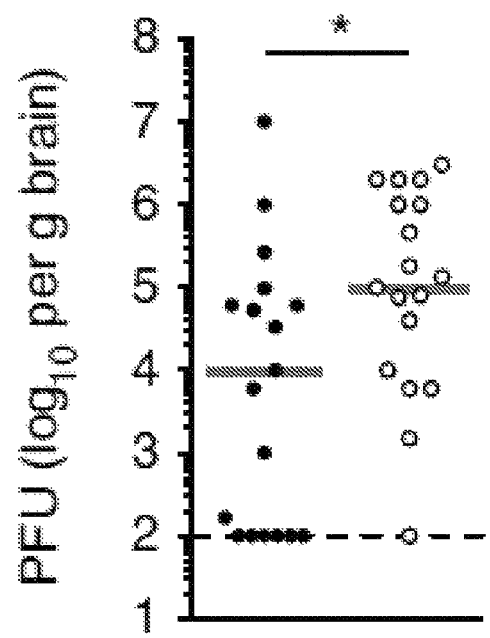
Figure 7C:
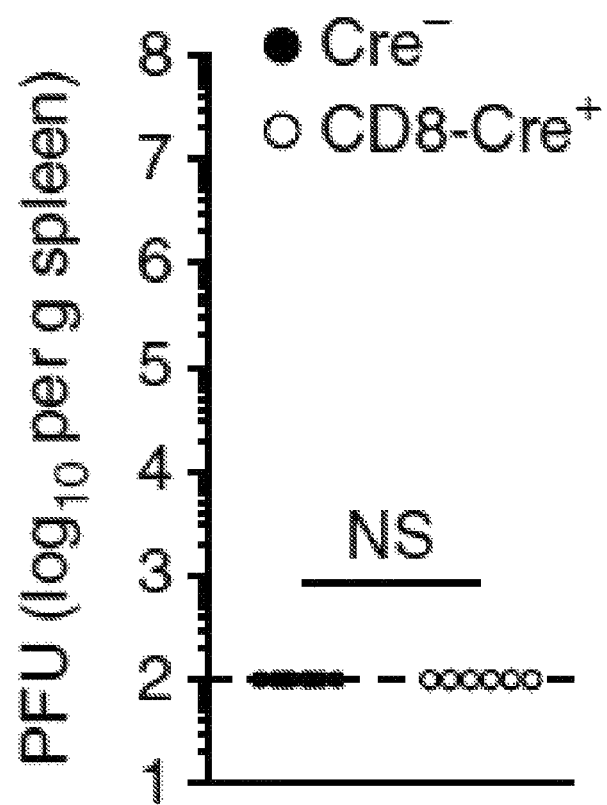

Example 4. AP4 is Essential for Host Protection Against West Nile Virus (WNV) Infection AP4 function was tested during immune responses against pathogenic viruses using a WNV infection model cells because mice require Ag-specific CD8$^+$ T cells for clearance and protection during a later phase of the acute response.[22,23] While a large proportion of control Cre$^-$Tfap4$^{F/F}$ survived, all of the CD8-Cre$^+$ Tfap4$^{F/F}$ mice died between days 9-13 after infection due to poor control of viral replication in the brain[4] (FIG. 7). These findings establish AP4 as a critical factor that sustains CD8$^+$ T cell activation, thereby providing host protection against pathogen infection.

Figure 8:
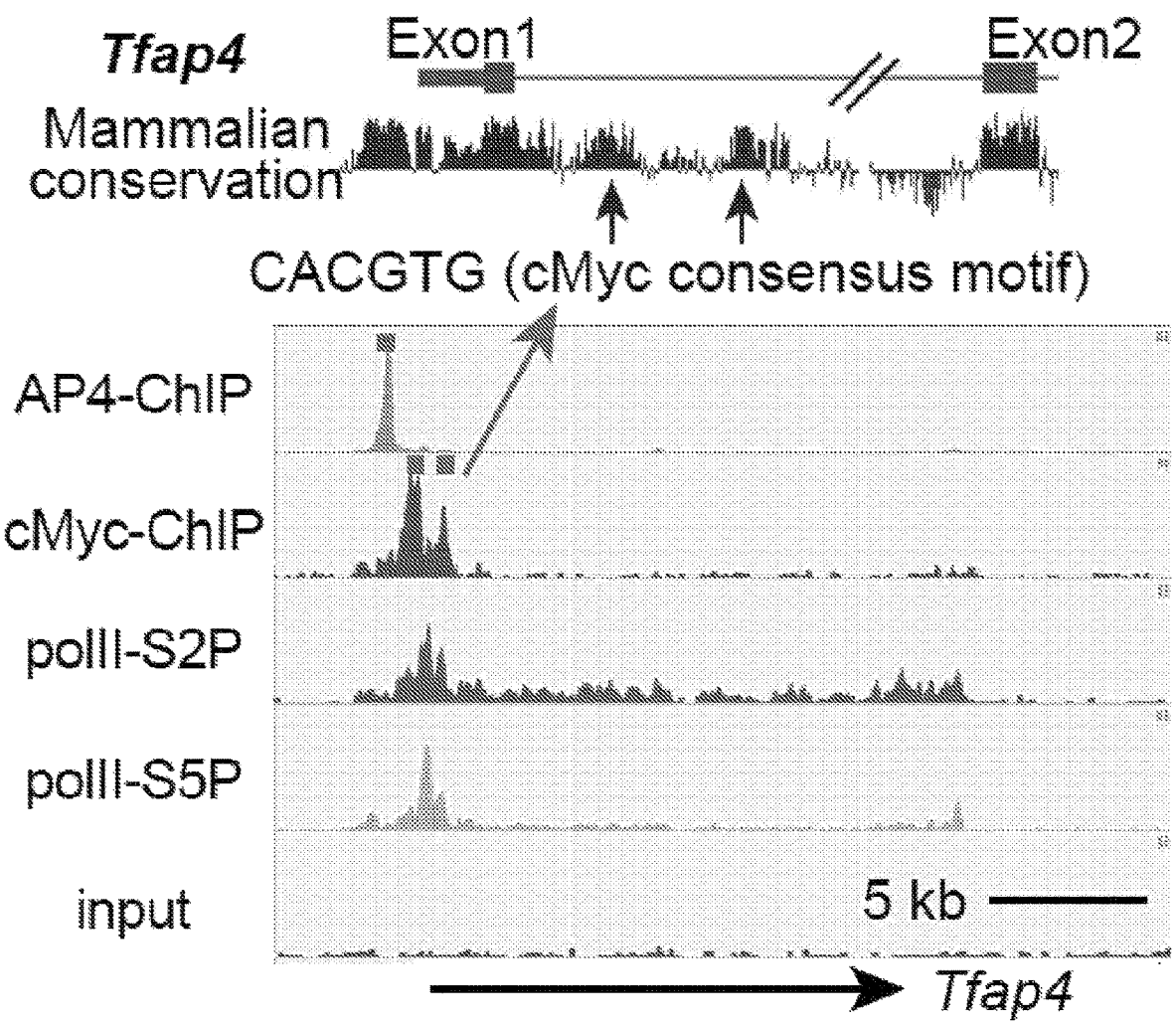
FIG. 8 depicts ChIPseq analysis showing that cMyc binds to two cMyc consensus sequences in intron 1 in CD8$^+$ T cells.
Figure 9A:
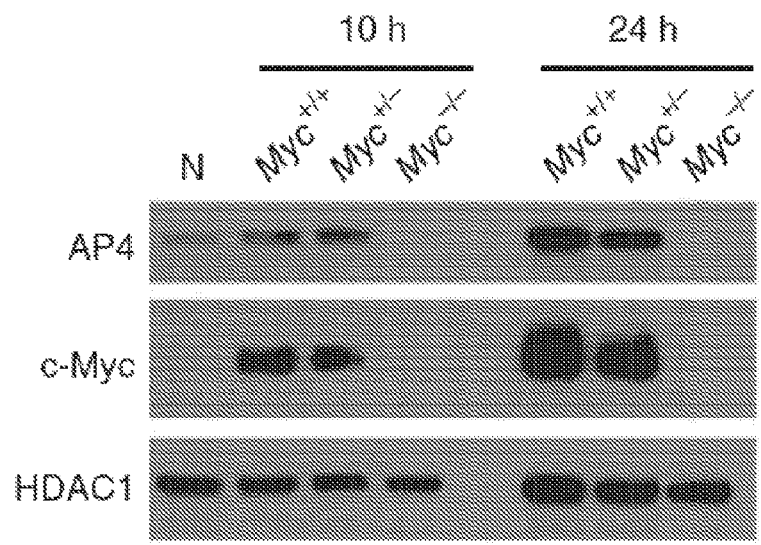
FIG. 9A, FIG. 9B, FIG. 9C, FIG. 9D, FIG. 9E, FIG. 9F, FIG. 9G, FIG. 9H, FIG. 9I, FIG. 9J, FIG. 9K, FIG. 9L, FIG. 9M, FIG. 9N, FIG. 9O, FIG. 9P, FIG. 9Q, FIG. 9R, FIG. 9S, and FIG. 9T depict graphs, flow cytometry plots and immunoblots showing that AP4 is induced by c-Myc and sustains glycolysis.
Figure 9B:
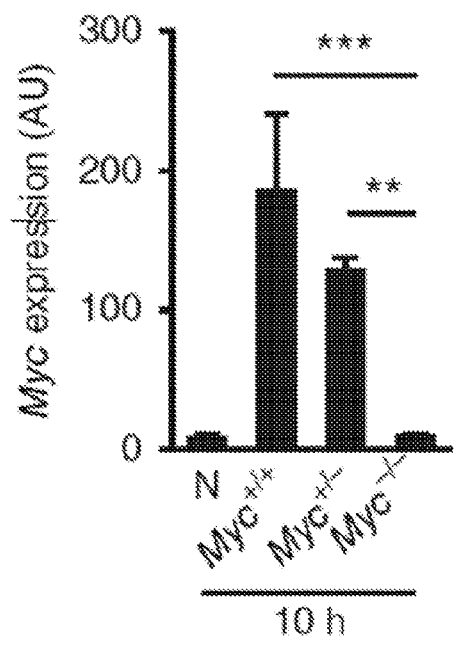
Figure 9C:
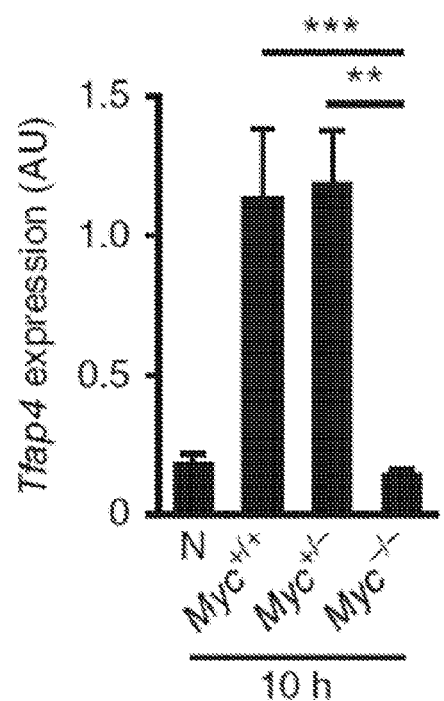
Figure 9D:
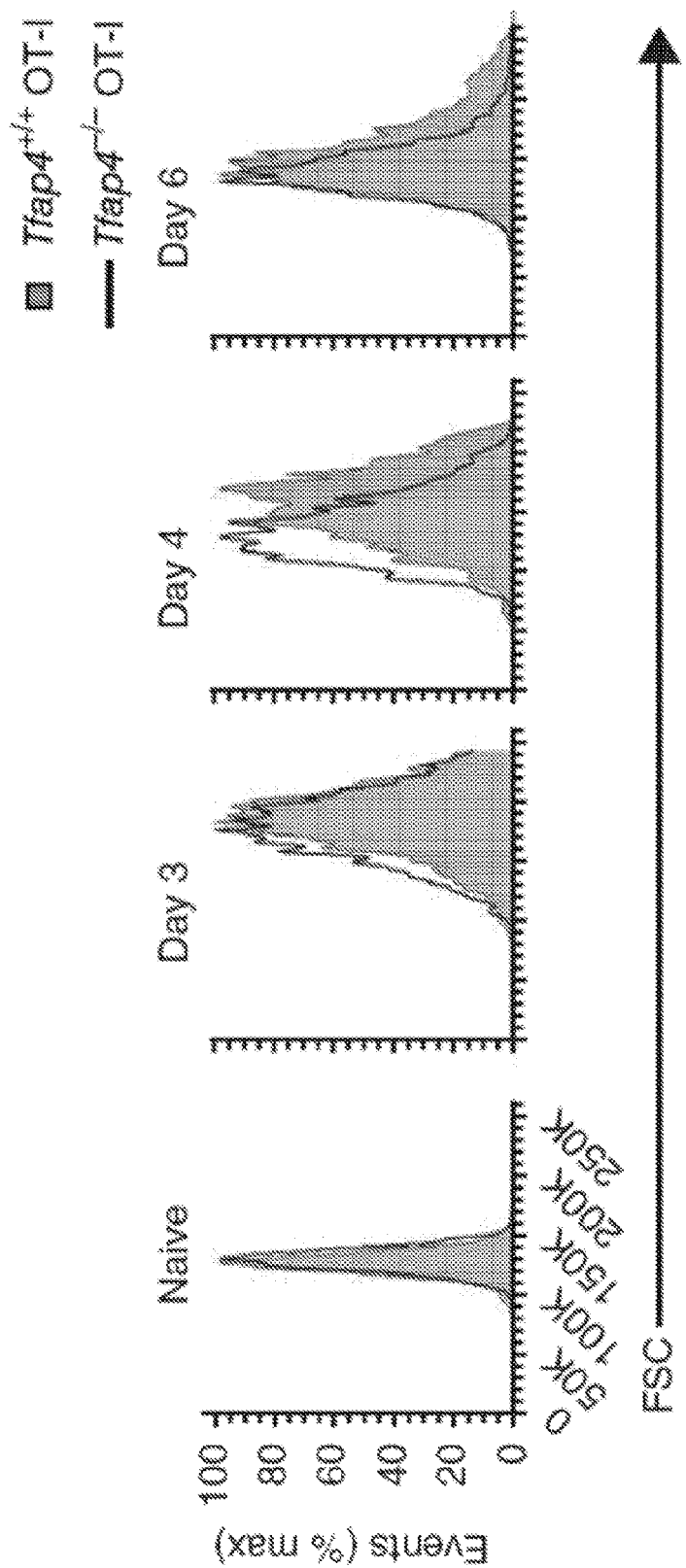
Figure 9E:
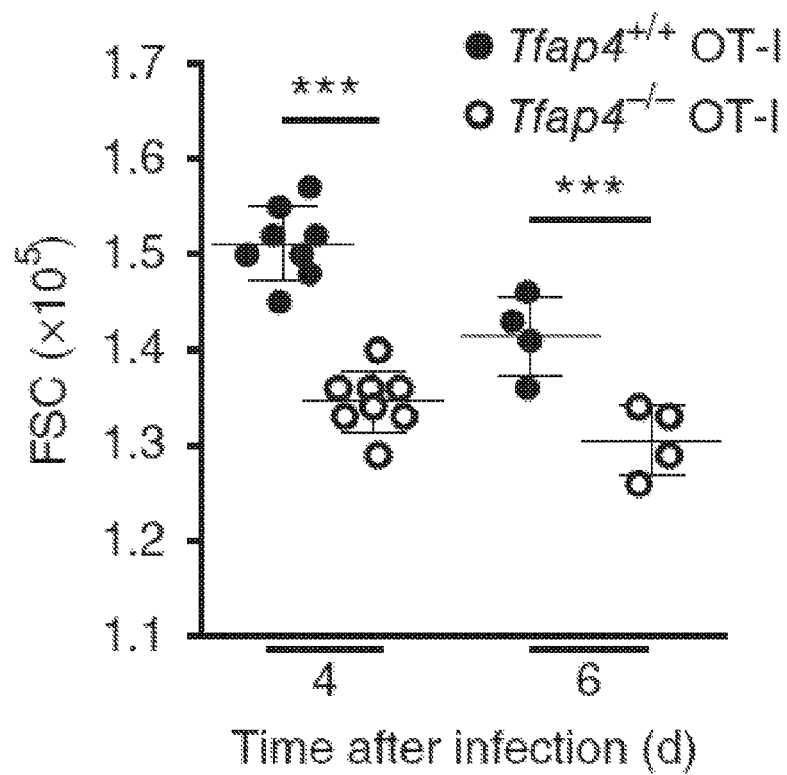
Figure 9F:
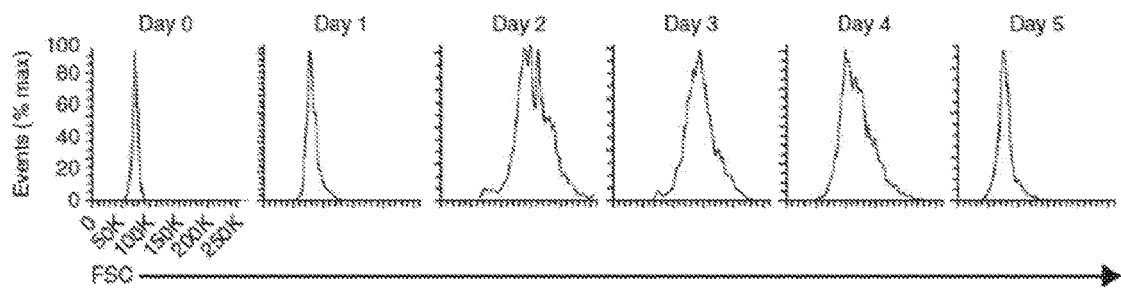
Figure 9G:
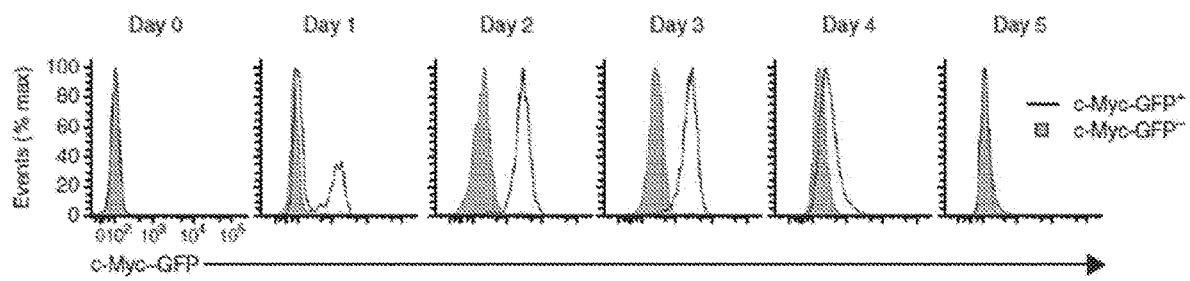
Figure 9H:
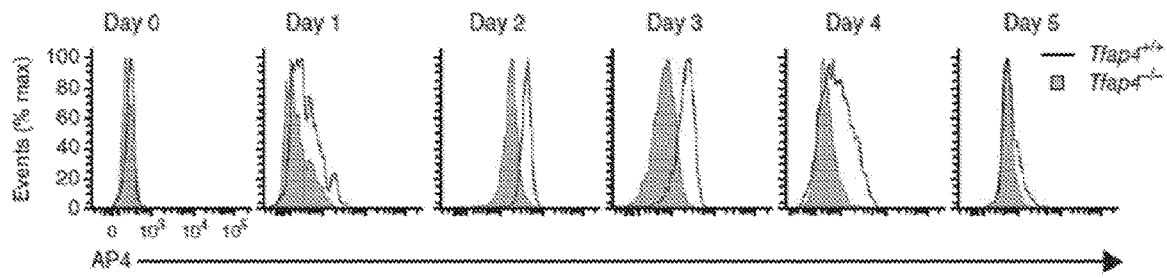
Figure 9I:
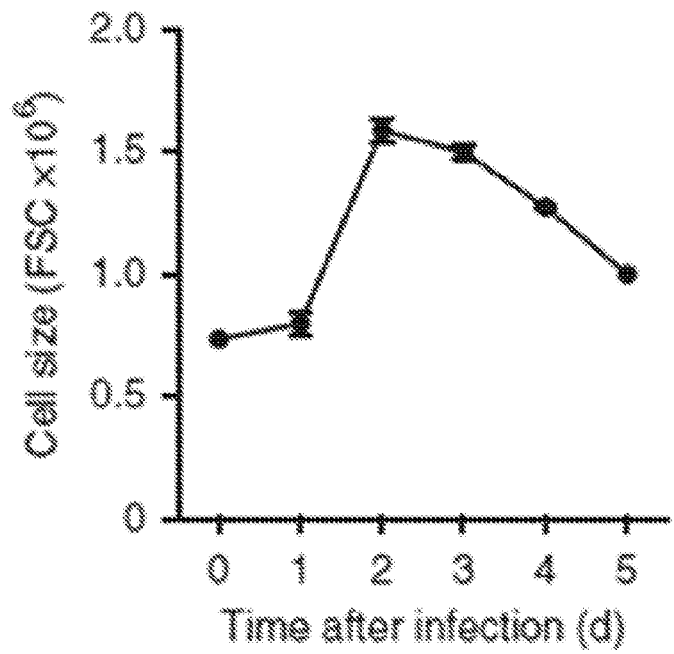
Figure 9J:
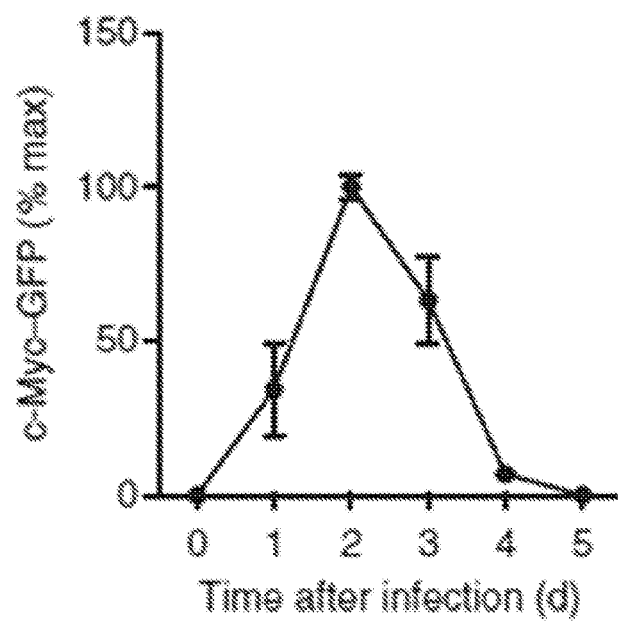
Figure 9K:
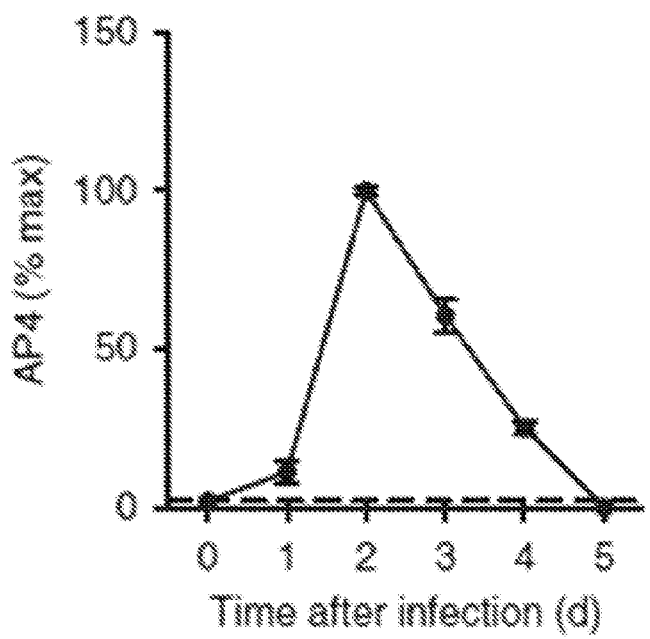
Figure 9L:
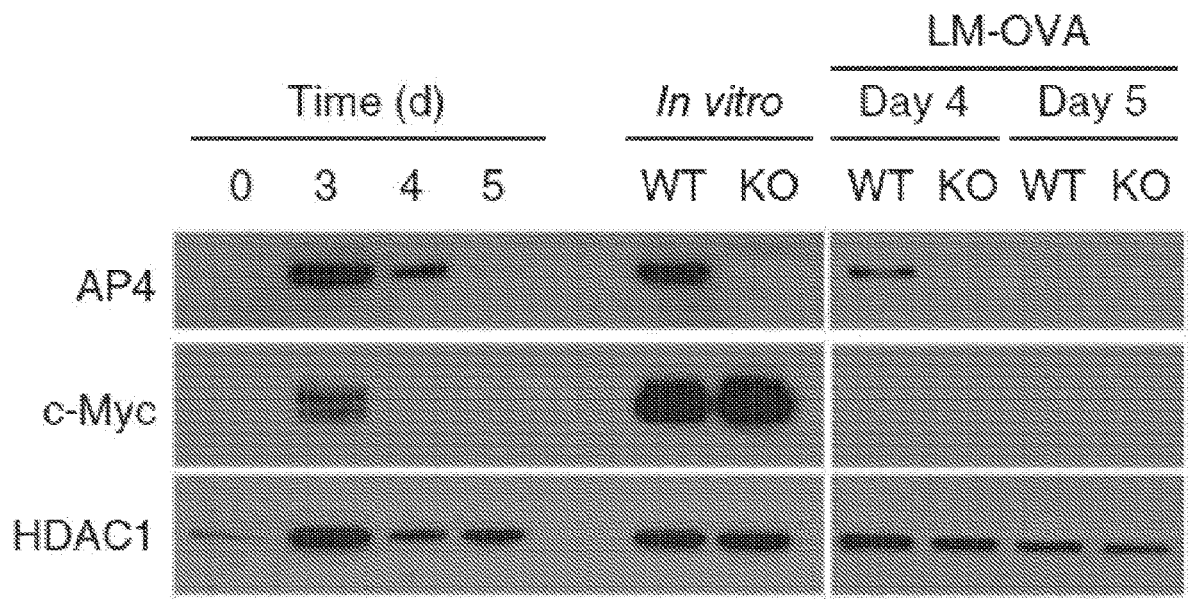
Figure 9M:
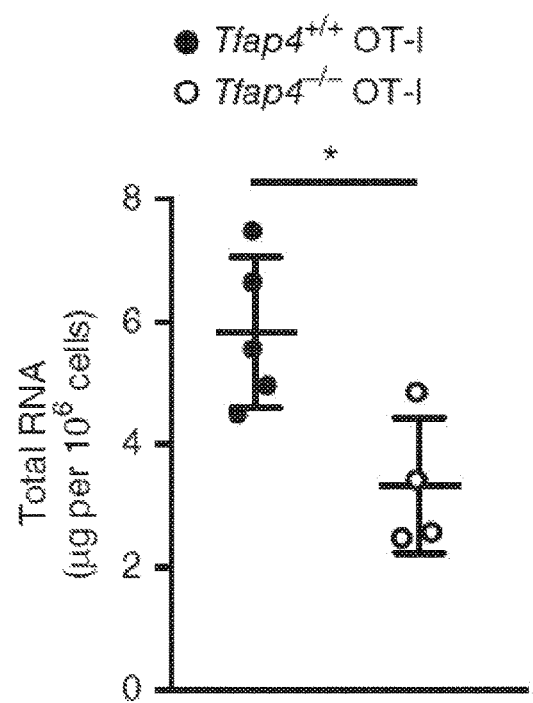
Figure 9N:
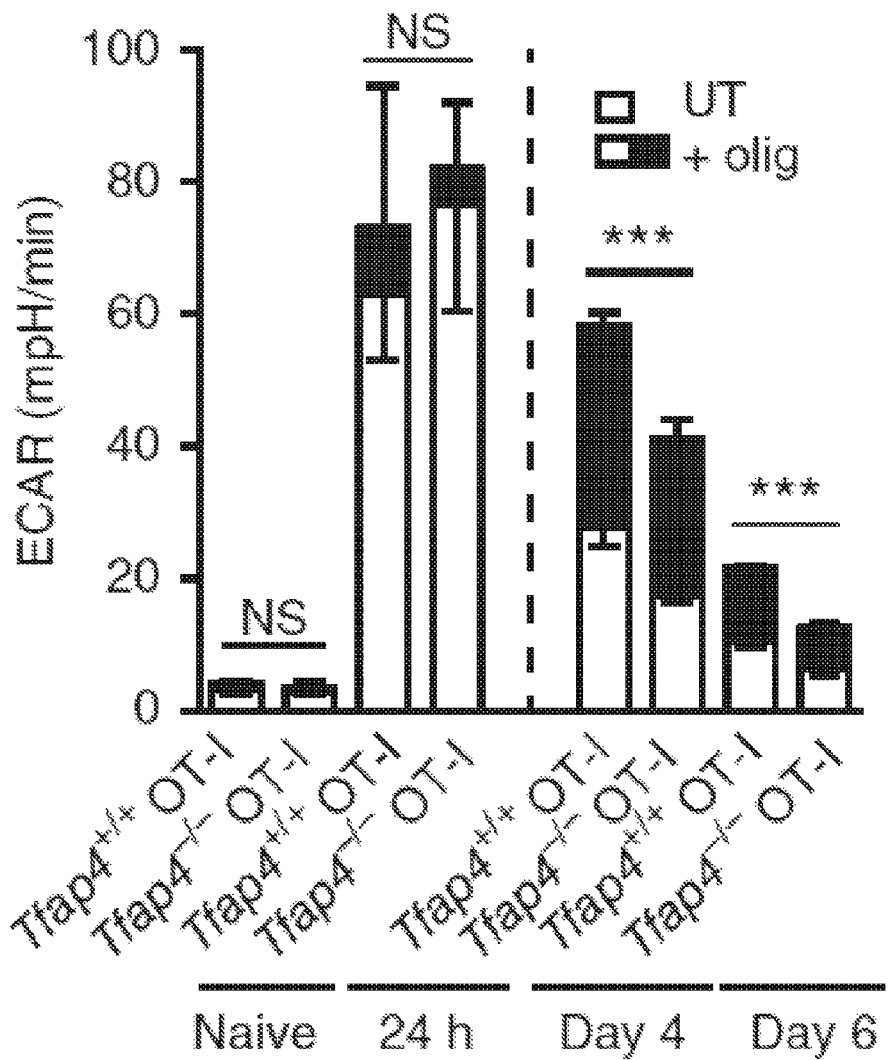
Figure 9O:
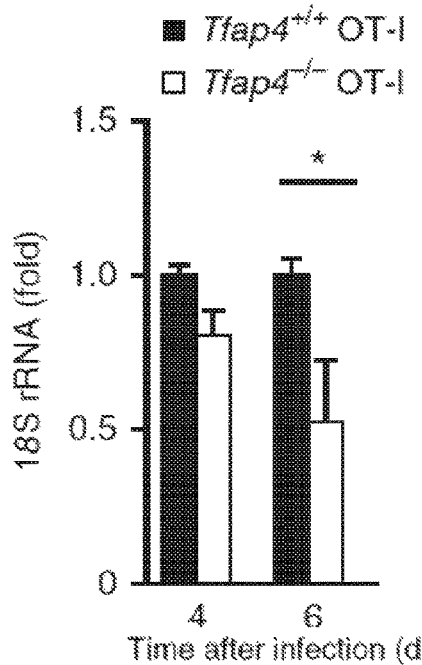
Figure 9P:
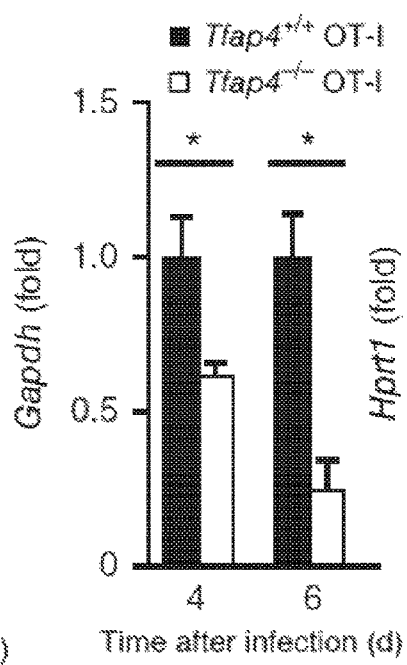
Figure 9Q:
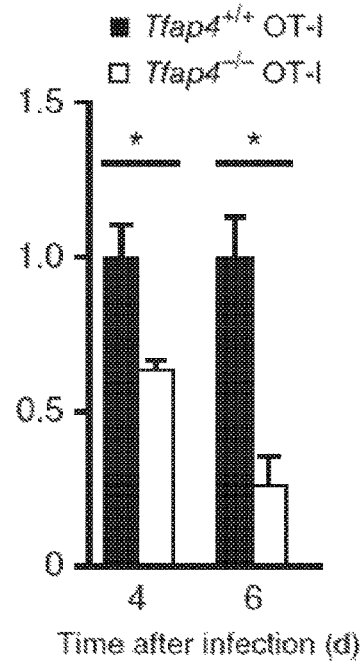
Figure 9R:
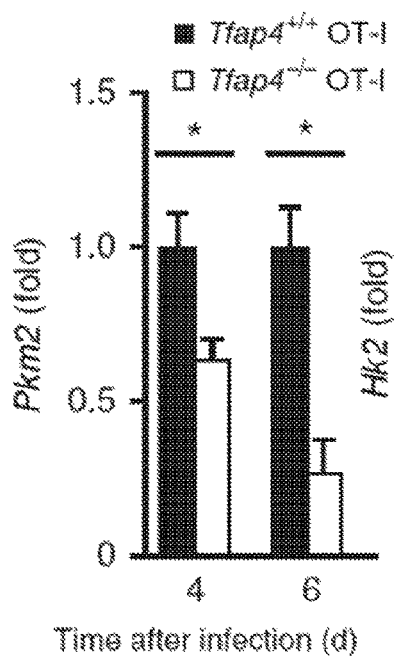
Figure 9S:
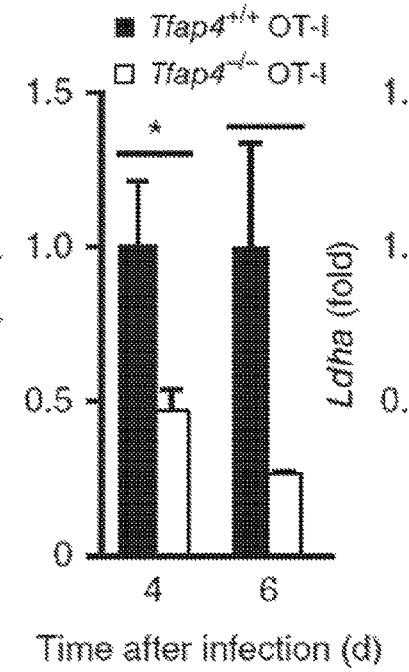
Figure 9T:
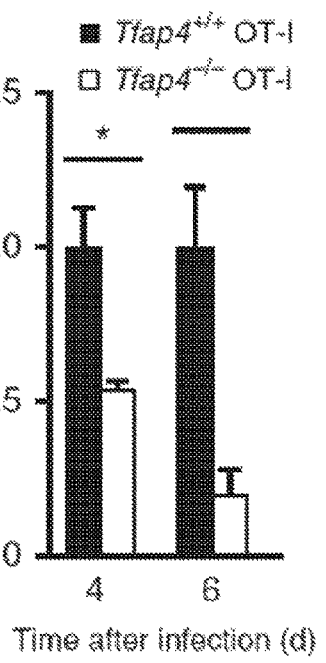

Example 5. AP4 Persists Longer than cMyc in Activated CD8$^+$ T Cells In Vivo and Supports Continued T Cell Activation after cMyc Downregulation In primary CD8$^+$ T cells, cMyc binds to two intronic sites (conserved between mouse and human) in the Tfap4 locus (FIG. 8). When cMyc was deleted using Tamoxifen-inducible CreERT$^2$, AP4 upregulation following activation was absent[4] (FIG. 9A). Together with the data showing normal priming and initial proliferation of Tfap4$^{-/-}$ CD8$^+$ T cells in the Myc phase, but a failure of continued rapid expansion in the post-Myc phase (FIG. 5A, FIG. 5B, FIG. 5C, FIG. 5D, FIG. 5E, FIG. 5F, FIG. 5G, FIG. 5H, FIG. 5I and FIG. 5J), it was hypothesized that cMyc-induced AP4 sustains the activated state of Ag-specific T cells in the post-Myc phase. Consistent with this hypothesis, AP4 protein expression was present longer than cMyc expression by 1-1.5 days, during which CD8$^+$ T cells divide 3-4 times[4] (FIG. 9A, FIG. 9B, and FIG. 9C), suggesting that CD8$^+$ T cells continue to pool material necessary for biogenesis due to AP4-mediated maintenance of cMyc target genes. Tfap4$^{-/-}$ cells in the post-Myc phase showed reduced cell size, RNA content, BrdU incorporation rates and glycolytic activity (FIG. 9D). In contrast, these differences were not observed during the Myc phase in the absence of AP4 (day 3 after Lm-Ova infection or day 1 after priming in vitro, FIG. 9A, FIG. 9B, FIG. 9C, FIG. 9D, FIG. 9E, FIG. 9F, FIG. 9G, FIG. 9H, FIG. 9I, FIG. 9J, FIG. 9K, FIG. 9L, FIG. 9M, FIG. 9N, FIG. 9O, FIG. 9P, FIG. 9Q, FIG. 9R, FIG. 9S, and FIG. 9T). These results collectively suggest that expression of AP4 for ~1.5 days after the cMyc decay compensates for loss of cMyc by augmenting expression of metabolic regulators to sustain proliferation after day 4.

Example 6. AP4 and Myc Functions Overlap

Figure 10A:
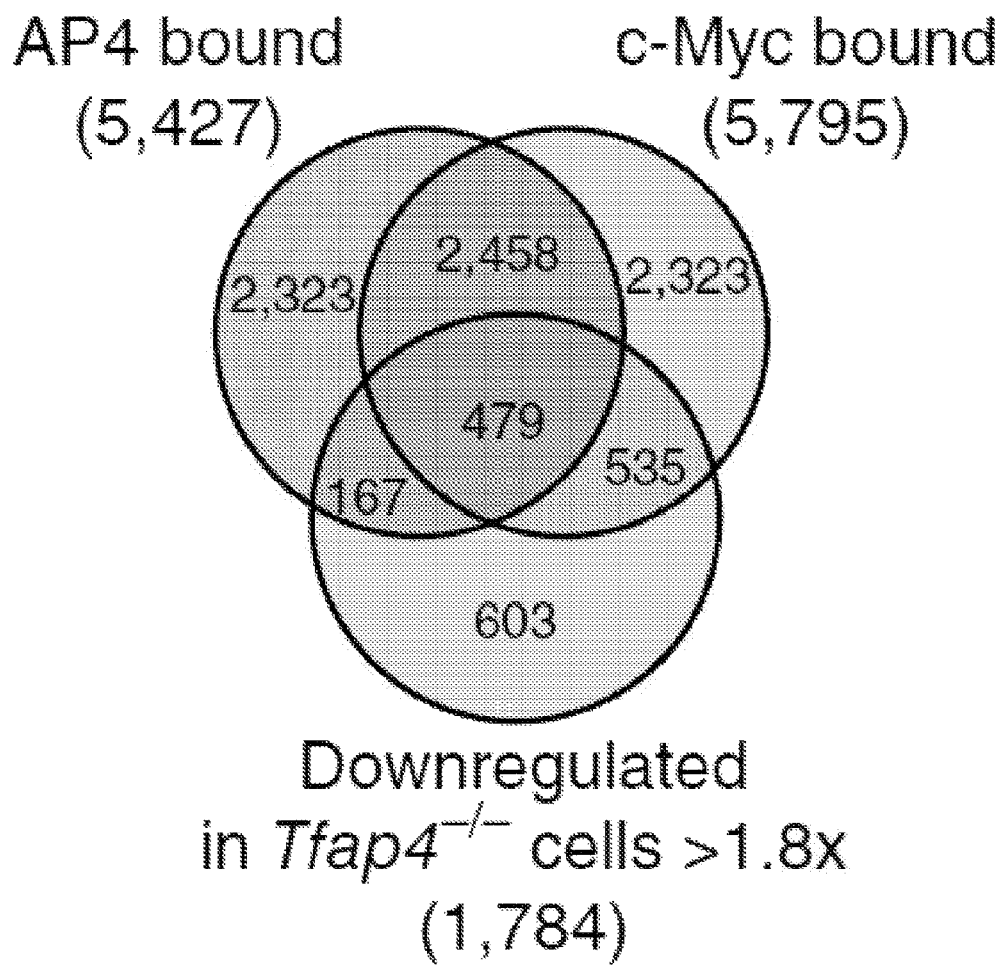
FIG. 10A, FIG. 10B, FIG. 10C, and FIG. 10D depict a venn diagram, schematic, graph and heat map showing the overlapping functions of AP4 and cMyc CD8$^+$ T cells in vitro.
Figure 10B:
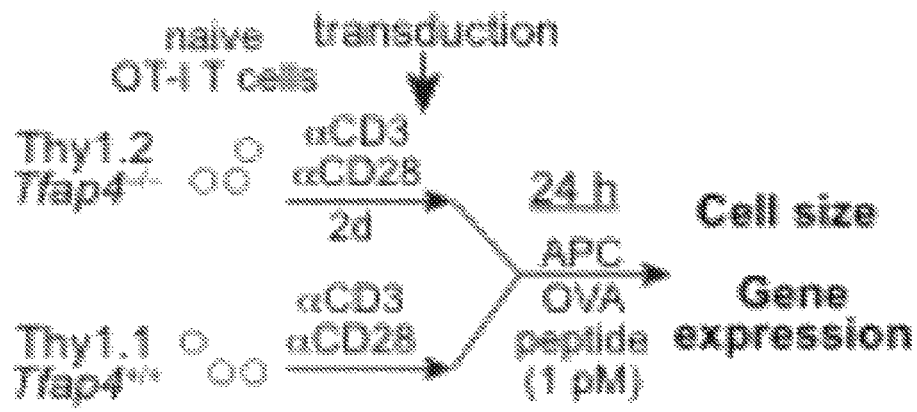
Figure 10C:
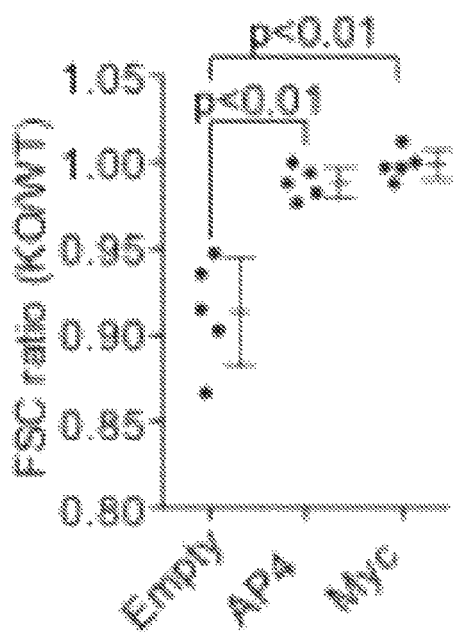
Figure 10D:
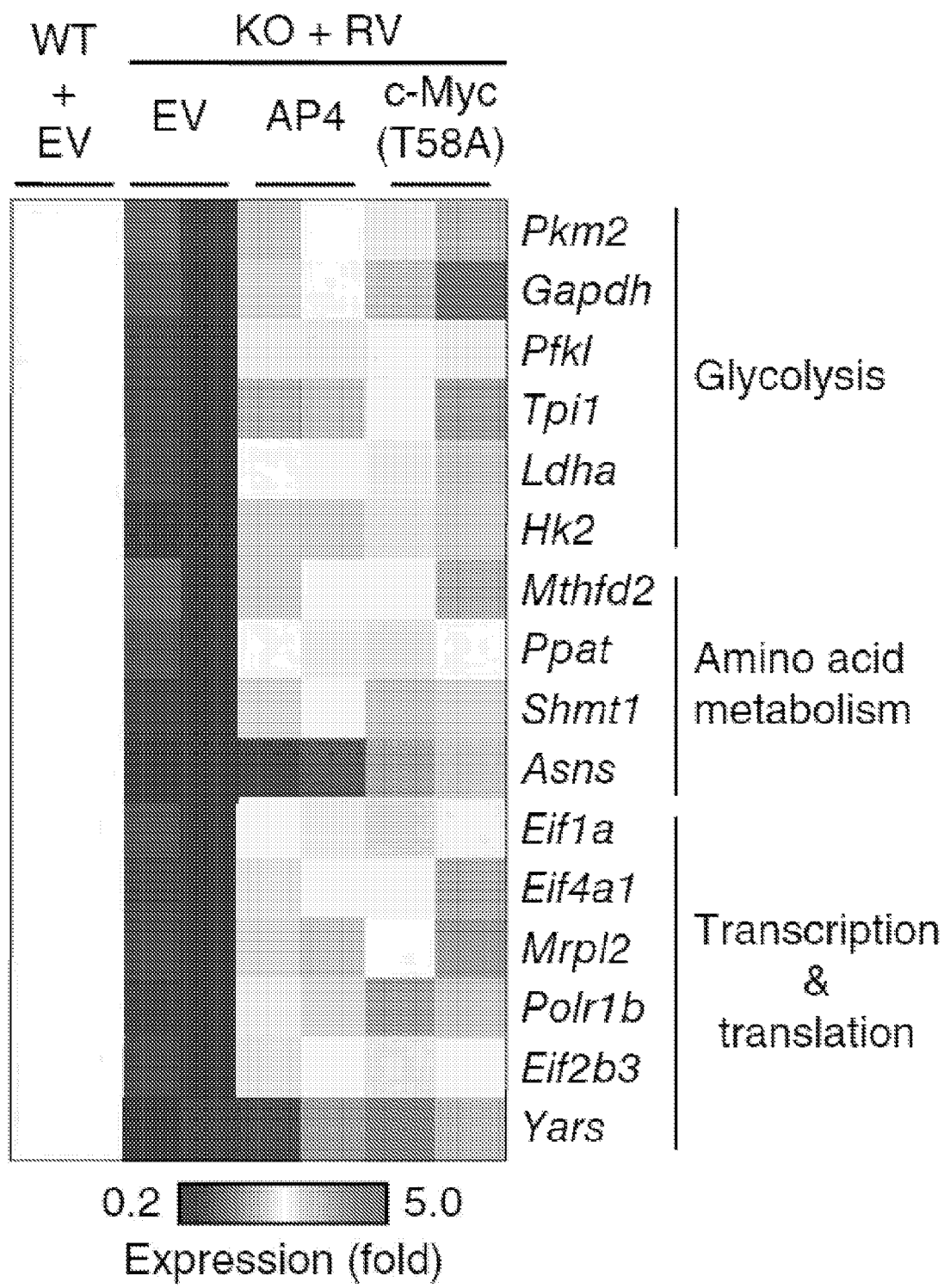
Figure 11A:
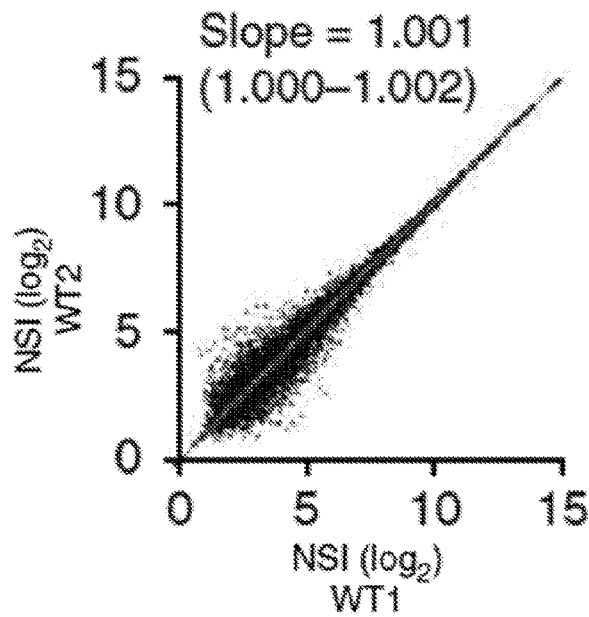
Figure 11B:
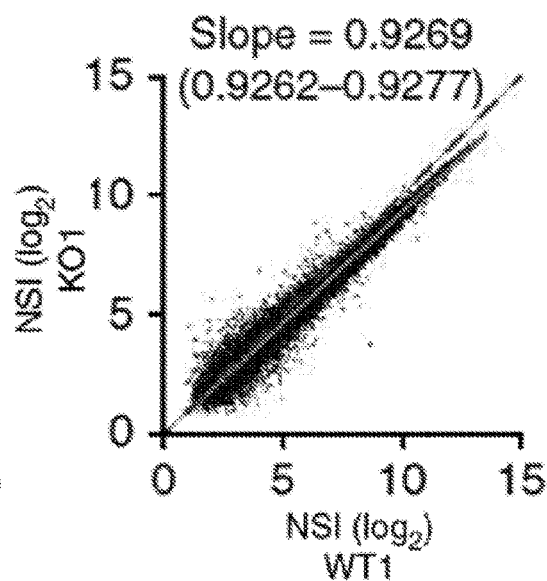
Figure 11C:
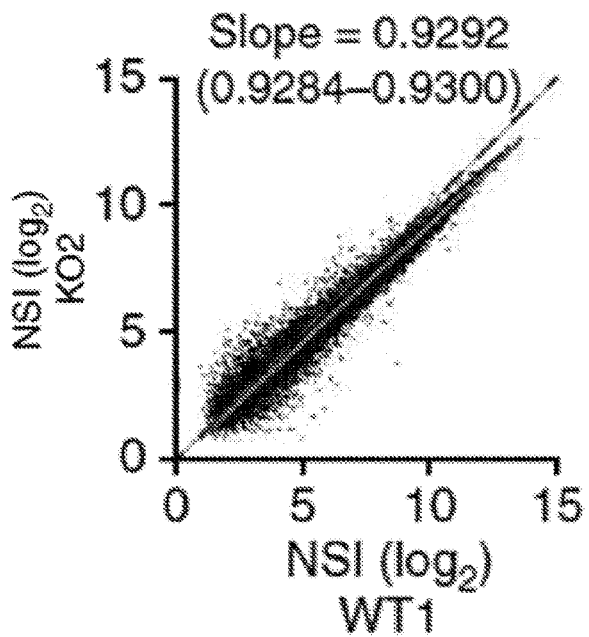
Figure 11D:
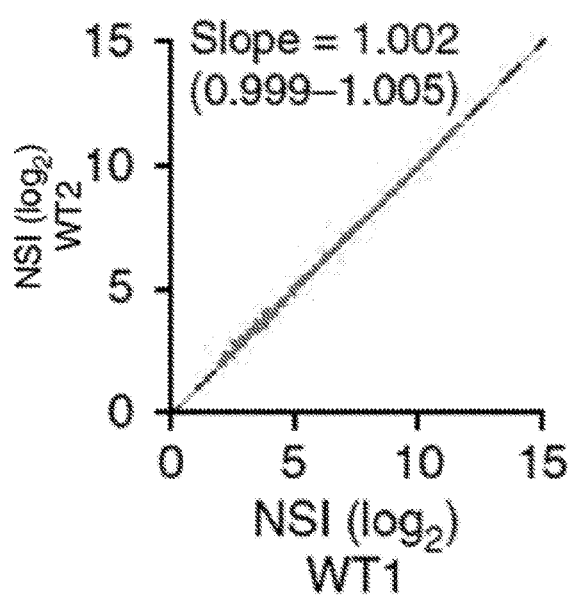
Figure 11G:
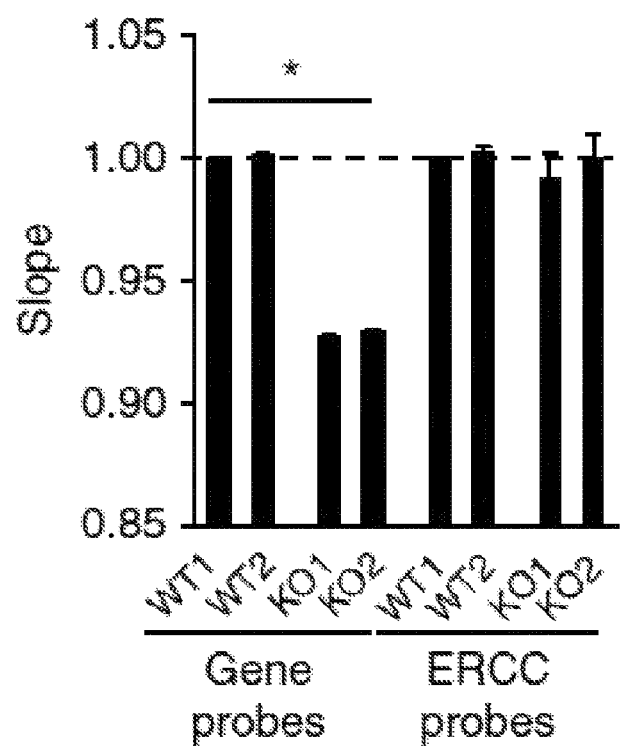
Figures 11H, 11I, 11J, 11K, 11L:
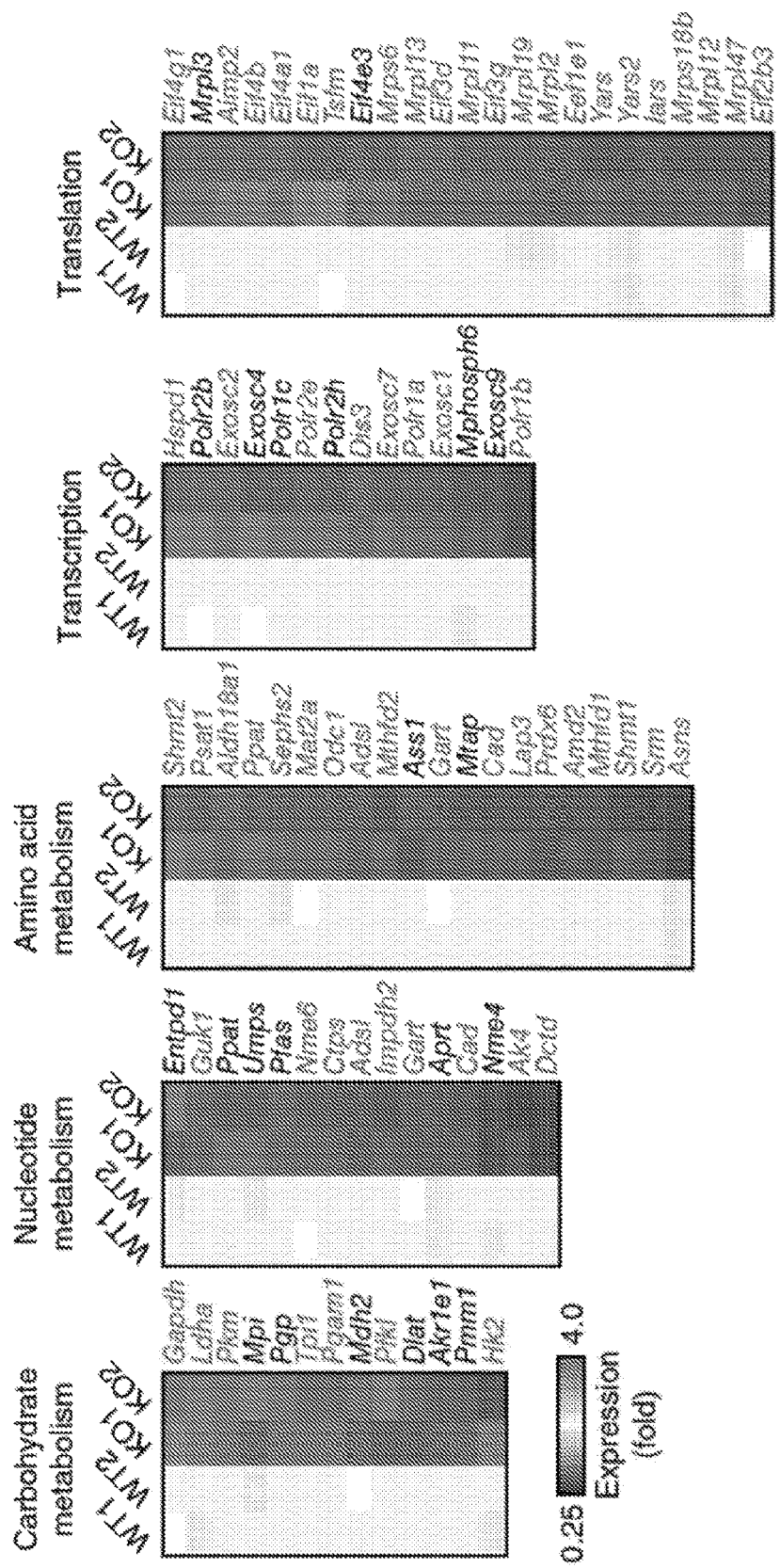
Figure 11M:
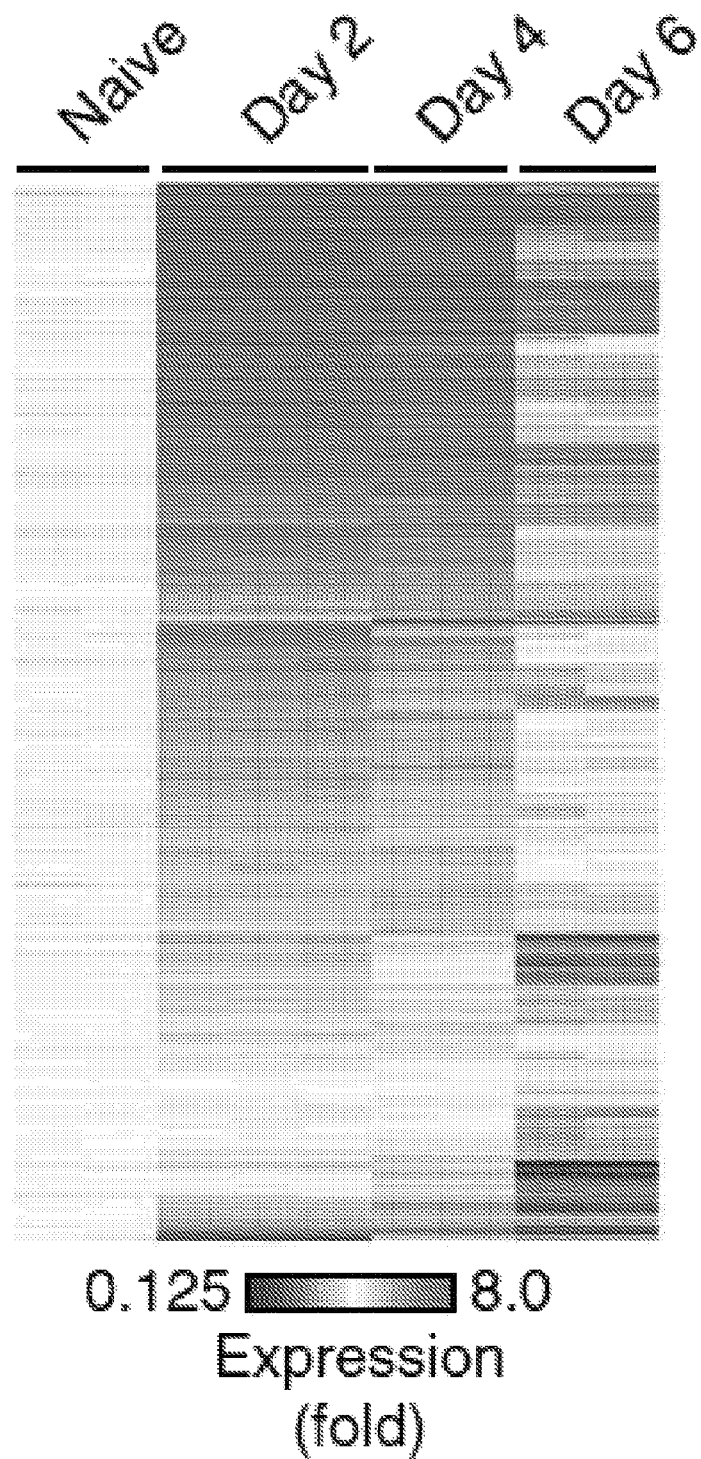
Figure 11N:
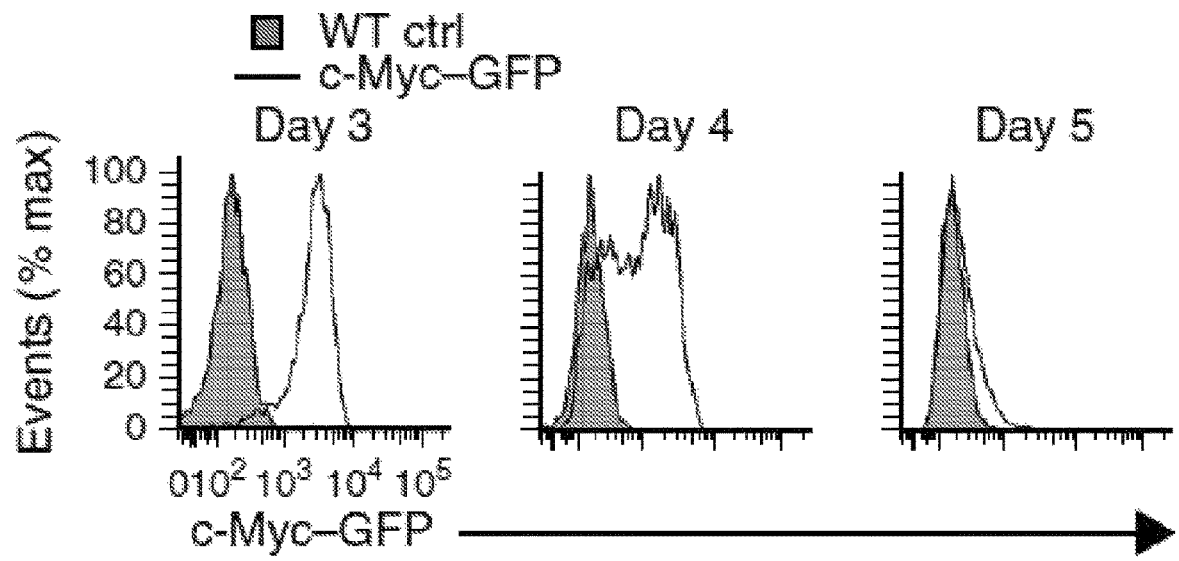
Figure 11O:
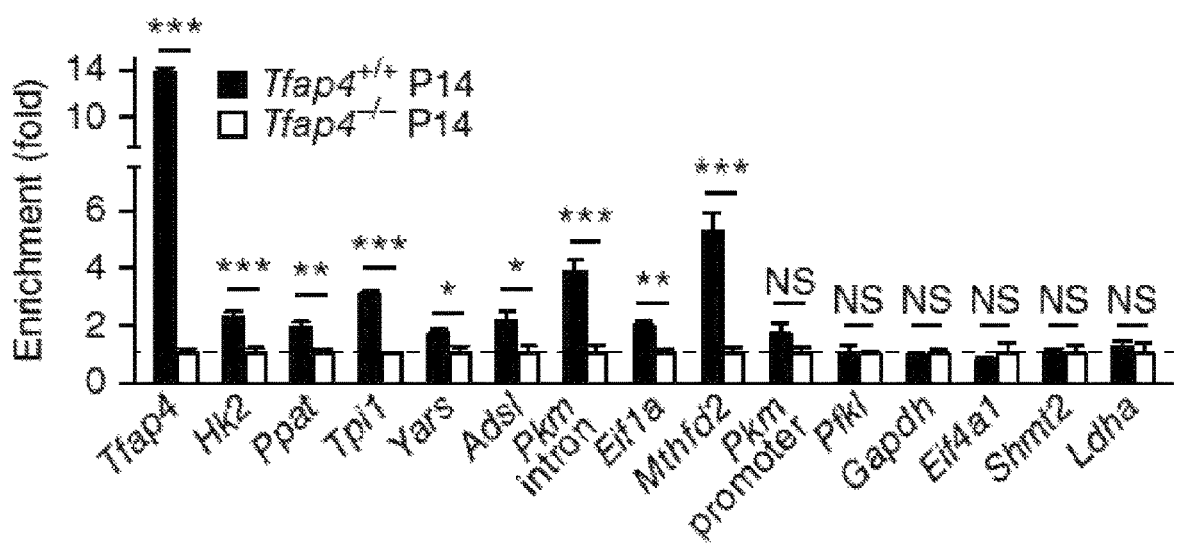

Next, it was assessed whether cMyc and AP4 regulate overlapping genes that are needed for T cell expansion by combining spike-in-normalized gene expression analysis[4,24] and ChIP-seq for AP4 and cMyc (FIG. 10A, FIG. 10B, FIG. 10C and FIG. 10D). Approximately 1,700 genes differentially expressed by >1.8-fold between Tfap4$^{-/-}$ versus WT OT-I cells in the post-Myc phase were identified using microarray (FIG. 11A, FIG. 11B, FIG. 11C, FIG. 11D, FIG. 11E, FIG. 11F, FIG. 11G, FIG. 11H, FIG. 11I, FIG. 11J, FIG. 11K, FIG. 11L, FIG. 11M, FIG. 11N, and FIG. 11O). Genes in metabolism, general transcription and translation pathways were over-represented. Combining this analysis with the ChIP-seq data, a large proportion of the metabolic, transcriptional and translational genes were common targets of AP4 and cMyc[4] (FIG. 10A). Retroviral (RV) overexpression of cMyc in Tfap4$^{-/-}$ CD8$^+$ T cells rescued the size defect and metabolic gene expression in vitro[4] (FIG. 10B, FIG. 10C, and FIG. 10D), further supporting redundant roles for AP4 and cMyc.

Example 7. cMyc is Insufficient to Promote Effector Differentiation

Figure 12C:
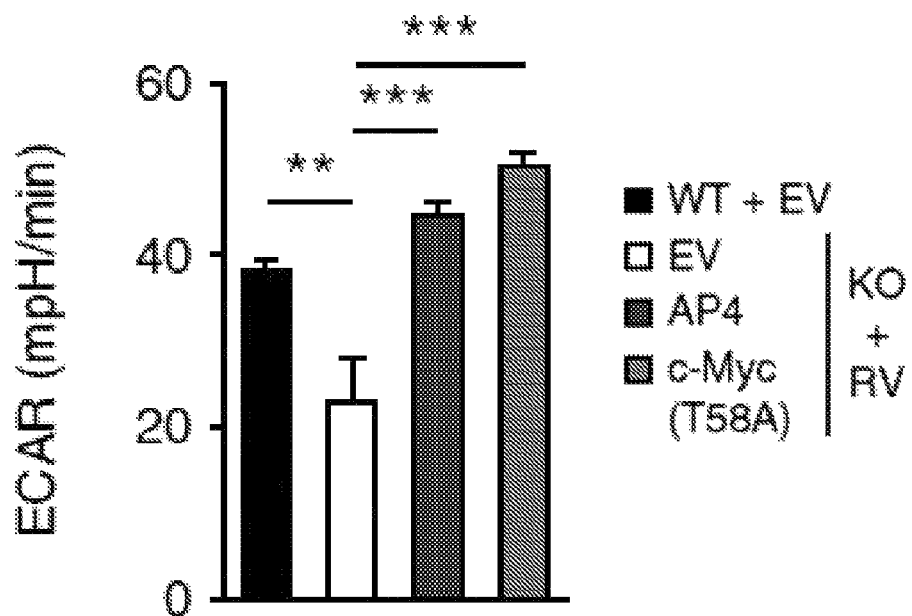
Figure 12D:
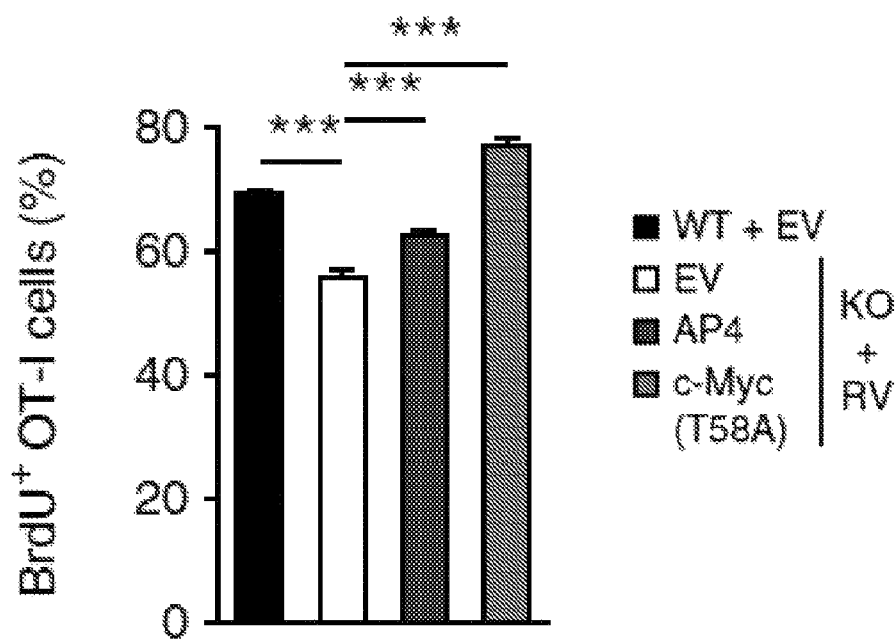
Figure 12E:
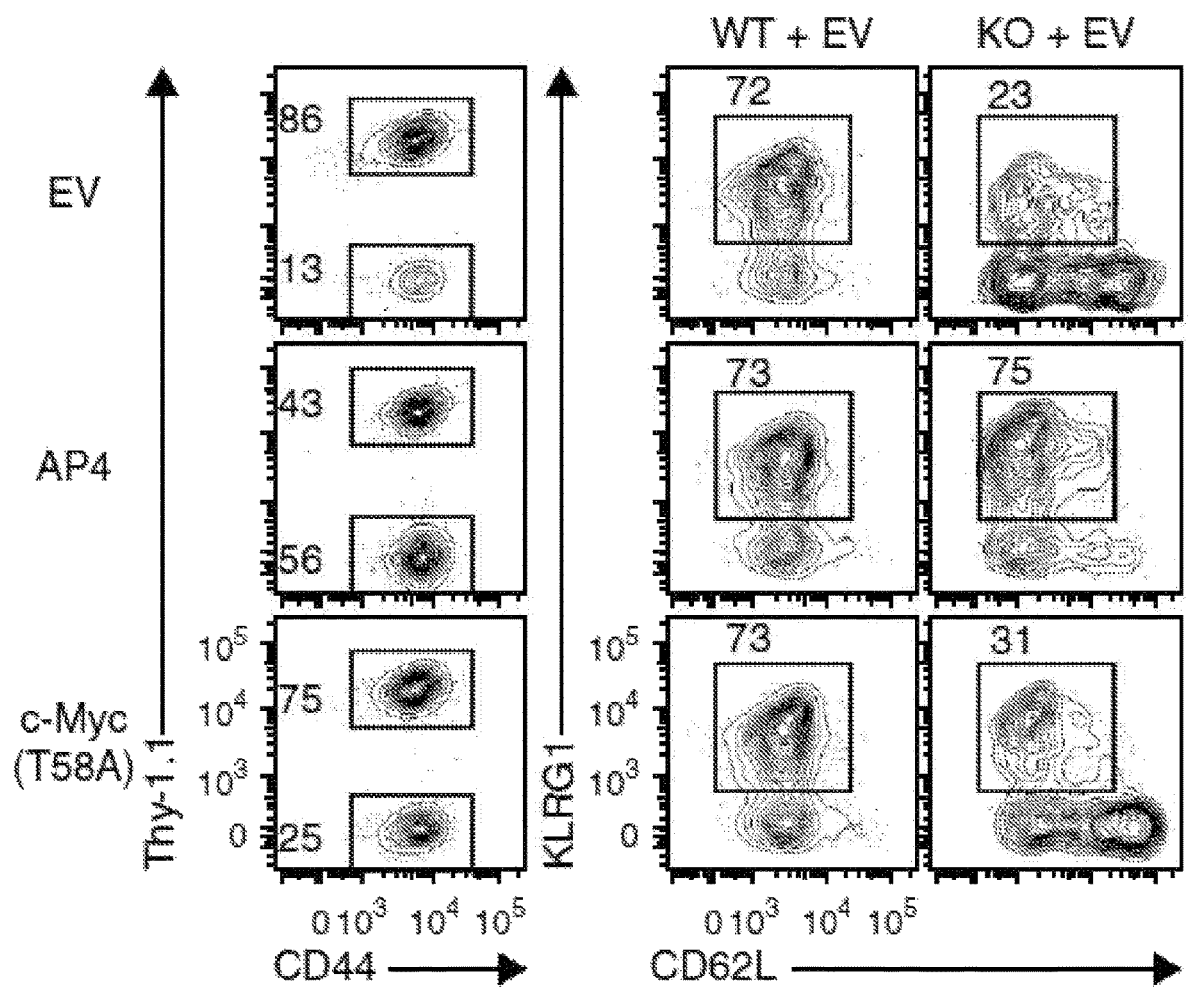
Figure 12F:
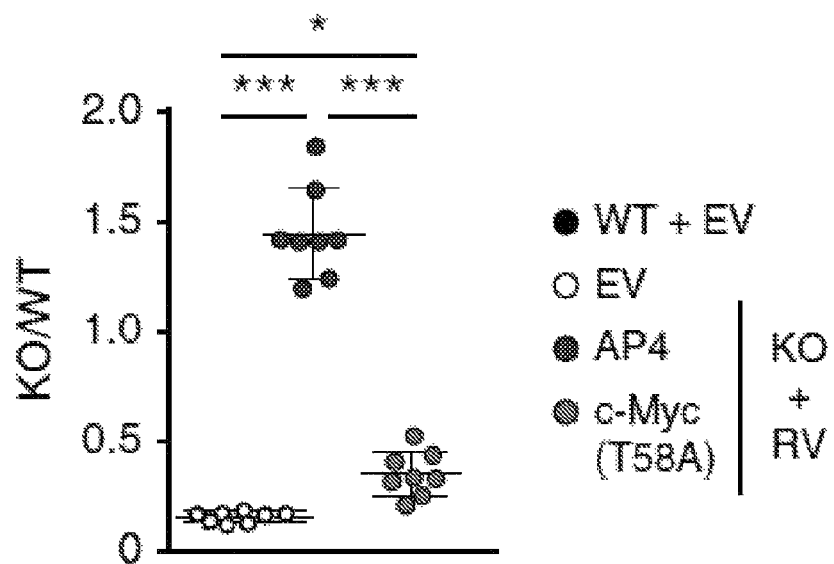
Figure 12G:
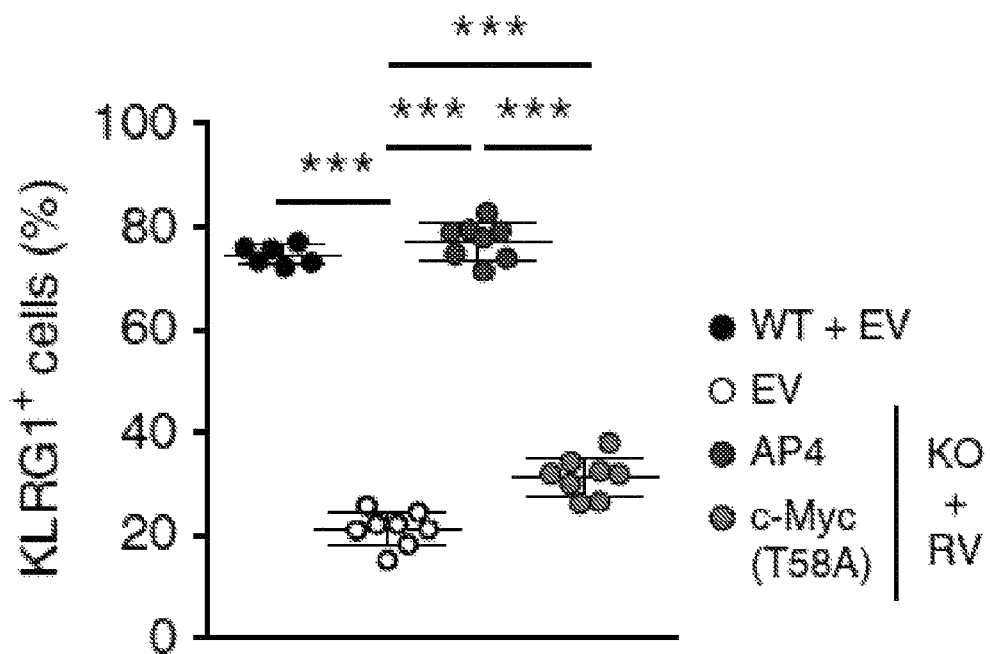
Figure 12H:
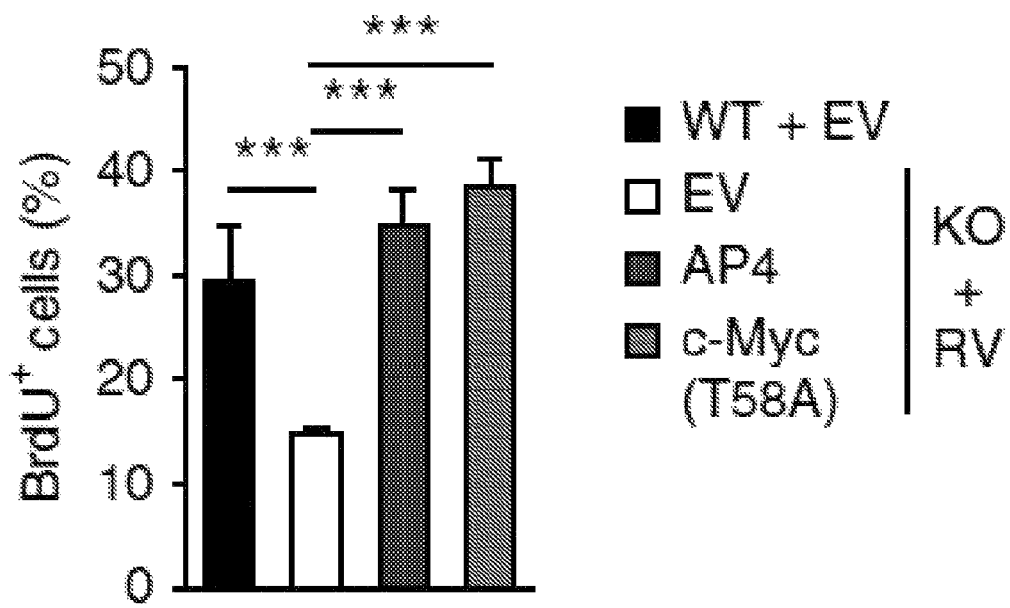
Figure 12I:
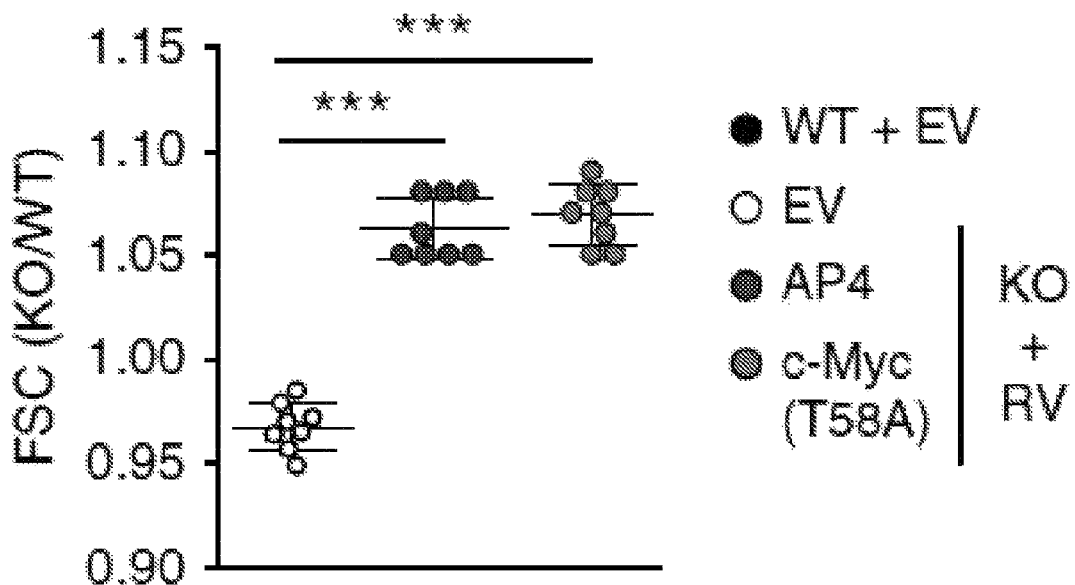

The data suggested that AP4 and cMyc have overlapping regulatory functions for clonal expansion. Next, it was tested whether RV expression of cMyc in Tfap4$^{-/-}$ Ag-specific T cells also rescued their expansion and effector differentiation in vivo. AP4 or cMyc was expressed in Tfap4$^{-/-}$ OT-I cells without TCR stimulation, and were transferred into congenic host mice with control empty RV-infected congenic Tfap4$^{+/+}$ OT-I cells[4]. Effector differentiation was assessed by surface KLRG1 expression and downregulation of CD62L six days after Lm-Ova infection. As shown in FIG. 12F, although AP4-RV increased KLRG1$^+$ cells and decreased CD62L$^+$ cells, cMyc had little effect.

Based on these data, it was concluded that AP4 1) prolongs the activated state of Ag-specific CD8$^+$ T cells to allow for their sustained proliferation, and 2) promotes their effector differentiation in a cMyc-independent manner. A temporally-regulated hand-off between the two factors facilitates effective CD8$^+$ T cell responses. Why do T cells utilize cMyc only briefly to expand their clonal frequencies? It is hypothesized that cMyc is absolutely required for initiation of T cell proliferation, but prolonged cMyc expression without the "hand-off" inhibits accumulation of Ag-specific T cells and amplification of immune responses. Furthermore, a failed cMyc-AP4 hand-off may dysregulate T cell responses during chronic viral infection or in tumor microenvironments. These hypotheses will be tested by defining the specific requirements for cMyc in T cell proliferation, and how post-Myc expression of AP4 is sustained for enhanced clonal expansion and effector differentiation. Finally, the mechanisms that cause T cell dysregulation or exhaustion during persistent viral infection or in tumor microenvironments will be studied, focusing on perturbations to the cMyc-AP4 axis. These studies will provide insights into a new transcription factor cascade that both enhances and maintains T cell immune responses.

Figure 13A:
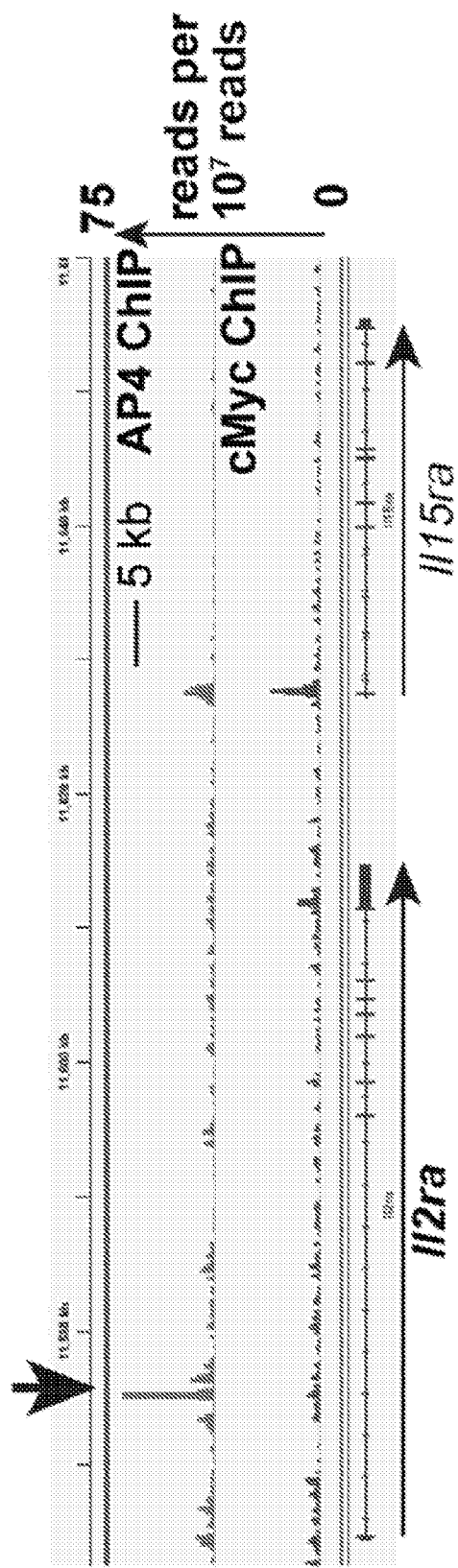
FIG. 13A, FIG. 13B, FIG. 13C, and FIG. 13D depict a schematic, graph and flow cytometry plots showing that Il24a is a directed target of AP4, but not cMyc, and down-regulated in Tfap4$^{-/-}$ CD8+ T cells in post-Myc phase.
Figure 13B:
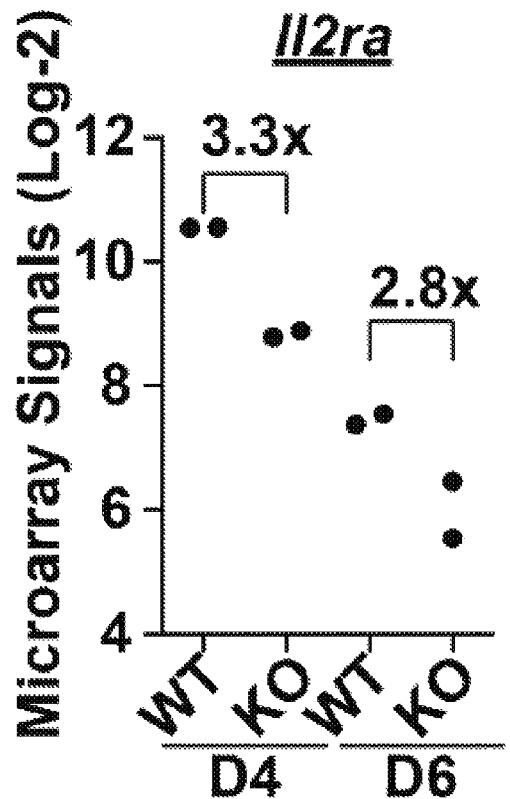
Figure 13C:
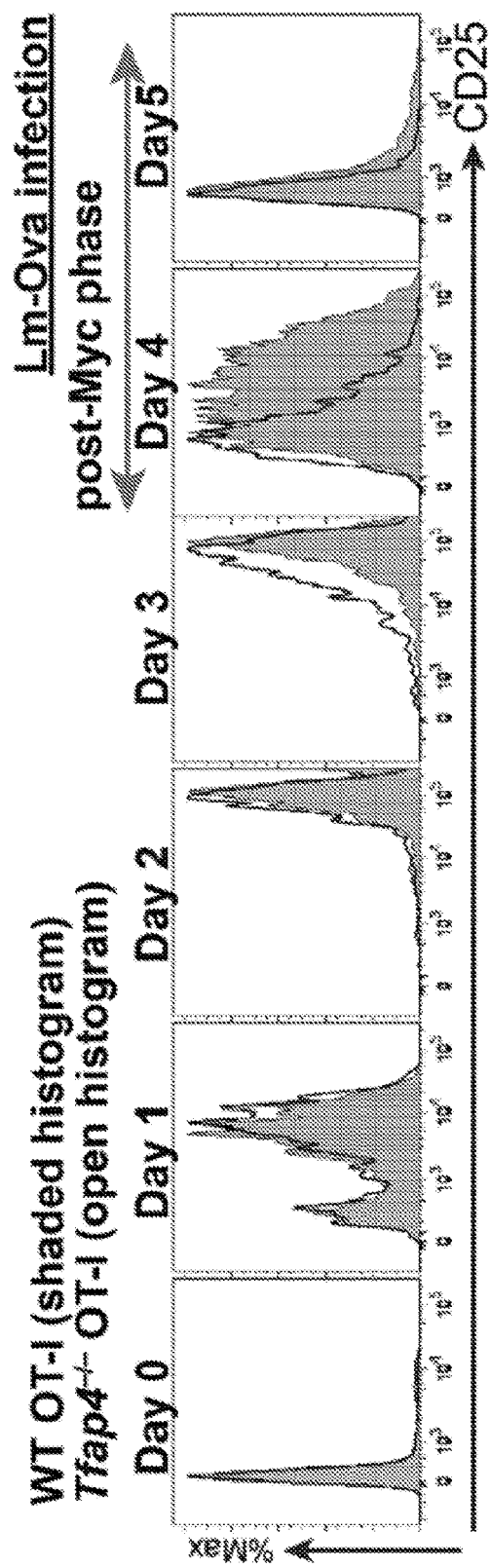
Figure 13D:
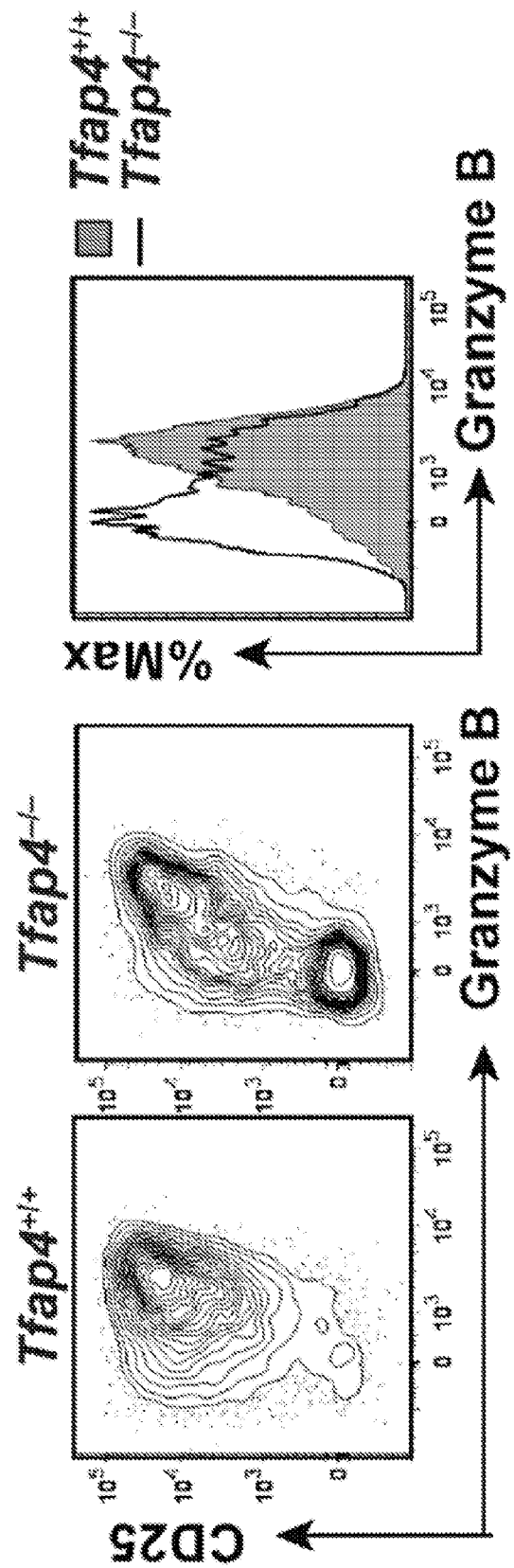
Figure 14A:
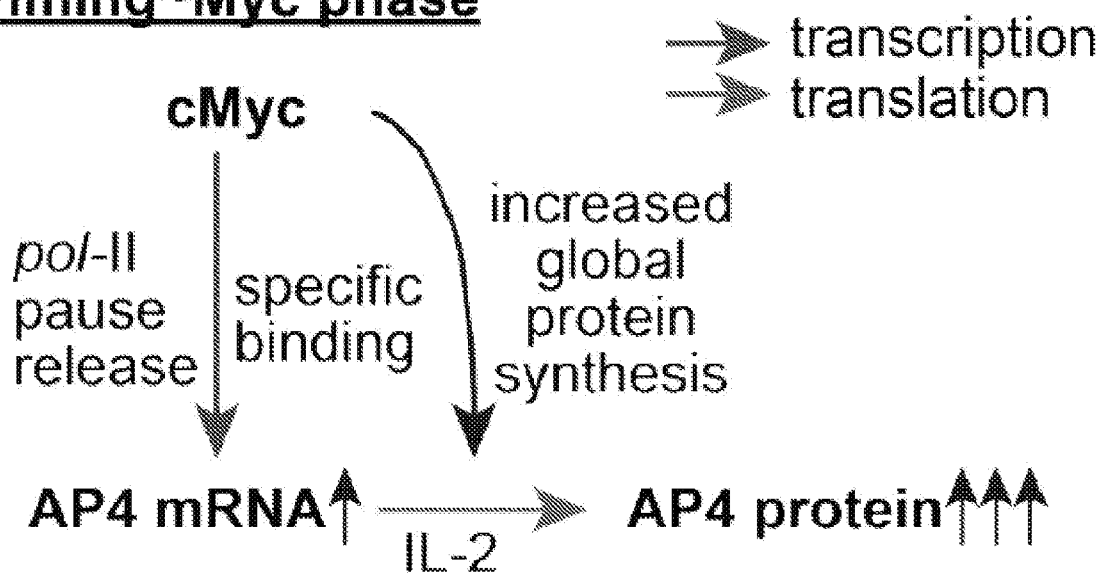
FIG. 14A and FIG. 14B depict models for the maintenance of post-Myc AP4 expression and the regulation of effector differentiation of CD8+ T cells by an AP4-IL2 feedforward loop.
Figure 14B:
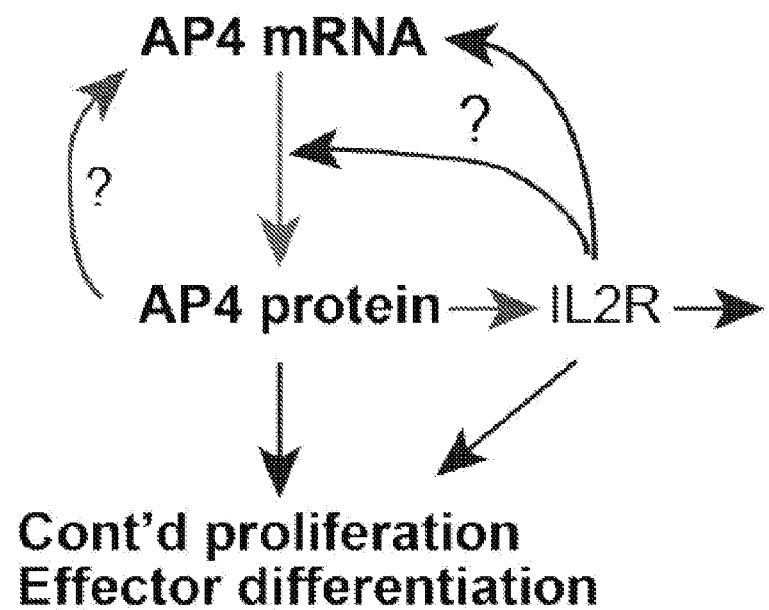

Example 8. Define the Roles of AP4-IL2Rα Feed-Forward Circuits in Post-Myc Expression of AP4 and Differentiation of Effector and Memory CD8$^+$ T Cells AP4 expression is sustained longer than cMyc and required for differentiation of effector CD8$^+$ cells following acute infection[4]. In this aim, the mechanisms by which AP4 protein is maintained after cMyc decays and how this contributes to effector differentiation will be dissected. The microarray and ChIP-seq datasets will be used to identify key AP4-specific target genes that presumably are important for sustaining its expression at the transcriptional or translational levels, as well as for effector differentiation. Genes were screened for that were 1) downregulated in Tfap4$^{-/-}$ CD8$^+$ T cells compared to WT CD8$^+$ T cells, 2) directly bound by AP4 but not cMyc, and 3) implicated in protein translation and effector differentiation of CD8$^+$ T cells. Whereas AP4 binds its own promoter (FIG. 8, FIG. 9A, FIG. 9B, FIG. 9C, FIG. 9D, FIG. 9E, FIG. 9F, FIG. 9G, FIG. 9H, FIG. 9I, FIG. 9J, FIG. 9K, FIG. 9L, FIG. 9M, FIG. 9N, FIG. 9O, FIG. 9P, FIG. 9Q, FIG. 9R, FIG. 9S, and FIG. 9T), two intriguing genes, Slc7a5 (encoding the leucine transporter required for activation of mTORC1) and Il2ra (encoding the high-affinity IL-2R subunit CD25) were uncovered as direct AP4-specific targets (FIG. 13A, and FIG. 13B). These binding peaks colocalize with DNaseI hypersensitivity sites (data not shown). Slc7a5 is upregulated in activated T cells and is required for T cell proliferation.[33] Sustained IL-2R expression enhances effector differentiation of CD8$^+$ T cells.[12,16] While AP4 is dispensable for initial CD25 upregulation during priming (FIG. 13C, Days 1-2), CD25 downregulation occurs rapidly in Tfap4$^{-/-}$ CD8$^+$ T cells (FIG. 13C, Days 3-4). Furthermore, Tfap4$^{-/-}$ OT-I cells expressed substantially reduced Granzyme B, which correlated with lower CD25 expression (FIG. 13D). Collectively, these data suggest that AP4 is required for sustained IL-2Rα/CD25 expression and effector differentiation. As shown in FIG. 1, IL-2R signals are required for accumulation of AP4 protein. As such, it is hypothesized that an AP4-IL-2Rα feed-forward mechanism enhances effector differentiation of CD8$^+$ T cells, which may be further augmented by SLC7A5 and auto-regulation of AP4 (FIG. 14A and FIG. 14B). This gene regulatory network may also influence the development of potent memory CD8$^+$ T cells, a process known to require IL-2R signaling during primary responses[15]. These studies will establish the central roles of AP4 in the regulation of acute and long-term immunity against infections.

Example 9. Determine Whether AP4 Directly Regulates Sustained Ilra/CD25 in Activated CD8$^+$ T Cells It will first be tested whether AP4 directly sustains CD25 expression in CD8$^+$ T cells. Purified Tfap4$^{-/-}$ and WT naive CD8$^+$ T cells will be stimulated for 2 days with anti-CD3/CD28 antibodies and subsequently incubated in 100 U/ml of IL-2 for 1 day. At this point, all cells express CD25 at a high level. The activated T cells will be split and exposed to different concentrations of IL-2 (100 U/ml to 1U/ml) for 12 hours. Il2ra/CD25 expression will be compared at the protein and mRNA levels. To determine whether the AP4 binding site within the Il2ra locus contributes to enhancer activity for sustaining Il2ra expression, an RV reporter construct with a 1 kb fragment that spans the intact AP4 binding site or one with a mutated binding site will be made. Cultured primary CD8$^+$ T cells will be infected with the RV reporters and passaged under the conditions described above to monitor enhancer activity in vitro. Cytokine-primed OT-I cells without TCR stimulation will also be transduced, followed by analysis of reporter expression in vivo, as described (FIG. 11A, FIG. 11B, FIG. 11C, FIG. 11D, FIG. 11E, FIG. 11F, FIG. 11G, FIG. 11H, FIG. 11I, FIG. 11J, FIG. 11K, FIG. 11L, FIG. 11M, FIG. 11N, and FIG. 11O).

These experiments will establish that AP4 directly regulates IL-2Rα expression. Data has been obtained showing that AP4 overexpression is sufficient to sustain CD25 expression in low IL-2 conditions, and therefore it is predicted that AP4 is required for sustained CD25 expression via direct regulation. While the reporter assays mentioned above are a valid test for the hypothesis, the AP4-bound element from the endogenous Il2ra locus will also be mutated using CRISPR/Cas9 to test whether it is necessary for sustained CD25 expression. In this case, RV constructs expressing a guide RNA targeting the AP4 binding site will be engineered and \CD8$^+$ T cells from Cas9 transgenic mice (JAX) will be transduced. This would be a direct assay to test the hypothesis, but optimization of guide RNA with sufficient editing efficiency for analysis of pooled populations will be needed.

Example 10. Define Pathways by which the AP4-IL-2R Loop Regulates Differentiation of Effector CD8+ T Cells While effector differentiation of Tfap4$^{-/-}$ CD8+ T cells is impaired (FIG. 3C, FIG. 3D, FIG. 3E, FIG. 3F, FIG. 3G, FIG. 13A, FIG. 13B, FIG. 13C, FIG. 13D, and FIG. 15), it is unclear whether the defect is a direct consequence of AP4 deletion, premature downregulation of IL-2Rα, or both. To determine whether altered IL-2R signaling due to reduced expression of the high-affinity receptor is responsible for the changes in gene expression and effector functions in the absence of AP4, rescue experiments will be performed. To bypass the requirement for CD25, an IL-2/anti-IL-2 (Clone S4B6) immune-complex (IL2-IC) will be used that can bind directly to the IL-2Rβ/γ complex with high affinity.[36] Tfap4$^{-/-}$ or WT OT-I cells will be transferred into congenic host mice that will subsequently be infected with Lm-Ova. The infected host mice will be treated with IL2-IC on days 2-4 as previously described[15], and expression of effector-associated genes and memory-associated genes in sorted OT-I donor cells will be measured. Expression of IL-2Rβ/γ was not altered in Tfap4$^{-/-}$ CD8+ T cells (data not shown).

As a complementary approach, AP4 will be expressed in Il2ra$^{-/-}$ OT-I cells. As shown in FIG. 2A, FIG. 2B, FIG. 2C, FIG. 2D, FIG. 2E, FIG. 2F, FIG. 2G, FIG. 2H, FIG. 2I, and FIG. 2J, AP4 protein levels are dependent on IL-2 signals[4]. To facilitate AP4 protein accumulation in the absence of IL-2Rα, a stabilized form of AP4 has been generated by replacing the Ser139 residue with Ala (AP4$^{S139A}$ or sAP4). sAP4 is resistant to degradation and promotes sustained CD25 expression (FIG. 16A, FIG. 16B, and FIG. 16C), validating its functionality. CD45.2/CD90.2 OT-I; Il2ra$^{-/-}$ cells (harvested from mixed bone marrow chimera) will be transduced either with empty RV or one expressing sAP4 without TCR stimulation as described,[4] followed by co-transfer with CD45.2/CD90.1 WT OT-I cells into CD45.1 mice. Effector differentiation of OT-I cells will be assessed as described above.

Figure 15:
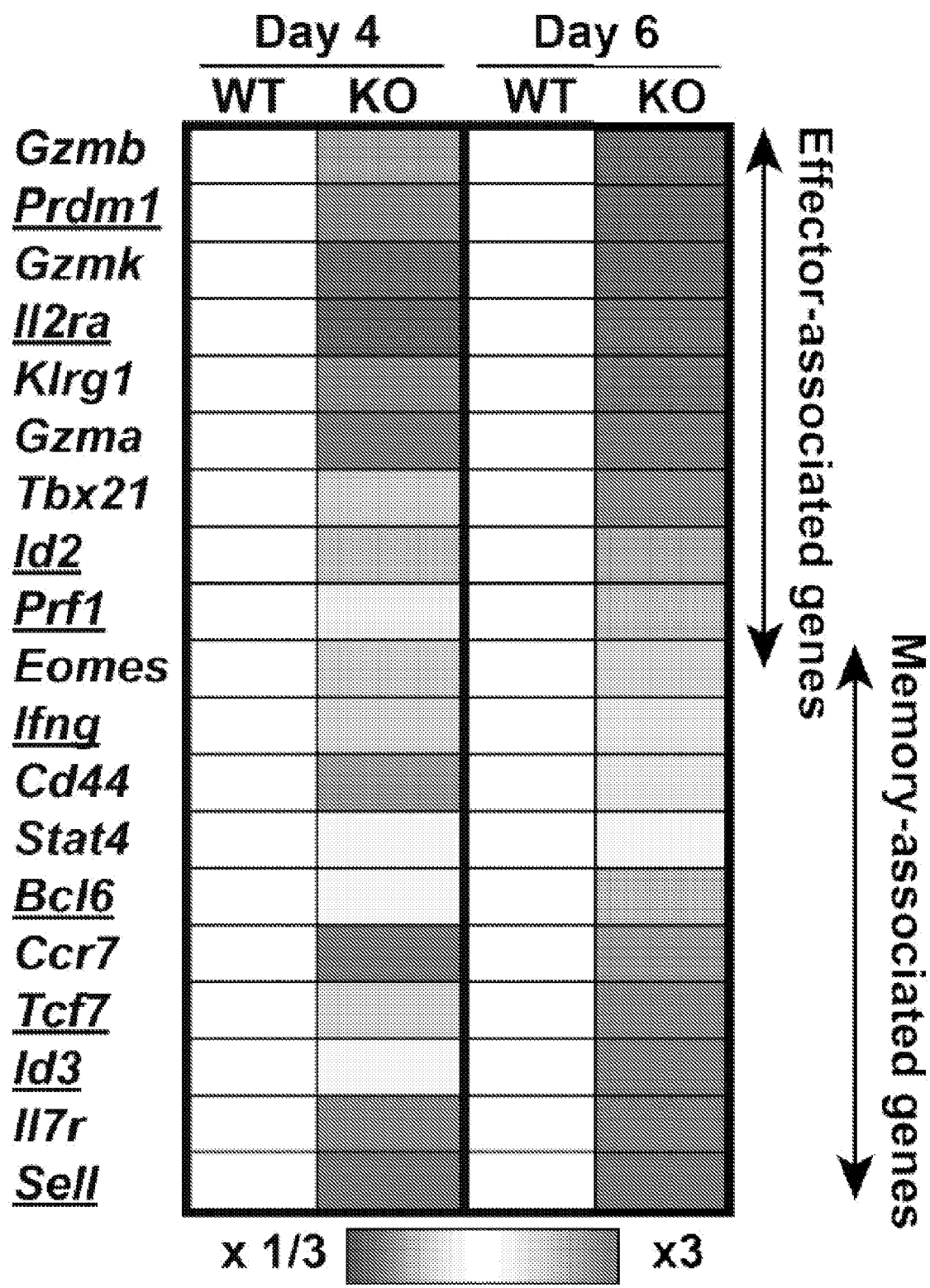
FIG. 15 depicts a heatmap showing altered expression of genes associated with effector or memory differentiation between Tfap4$^{-/-}$ and WT OT-I cells following Lm-Ova infection. Gene expression in Tfap4$^{-/-}$ (KO) or control WT OT-I T cells recovered from congenic host mice 4 and 6 days after infection with Lm-Ova. Expression levels relative to WT OT-I are shown by a heatmap. Genes that are directly bound by AP4 are underlined.
Figure 16A:
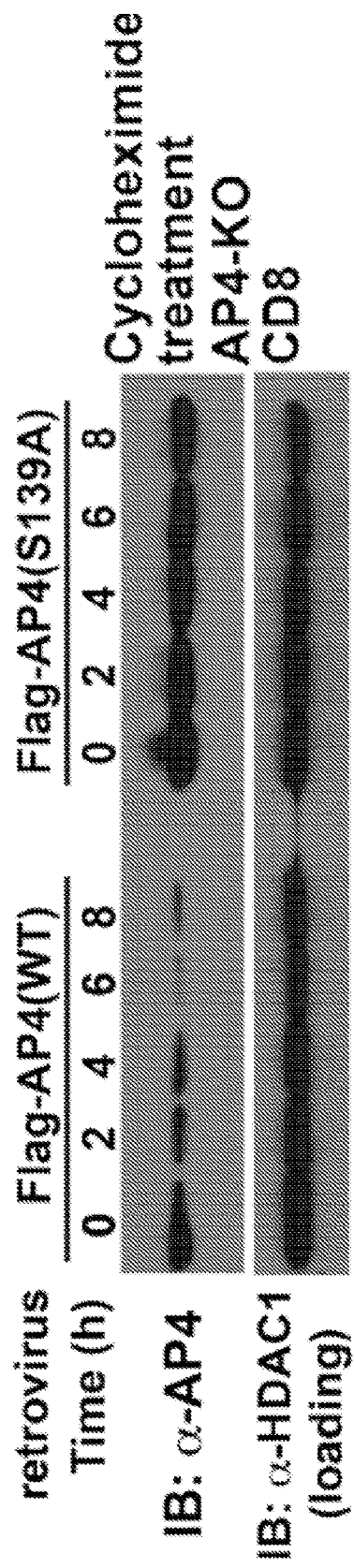
FIG. 16A, FIG. 16B, and FIG. 16C depicts immunoblots and flow cytometry plots shows the generation of degradation-resistant mutant of AP4.
Figure 16B:
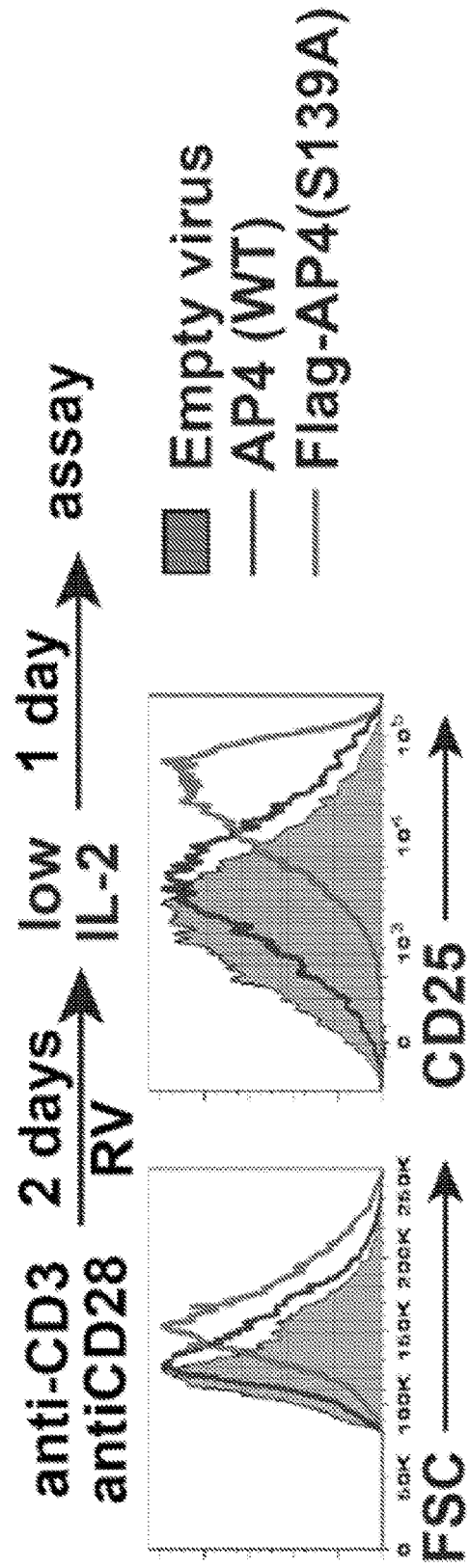
Figure 16C:
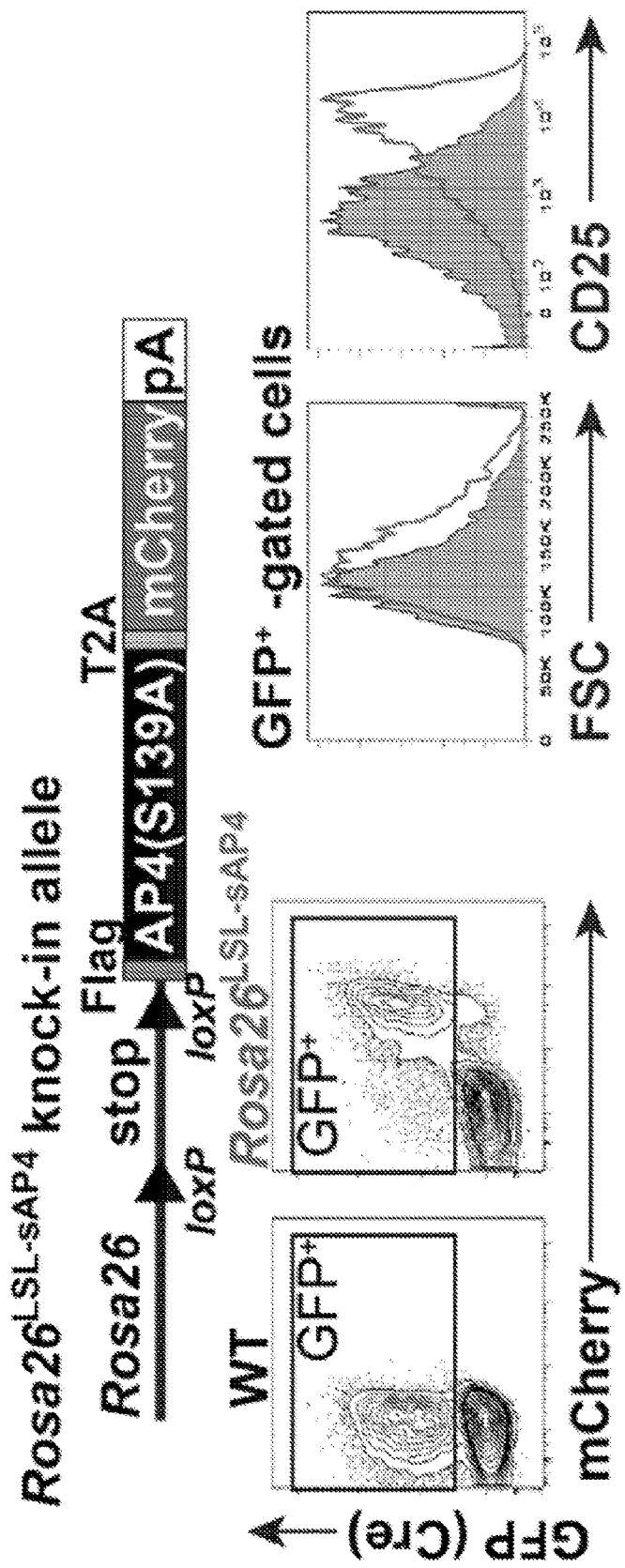
Figure 17A:
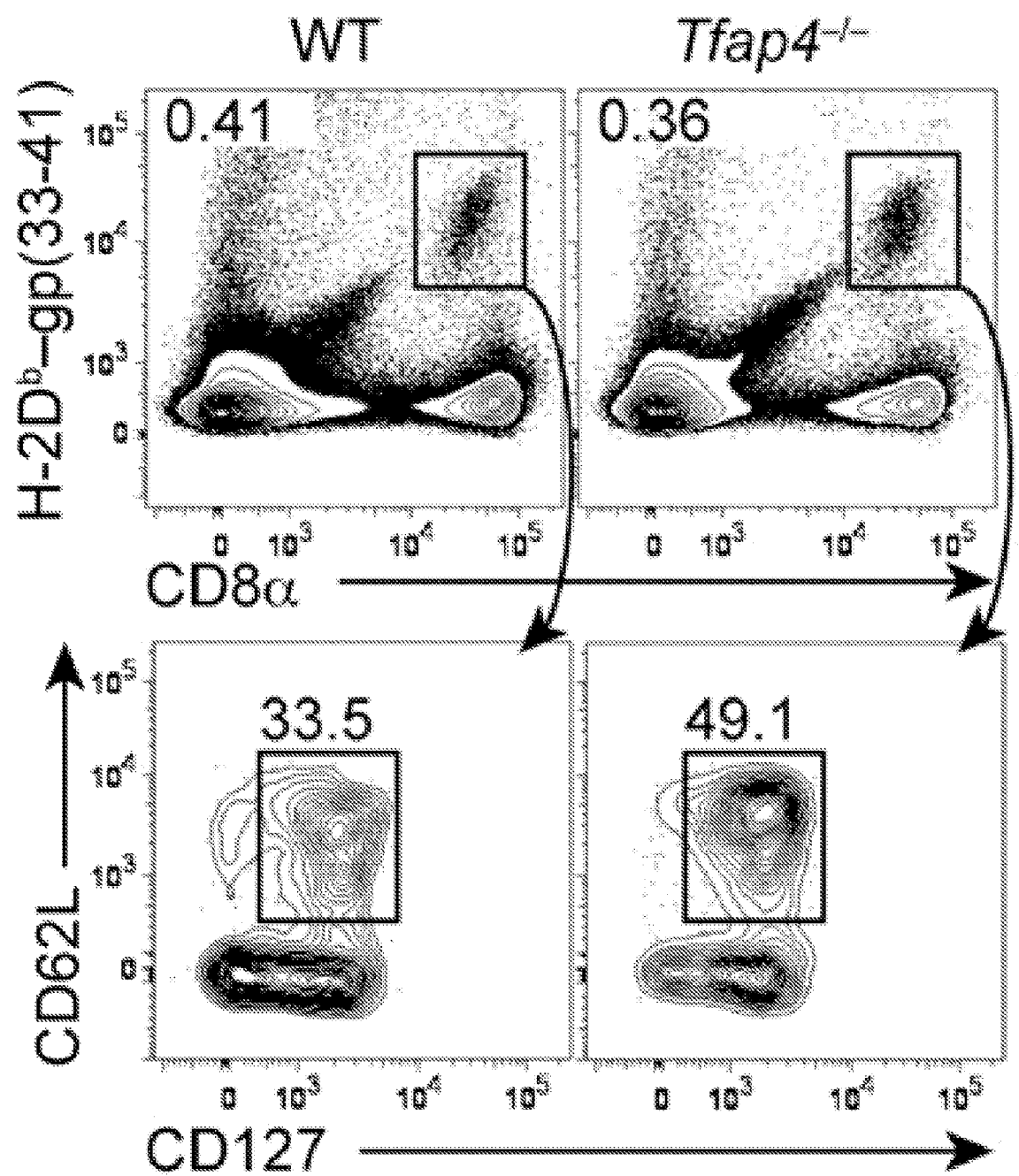
Figure 17D:
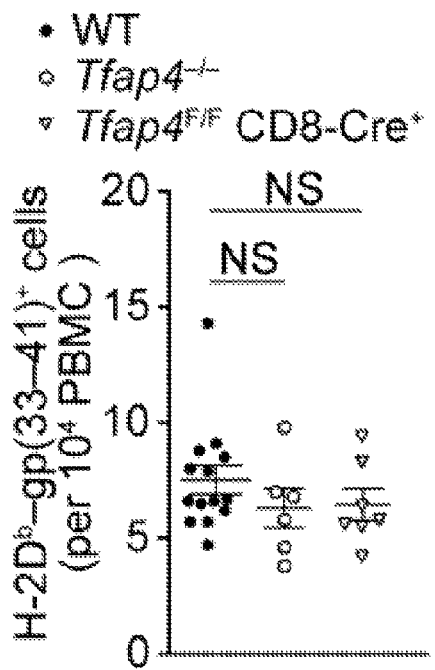
Figure 17E:
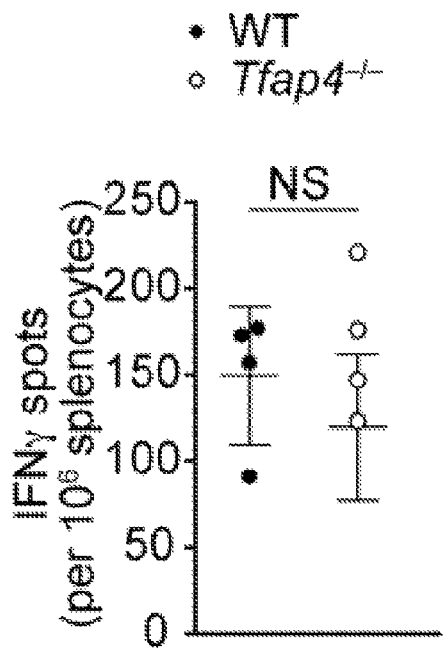
Figures 17F, 17G:
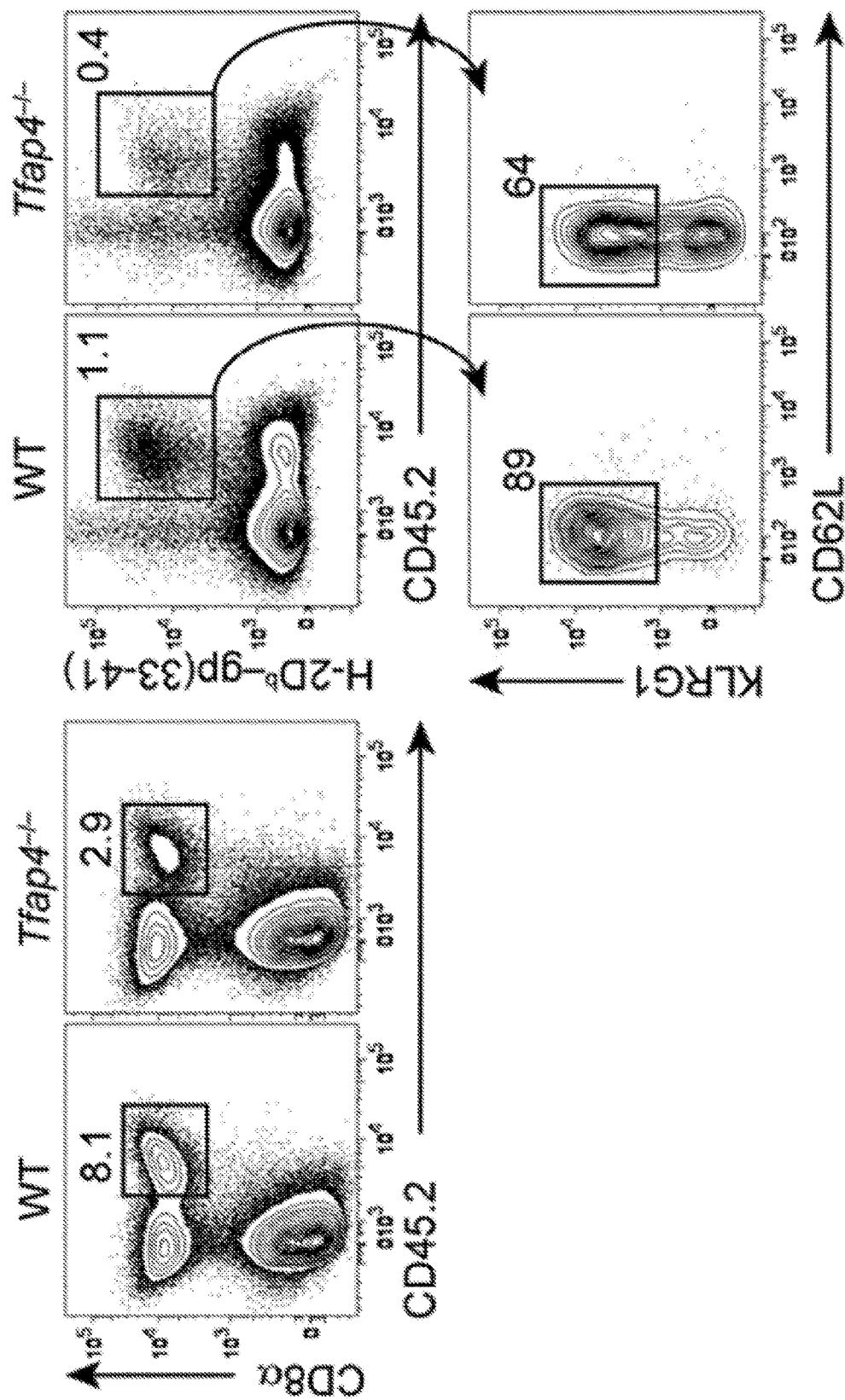
Figure 17J:
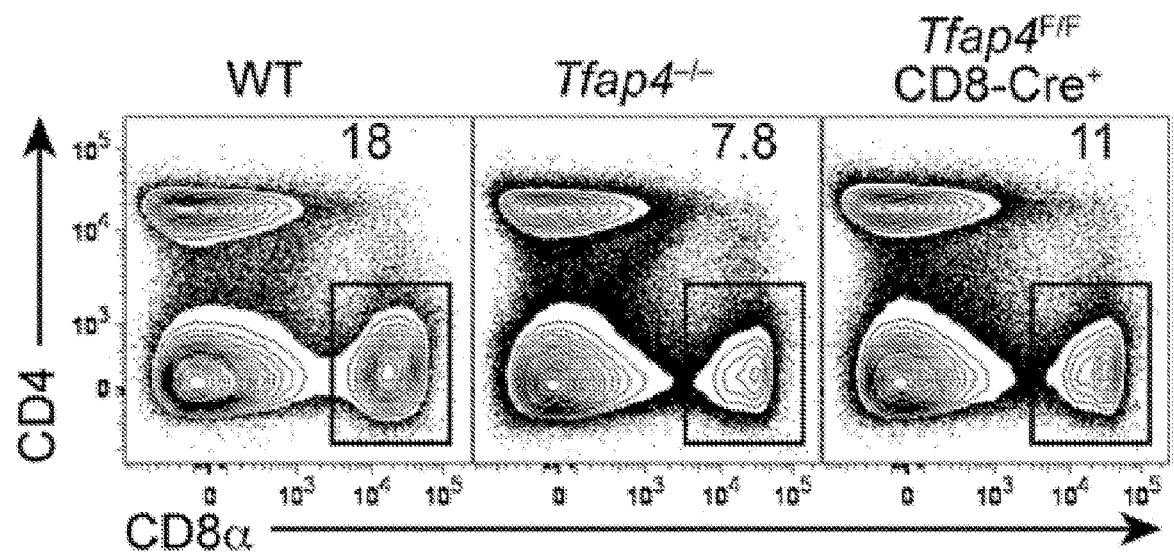
Figure 17K:
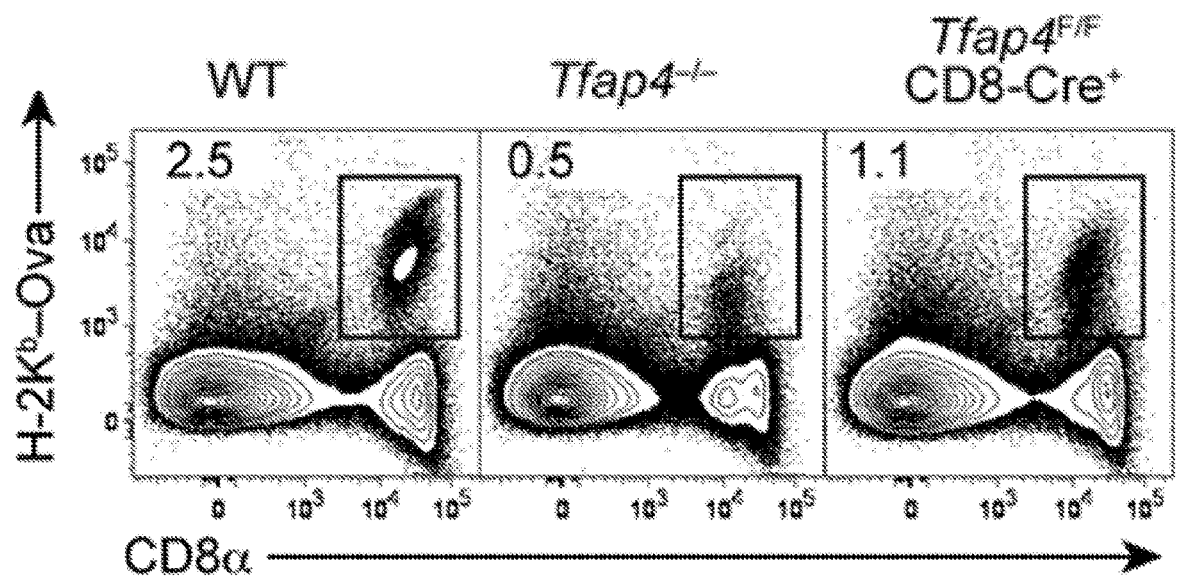
Figure 17L:
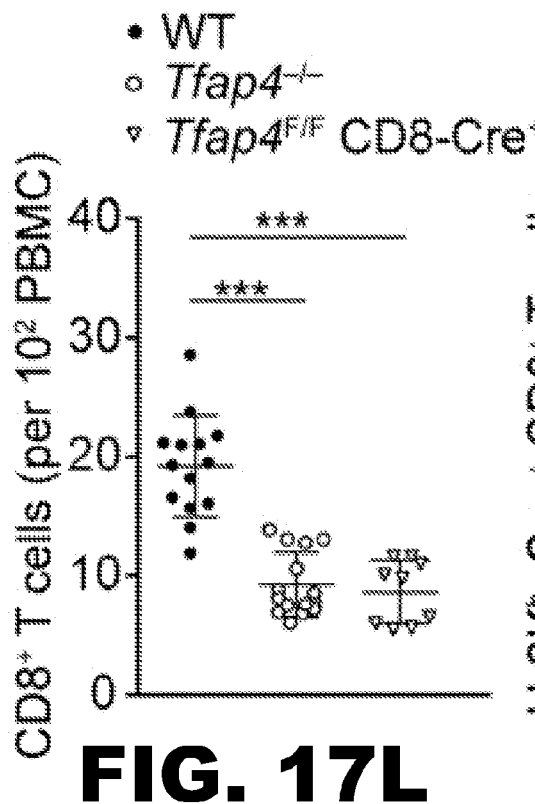
Figure 17M:
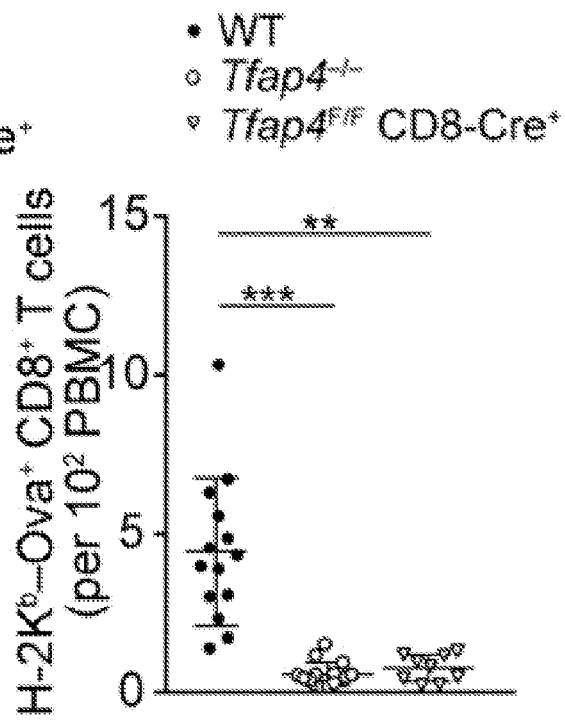
Figure 17N:
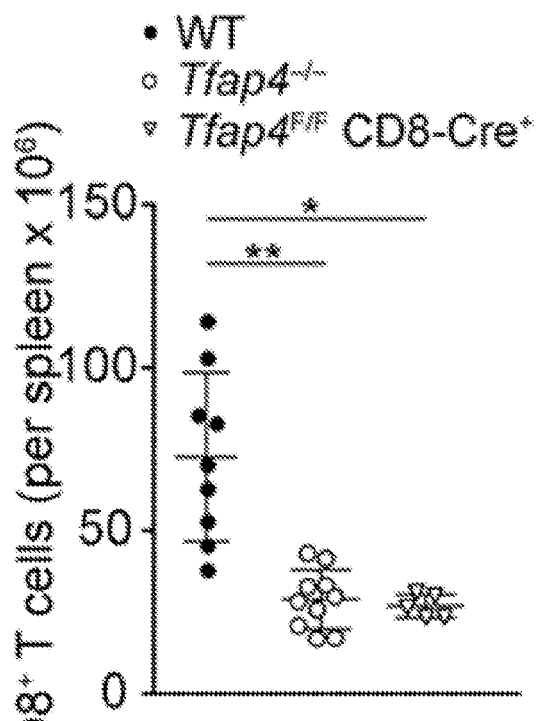
Figure 17O:
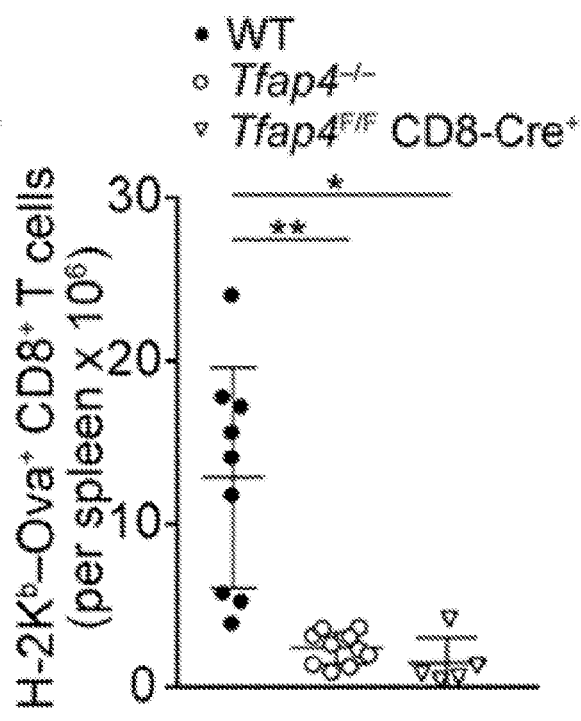

It is predicted that expression of effector-associated genes will be partially restored by the treatment with IL2-IC. FIG. 15 shows expression of representative effector- and memory-associated genes in WT and Tfap4$^{-/-}$ OT-I cells. Whereas it is predicted that non-AP4 targets, such as Gzmb and Klrg1, will be restored, Prdm1 and Id2 expression may remain diminished in Tfap4$^{-/-}$ cells treated with IL2-IC. Transduction of cytokine-primed OT-I cells without TCR priming has been validated, which allows expression of a gene of interest in TCR-tg cells.[4] However, if initial results suggest the potential for artifacts arising from in vitro manipulation, this can be avoided by using newly generated Rosa26$^{LSL-sAP4}$ mice (FIG. 16A, FIG. 16B, and FIG. 16C). Germline transmission of this allele in a pure C57BL6 background has been obtained, which will be crossed with mice harboring OT-I and Rosa26$^{CreERT2}$ alleles.

Example 11. Determine Whether AP4 is Required for the Development of Functional Memory CD8+ T Cells IL-2R signals during primary responses are essential for the development of memory CD8+ T cells that are capable of secondary expansion,[15] possibly by establishing epigenetic states that facilitate robust proliferative burst. Since secondary expansion of Tfap4$^{-/-}$ CD8+ T cells is impaired despite normal steady-state memory cell numbers (FIG. 17A, FIG. 17B, FIG. 17C, FIG. 17C, FIG. 17D, FIG. 17E, FIG. 17F, FIG. 17G, FIG. 17F, FIG. 17G, FIG. 17H, FIG. 17I, FIG. 17J, FIG. 17K, FIG. 17L, FIG. 17M, FIG. 17N, and FIG. 17O), it will be determined whether AP4 expression during primary responses programs fully functional memory CD8+ T cells either through IL-2R signals or as downstream of IL-2R signals. To test this, OT-I; Rosa26$^{CreERT2}$, OT-I; Rosa26$^{CreERT2}$; Tfap4$^{-/-}$, or OT-I; Rosa26$^{CreERT2}$; Tfap4$^{F/F}$ cells will be transferred into congenic host mice and the mice will be infected with Vaccinia-Ova, followed by Tamoxifen treatment between days 14-45. Secondary expansion of memory OT-I cells with distinct AP4 expression histories will be determined by challenge with high-dose Lm-Ova infection (FIG. 18). As a complementary approach to test whether expression of AP4 in recall responses restores secondary expansion of Tfap4$^{-/-}$ memory cells, OT-I; Rosa26$^{CreERT2/LSL-sAP4}$; Tfa4$^{-/-}$ control OT-I; Rosa26$^{CreERT2/LSL-sAP4}$ cells will be used and AP4 specifically during recall responses will be expressed by treating the recipient mice with Tamoxifen.

Figure 19A:
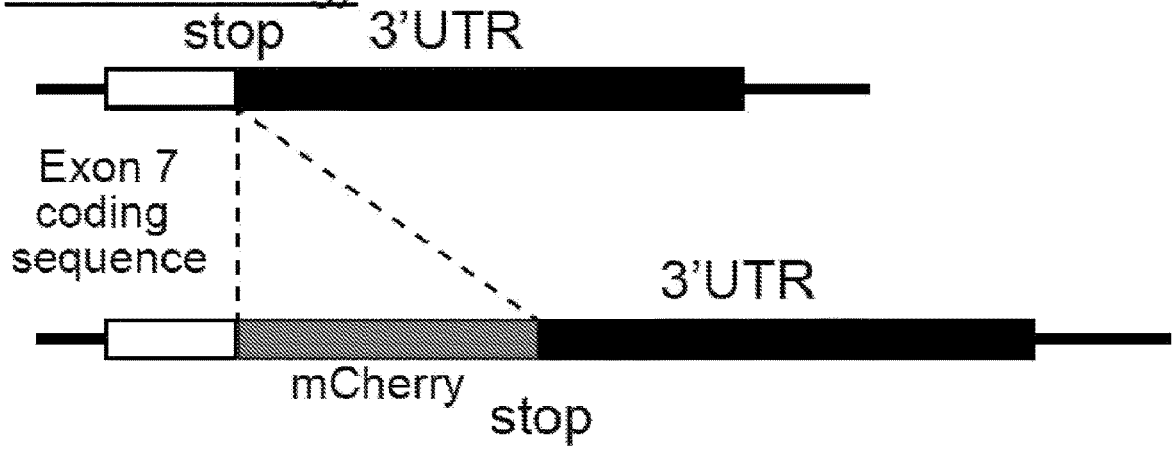
FIG. 19A, FIG. 19B, and FIG. 19C depict a schematic, immunoblot and flow cytometry plot of the generation of an AP4-mCherry fusion allele to track expression of AP4 protein at the single cell level.
Figure 19B:
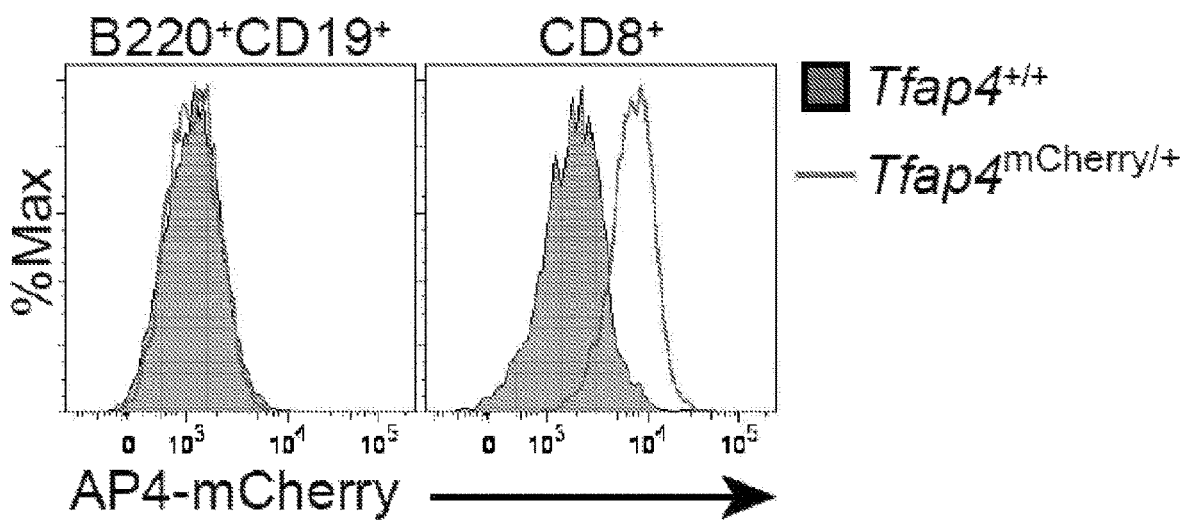
Figure 19C:
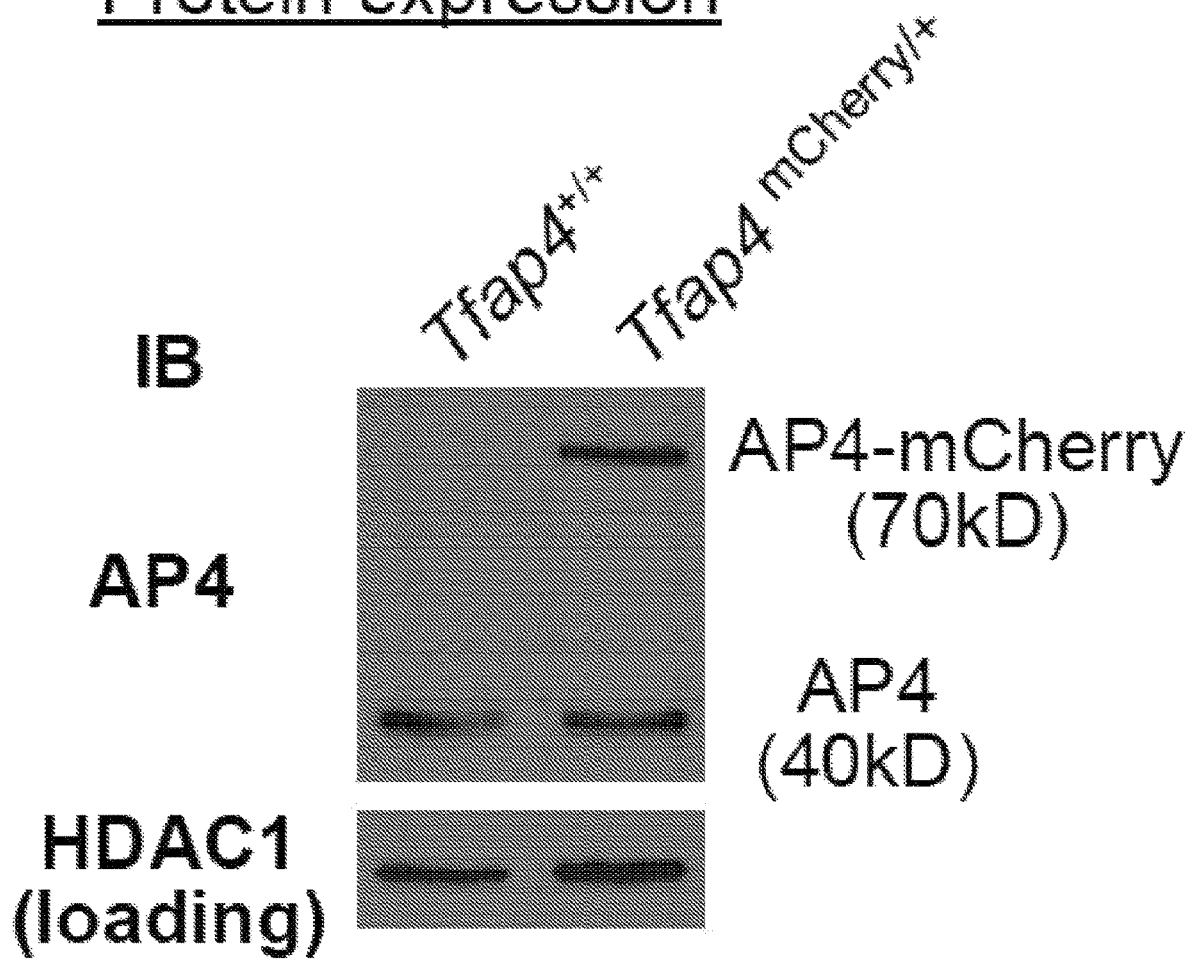

Two possible outcomes of the experiment using AP4 deletion between primary and secondary responses are possible. If these cells expand better than Tfap4$^{-/-}$ cells, the result would suggest that AP4 expression during the primary responses is sufficient to program "good" memory cells. If this is the case, follow-up experiments will test whether this process is IL-2R-dependent. Epigenetic profiling of memory cells generated in the presence or absence of AP4 will also be compared using ATAC-sequencing, which requires only a small number of cells. Alternatively, if no differences are observed between the Tfap4$^{-/-}$ and Tfap4$^{F/F}$ cohorts, it will be concluded that AP4 is required for secondary expansion of memory cells. In this scenario; however, it will not be distinguished whether the presence and absence of AP4 expression during primary responses programs memory cells differently. This question could be addressed by a second set of experiments in which AP4 will be selectively restored during the recall response using the newly generated Rosa26$^{LSL-sAP4}$ allele. If a rescue of secondary expansion of Tfap4$^{-/-}$ memory cells is observed with this approach, the result would indicate that AP4 is dispensable for the programming of "good" memory cells in primary responses. The results would also suggest that IL-2R signals program memory cells during primary responses independent of AP4, or the signals enhance upregulation of AP4 in the recall response. Kinetics of AP4 expression will be examined at a single cell level during recall responses using the AP4-mCherry protein reporter allele generated (FIG. 19A, FIG. 19B, and FIG. 19C). If no rescue is seen, the result would also support that AP4 is essential to program competent memory cells during primary responses. Any outcome will be pursued at the mechanistic level using gene expression and epigenetic analyses.

REFERENCES FOR THE EXAMPLES

1. Kaech, S. M., Cui, W., Transcriptional control of effector and memory CD8+ T cell differentiation. *Nat Rev Immunol* 12, 749-61 (2012).
2. Kaech, S. M., Wherry, E. J., Heterogeneity and cell-fate decisions in effector and memory CD8+ T cell differentiation during viral infection. *Immunity* 27, 393-405 (2007).

3. Virgin, H. W., Wherry, E. J., Ahmed, R., Redefining chronic viral infection. *Cell* 138, 30-50 (2009).
4. Chou, C., Pinto, A. K., Curtis, J. D., Persaud, S. P., Cella, M., Lin, C. C., Edelson, B. T., Allen, P. M., Colonna, M., Pearce, E. L., Diamond, M. S., Egawa, T., c-Myc-induced transcription factor AP4 is required for host protection mediated by CD8+ T cells. *Nat Immunol* 15, 884-93 (2014).
5. Satpathy, A. T., Briseno, C. G., Cai, X., Michael, D. G., Chou, C., Hsiung, S., Bhattacharya, D., Speck, N. A., Egawa, T., Runx1 and Cbfbeta regulate the development of Flt3+ dendritic cell progenitors and restrict myeloproliferative disorder. *Blood* 123, 2968-77 (2014).
6. Kim, B., Sasaki, Y., Egawa, T., Restriction of Nonpermissive RUNX3 Protein Expression in T Lymphocytes by the Kozak Sequence. *J Immunol* 195, 1517-23 (2015).
7 Henson, D. M., Chou, C., Sakurai, N., Egawa, T., A silencer-proximal intronic region is required for sustained CD4 expression in postselection thymocytes. *J Immunol* 192, 4620-7 (2014).
8. Egawa, T., Littman, D. R., Transcription factor AP4 modulates reversible and epigenetic silencing of the Cd4 gene. *Proc Natl Acad Sci USA* 108, 14873-8 (2011).
9. Cui, W., Kaech, S. M., Generation of effector CD8+ T cells and their conversion to memory T cells. *Immunol Rev* 236, 151-66 (2010).
10. Wang, R., Dillon, C. P., Shi, L. Z., Milasta, S., Carter, R., Finkelstein, D., McCormick, L. L., Fitzgerald, P., Chi, H., Munger, J., Green, D. R., The transcription factor Myc controls metabolic reprogramming upon T lymphocyte activation. *Immunity* 35, 871-82 (2011).
11. Huang, C. Y. B., A. L.; Walker, L. M.; Bassing, C. H.; Sleckman, B. P., Dynamic regulation of c-Myc proto-oncogene expression during lymphocyte development revealed by a GFP-c-Myc knock-in mouse. *Eur J Immunol* 38, 342-49 (2008).
12. Kalia, V., Sarkar, S., Subramaniam, S., Haining, W. N., Smith, K. A., Ahmed, R., Prolonged interleukin-2Ralpha expression on virus-specific CD8+ T cells favors terminal-effector differentiation in vivo. *Immunity* 32, 91-103 (2010).
13. Zehn, D., Lee, S. Y., Bevan, M. J., Complete but curtailed T-cell response to very low-affinity antigen. *Nature* 458, 211-4 (2009).
14. D'Souza, W. N., Lefrancois, L., IL-2 is not required for the initiation of CD8 T cell cycling but sustains expansion. *J Immunol* 171, 5727-35 (2003).
15. Williams, M. A., Tyznik, A. J., Bevan, M. J., Interleukin-2 signals during priming are required for secondary expansion of CD8+ memory T cells. *Nature* 441, 890-3 (2006).
16. Pipkin, M. E., Sacks, J. A., Cruz-Guilloty, F., Lichtenheld, M. G., Bevan, M. J., Rao, A., Interleukin-2 and inflammation induce distinct transcriptional programs that promote the differentiation of effector cytolytic T cells. *Immunity* 32, 79-90 (2010).
17. Hu, Y. F., Luscher, B., Admon, A., Mermod, N., Tjian, R., Transcription factor AP-4 contains multiple dimerization domains that regulate dimer specificity. *Genes Dev* 4, 1741-52 (1990).
18. Mermod, N., Williams, T. J., Tjian, R., Enhancer binding factors AP-4 and AP-1 act in concert to activate SV40 late transcription in vitro. *Nature* 332, 557-61 (1988).
19. Joshi, N. S., Cui, W., Chandele, A., Lee, H. K., Urso, D. R., Hagman, J., Gapin, L., Kaech, S. M., Inflammation directs memory precursor and short-lived effector CD8(+) T cell fates via the graded expression of T-bet transcription factor. *Immunity* 27, 281-95 (2007).
20. Sarkar, S., Kalia, V., Haining, W. N., Konieczny, B. T., Subramaniam, S., Ahmed, R., Functional and genomic profiling of effector CD8 T cell subsets with distinct memory fates. *J Exp Med* 205, 625-40 (2008).
21. Maekawa, Y., Minato, Y., Ishifune, C., Kurihara, T., Kitamura, A., Kojima, H., Yagita, H., Sakata-Yanagimoto, M., Saito, T., Taniuchi, I., Chiba, S., Sone, S., Yasutomo, K., Notch2 integrates signaling by the transcription factors RBP-J and CREB1 to promote T cell cytotoxicity. *Nat Immunol* 9, 1140-7 (2008).
22. Shrestha, B., Diamond, M. S., Role of CD8+ T cells in control of West Nile virus infection. *J Virol* 78, 8312-21 (2004).
23. Suthar, M. S., Diamond, M. S., Gale, M., Jr., West Nile virus infection and immunity. *Nat Rev Microbiol* 11, 115-28 (2013).
24. Loven, J., Orlando, D. A., Sigova, A. A., Lin, C. Y., Rahl, P. B., Burge, C. B., Levens, D. L., Lee, T. I., Young, R. A., Revisiting global gene expression analysis. *Cell* 151, 476-82 (2012).
25. Frye, M., Watt, F. M., The RNA methyltransferase Misu (NSun2) mediates Myc-induced proliferation and is upregulated in tumors. *Current biology: CB* 16, 971-81 (2006).
26. Gautier, T., Berges, T., Tollervey, D., Hurt, E., Nucleolar KKE/D repeat proteins Nop56p and Nop58p interact with Nop1p and are required for ribosome biogenesis. *Molecular and cellular biology* 17, 708898 (1997).
27. Hayano, T., Yanagida, M., Yamauchi, Y., Shinkawa, T., Isobe, T., Takahashi,
N., Proteomic analysis of human Nop56p-associated pre-ribosomal ribonucleoprotein complexes. Possible link between Nop56p and the nucleolar protein treacle responsible for Treacher Collins syndrome. *The Journal of biological chemistry* 278, 34309-19 (2003).
28. Barna, M., Pusic, A., Zolfo, O., Costa, M., Kondrashov, N., Rego, E., Rao,
P. H., Ruggero, D., Suppression of Myc oncogenic activity by ribosomal protein haploinsufficiency. *Nature* 456, 971-5 (2008).
29. Ruggero, D., The role of Myc-induced protein synthesis in cancer. *Cancer research* 69, 8839-43 (2009).
30. Luscher, B., Eisenman, R. N., c-myc and c-myb protein degradation: effect of metabolic inhibitors and heat shock. *Molecular and cellular biology* 8, 2504-12 (1988).
31. Hirsch, C. A., Hiatt, H. H., Turnover of liver ribosomes in fed and in fasted rats. *The Journal of biological chemistry* 241, 5936-40 (1966).
32. Miller, B. G., The biological half-lives of ribosomal and transfer RNA in the mouse uterus. *The Journal of endocrinology* 59, 81-5 (1973).
33. Sinclair, L. V., Rolf, J., Emslie, E., Shi, Y. B., Taylor, P. M., Cantrell, D. A., Control of amino-acid transport by antigen receptors coordinates the metabolic reprogramming essential for T cell differentiation. *Nat Immunol* 14, 500-8 (2013).
34. Grajales-Reyes, G. E., Iwata, A., Albring, J., Wu, X., Tussiwand, R., Kc, W., Kretzer, N. M., Briseno, C. G., Durai, V., Bagadia, P., Haldar, M., Schonheit, J., Rosenbauer, F., Murphy, T. L., Murphy, K. M., Batf3 maintains autoactivation of Irf8 for commitment of a CD8alpha(+) conventional DC clonogenic progenitor. *Nat Immunol* 16, 708-17 (2015).
35. Schraml, B. U., Hildner, K., Ise, W., Lee, W. L., Smith, W. A., Solomon, B., Sahota, G., Sim, J., Mukasa, R., Cemerski, S., Hatton, R. D., Stormo, G. D., Weaver, C. T., Russell, J. H., Murphy, T. L., Murphy, K. M., The AP-1 transcription factor Batf controls T(H)17 differentiation. *Nature* 460, 405-9 (2009).

36. Boyman, O., Sprent, J., The role of interleukin-2 during homeostasis and activation of the immune system. *Nat Rev Immunol* 12, 180-90 (2012).

37. Johnson, L. D., Jameson, S. C., Immunology. A chronic need for IL-21. *Science* 324, 1525-6 (2009).

38. Kahan, S. M., Wherry, E. J., Zajac, A. J., T cell exhaustion during persistent viral infections. *Virology*, (2015).

39. Odorizzi, P. M., Wherry, E. J., Inhibitory receptors on lymphocytes: insights from infections. *J Immunol* 188, 2957-65 (2012).

40. Youngblood, B., Wherry, E. J., Ahmed, R., Acquired transcriptional programming in functional and exhausted virus-specific CD8 T cells. *Current opinion in HIV and AIDS* 7, 50-7 (2012).

41. Barber, D. L., Wherry, E. J., Masopust, D., Zhu, B., Allison, J. P., Sharpe, A. H., Freeman, G. J., Ahmed, R., Restoring function in exhausted CD8 T cells during chronic viral infection. *Nature* 439, 682-7 (2006).

42. West, E. E., Jin, H. T., Rasheed, A. U., Penaloza-Macmaster, P., Ha, S. J., Tan, W. G., Youngblood, B., Freeman, G. J., Smith, K. A., Ahmed, R., PD-L1 blockade synergizes with IL-2 therapy in reinvigorating exhausted T cells. *J Clin Invest* 123, 2604-15 (2013).

43. Brundler, M. A., Aichele, P., Bachmann, M., Kitamura, D., Rajewsky, K., Zinkernagel, R. M., Immunity to viruses in B cell-deficient mice: influence of antibodies on virus persistence and on T cell memory. *Eur J Immunol* 26, 2257-62 (1996).

44. Harker, J. A., Lewis, G. M., Mack, L., Zuniga, E. I., Late interleukin-6 escalates T follicular helper cell responses and controls a chronic viral infection. *Science* 334, 825-9 (2011).

45. Sander, S., Calado, D. P., Srinivasan, L., Kochert, K., Zhang, B., Rosolowski, M., Rodig, S. J., Holzmann, K., Stilgenbauer, S., Siebert, R., Bullinger, L., Rajewsky, K., Synergy between PI3K signaling and MYC in Burkitt lymphomagenesis. *Cancer cell* 22, 167-79 (2012).

46. Hoffman, B., Liebermann, D. A., Apoptotic signaling by c-MYC. *Oncogene* 27, 6462-72 (2008).

47. Odorizzi, P. M., Pauken, K. E., Paley, M. A., Sharpe, A., Wherry, E. J., Genetic absence of PD-1 promotes accumulation of terminally differentiated exhausted CD8+ T cells. *J Exp Med* 212, 1125-37 (2015).

48. Shedlock, D. J., Shen, H., Requirement for CD4 T cell help in generating functional CD8 T cell memory. *Science* 300, 337-9 (2003).

49. Wherry, E. J., Ha, S. J., Kaech, S. M., Haining, W. N., Sarkar, S., Kalia, V., Subramaniam, S., Blattman, J. N., Barber, D. L., Ahmed, R., Molecular signature of CD8+ T cell exhaustion during chronic viral infection. *Immunity* 27, 670-84 (2007).

50. Wherry, E. J., Blattman, J. N., Murali-Krishna, K., van der Most, R., Ahmed, R., Viral persistence alters CD8 T-cell immunodominance and tissue distribution and results in distinct stages of functional impairment. *J Virol* 77, 4911-27 (2003).

51. Matsushita, H., Vesely, M. D., Koboldt, D. C., Rickert, C. G., Uppaluri, R., Magrini, V. J., Arthur, C. D., White, J. M., Chen, Y. S., Shea, L. K., Hundal, J., Wendl, M. C., Demeter, R., Wylie, T., Allison, J. P., Smyth, M. J., Old, L. J., Mardis, E. R., Schreiber, R. D., Cancer exome analysis reveals a T-cell-dependent mechanism of cancer immunoediting. *Nature* 482, 400-4 (2012).

52. Crawford, A., Angelosanto, J. M., Kao, C., Doering, T. A., Odorizzi, P. M., Barnett, B. E., Wherry, E. J., Molecular and transcriptional basis of CD4(+) T cell dysfunction during chronic infection. *Immunity* 40, 289-302 (2014).

53. Blattman, J. N., Grayson, J. M., Wherry, E. J., Kaech, S. M., Smith, K. A., Ahmed, R., Therapeutic use of IL-2 to enhance antiviral T-cell responses in vivo. *Nat Med* 9, 540-7 (2003).

54. Rosenberg, S. A., IL-2: the first effective immunotherapy for human cancer. *J Immuno!* 192, 5451-8 (2014).

55. Sim, G. C., Radvanyi, L., The IL-2 cytokine family in cancer immunotherapy. *Cytokine Growth Factor Rev* 25, 377-90 (2014).

What is claimed is:

1. A composition comprising isolated T cells, wherein the T cells comprise a recombinant vector comprising a nucleic acid sequence encoding activating enhancer-binding protein 4 (AP4), wherein the AP4 comprises the amino acid sequence of SEQ ID NO: 2, wherein expression of the AP4 exhibits increased stability relative to wild-type AP4 and induces T cell proliferation.

2. The composition of claim 1, wherein the AP4 consists of the amino acid sequence of SEQ ID NO: 2.

3. A method to improve adoptive cellular immunotherapy in a subject, the method comprising administering to the subject a therapeutic comprising isolated T cells, wherein the T cells comprise a recombinant vector comprising a nucleic acid sequence encoding activating enhancer-binding protein 4 (AP4), wherein the AP4 comprises the amino acid sequence of SEQ ID NO: 2, wherein expression of the AP4 exhibits increased stability relative to wild-type AP4 and induces T cell proliferation.

4. The method of claim 3, wherein the subject has cancer or a chronic viral infection.

5. The method of claim 3, wherein the T cells are autologous to the subject.

6. The method of claim 3, wherein the T cells are heterologous/non-autologous.

7. The method of claim 3, wherein the AP4 consists of the amino acid sequence of SEQ ID NO: 2.

8. The method of claim 3, wherein the T cell is a CD8+ T cell.

9. A method to reduce tumor growth in a subject, the method comprising administering to the subject a therapeutic comprising isolated T cells, wherein the T cells comprise a recombinant vector comprising a nucleic acid sequence encoding activating enhancer-binding protein 4 (AP4), wherein the AP4 comprises the amino acid sequence of SEQ ID NO: 2, wherein expression of the AP4 exhibits increased stability relative to wild-type AP4 and induces T cell proliferation.

10. The method of claim 9, wherein the T cells are autologous to the subject.

11. The method of claim 9, wherein the T cells are heterologous/non-autologous.

12. The method of claim 9, wherein the AP4 consists of SEQ ID NO: 2.

13. The method of claim 9, wherein the T cell is a CD8+ T cell.

* * * * *